(12) United States Patent
Moore et al.

(10) Patent No.: US 12,365,928 B2
(45) Date of Patent: Jul. 22, 2025

(54) SCALABLE BIOSYNTHESIS OF THE SEAWEED NEUROCHEMICAL KAINIC ACID

(71) Applicant: The Regents of the University of California, Oakland, CA (US)

(72) Inventors: Bradley S. Moore, La Jolla, CA (US); Jonathan R. Chekan, La Jolla, CA (US); Shaun M. K. McKinnie, La Jolla, CA (US)

(73) Assignee: The Regents of the University of California, Oakland, CA (US)

(*) Notice: Subject to any disclaimer, the term of this patent is extended or adjusted under 35 U.S.C. 154(b) by 175 days.

(21) Appl. No.: 17/298,464

(22) PCT Filed: Dec. 3, 2019

(86) PCT No.: PCT/US2019/064221
§ 371 (c)(1),
(2) Date: May 28, 2021

(87) PCT Pub. No.: WO2020/117792
PCT Pub. Date: Jun. 11, 2020

(65) Prior Publication Data
US 2024/0279695 A1    Aug. 22, 2024

Related U.S. Application Data

(60) Provisional application No. 62/775,327, filed on Dec. 4, 2018.

(51) Int. Cl.
C12P 17/18       (2006.01)
C12N 9/02        (2006.01)
C12N 9/10        (2006.01)

(52) U.S. Cl.
CPC .......... C12P 17/188 (2013.01); C12N 9/0071 (2013.01); C12N 9/1085 (2013.01); C12Y 114/11 (2013.01); C12Y 205/01 (2013.01)

(58) Field of Classification Search
CPC ...... C12Y 205/01; C12Y 114/11; C12P 17/10; C12P 17/188; C12N 9/0071; C12N 9/1085; C07D 207/16; C07D 227/18; C07D 491/052
See application file for complete search history.

(56) References Cited

U.S. PATENT DOCUMENTS 5,352,799 A    10/1994 Monn
5,591,867 A    1/1997 Monn
2017/0321238 A1 11/2017 Houghton-Larsen et al.

OTHER PUBLICATIONS

Ahern et al. "Synthesis and characterization of [vinylidene-3H](−)-α-kainic acid at high specific activity," Journal of Labelled Compounds and Radiopharmaceuticals, Mar. 11, 2002 (Mar. 11, 2002), vol. 45, Iss. 5, pp. 401-405. entire document.
Brunson et al. "Biosynthesis of the neurotoxin domoic acid in a bloom-forming diatom," Science, Sep. 28, 2018 (Sep. 28, 2018), vol. 361, Iss. 6409, pp. 1356

(56) References Cited

OTHER PUBLICATIONS

Janouskovec, J. et al., "A common red algal origin of the apicomplexan, dinoflagellate, and heterokont plastids." *Proc. Natl. Acad. Sci. U. S. A.* 2010, 107, 10949-54.

Katoh, K. et al., "MAFFT online service: multiple sequence alignment, interactive sequence choice and visualization." *Brief. Bioinform.* 1-7 (2017). doi:10.1093/bib/bbx108.

Komiya, Y. et al., "Techniques applied in Japan for the control of Ascaris and hookworm infections-a review." Jpn. J. Med. Sci. Biol. 18, 1-17 (1965).

Konno, K. et al., "Acromelic acids A and B. Potent neuroexcitatory amino acids isolated from clitocybe acromelalga." J. Am. Chem. Soc. 110, 4807-4815 (1988).

Lee, S. H. et al., "Santonin-kainic acid complex as a mass chemotherapeutic of Ascaris lumbricoides control in Korea." Korean J. Parasitol. 10, 79-85 (1972).

Lelong, A. et al., "Pseudo-nitzschia (*Bacillariophyceae*) species, domoic acid and amnesic shellfish poisoning: revisiting previous paradigms." Phycologia 51, 168-216 (2012).

Lévesque, M. et al., "The kainic acid model of temporal lobe epilepsy." Neurosci. Biobehav. Rev. 37, 2887-2899 (2013).

Li, H. "Minimap and miniasm: fast mapping and de novo assembly for noisy long sequences." *Bioinformatics* 32, 2103-10 (2016).

Li, H. "Minimap2: pairwise alignment for nucleotide sequences." *Bioinformatics* 34, 3094-3100 (2018).

Lodge, D. "The history of the pharmacology and cloning of ionotropic glutamate receptors and the development of idiosyncratic nomenclature." Neuropharmacology 56, 6-21 (2009).

Maddison, W. P. et al., "Mesquite: a modular system for evolutionary analysis. Version 3.51 (2018)." Available at: http://www.mesquiteproject.org.

Martinez, S. et al., "Catalytic mechanisms of Fe(II)- and 2-oxoglutarate-dependent oxygenases." J. Biol. Chem. 290, 20702-11 (2015).

Matasci, N. et al. "Data access for the 1,000 Plants (1KP) project." Gigascience 3, 17 (2014).

Michael, T. P. et al., "High contiguity Arabidopsis thaliana genome assembly with a single nanopore flow cell." Nat. Commun. 9, 1-8 (2018).

Miyasaki, M. et al., "Studies on the components of Digenea simplex Ag. VII." Yakugaku Zasshi 76, 189-191 (1956).

Monier, A. et al. "Horizontal gene transfer of an entire metabolic pathway between a eukaryotic alga and its DNA virus." Genome Res. 19, 1441-9 (2009).

Mos, L. "Domoic acid: a fascinating marine toxin." Environ. Toxicol. Pharmacol. 9, 79-85 (2001).

Murakami S., et al., "Studies on the effective principles of Digenea simplex Aq. I. Separation of the effective fraction by liquid chromatography." J Pharm Soc Jpn 73:1026-1028 (1953).

Nitta, I., et al., "Structure of kainic acid and its isomer, allokainic acid." Nature 181, 761-2 (1958).

Pulido, O. M. "Domoic acid toxicologic pathology: A review." Mar. Drugs 6, 180-219 (2008).

Ramsey, U. P. et al., "Kainic acid and 1'-hydroxykainic acid from palmariales." Nat. Toxins 2, 286-292 (1994).

Saunders, G. W. et al., "Phylogenetic analyses of transcriptome data resolve familial assignments for genera of the red-algal Acrochaetiales-Palmariales Complex (Nemaliophycidae)." Mol. Phylogenet. Evol. 119, 151-159 (2018).

Schläpfer, P. et al. "Genome-wide prediction of metabolic enzymes, pathways, and gene clusters in plants." Plant Physiol. 173, 2041-2059 (2017).

Sheldon, R. A. et al., "Role of biocatalysis in sustainable chemistry." Chem. Rev. 118, 801-838 (2018).

Siitonen, V. et al. "Divergent non-heme iron enzymes in the nogalamycin biosynthetic pathway." Proc. Natl. Acad. Sci. 113, 5251-5256 (2016).

Silvestro, D. et al., "RaxmlGUI: A graphical front-end for RAxML." *Org. Divers. Evol.* 12, 335-337 (2012).

Stathakis, C. I. et al., "Total syntheses of (−)-α-kainic acid." European J. Org. Chem. 4661-4673 (2012). doi:10.1002/ejoc.201200243.

Tang, M.-C. et al., "Oxidative Cyclization in Natural Product Biosynthesis." Chem. Rev. acs.chemrev.6b00478 (2016). doi:10.1021/acs.chemrev.6b00478.

Tremblay, J.-F. "Shortage of kainic acid hampers neuroscience research." Chem. Eng. News 78, 14-15 (2000).

Vaser, R. et al., "Fast and accurate de novo genome assembly from long uncorrected reads." Genome Res. 27, 737-746 (2017).

Walker, B. J. et al., "Pilon: An integrated tool for comprehensive microbial variant detection and genome assembly improvement." *PLoS One* 9, (2014).

Werner, P. et al., "Cloning of a putative high-affinity kainate receptor expressed predominantly in hippocampal CA3 cells." Nature 351, 742-4 (1991).

Wick, R. R. et al., "Bandage: interactive visualization of de novo genome assemblies." *Bioinformatics* 31, 3350-2 (2015).

Winkelblech, J. et al., "Prenyltransferases as key enzymes in primary and secondary metabolism." Appl. Microbiol. Biotechnol. 99, 7379-7397 (2015).

Woodside, A. B. et al., "Trisammonium Geranyl Diphosphate." *Org. Synth.* 211-211 (2003). doi:10.1002/0471264180.os066.27.

Wright, J. L. C. et al., "Identification of domoic acid, a neuroexcitatory amino acid, in toxic mussels from eastern Prince Edward Island." Can. J. Chem. 67, 481-490 (1989).

Zhang, M. et al. "A short scalable route to (−)-α-kainic acid using Pt-catalyzed direct allylic amination." Chemistry 21, 3937-41 (2015).

Zhu, J. et al., "Kainic acid-induced neurodegenerative model: Potentials and limitations." J. Biomed. Biotechnol. 2011, (2011).

International Search Report and Written Opinion issued in International Application No. PCT/US2019/064221, mailed May 22, 2020, (May 22, 2020). 5 pages.

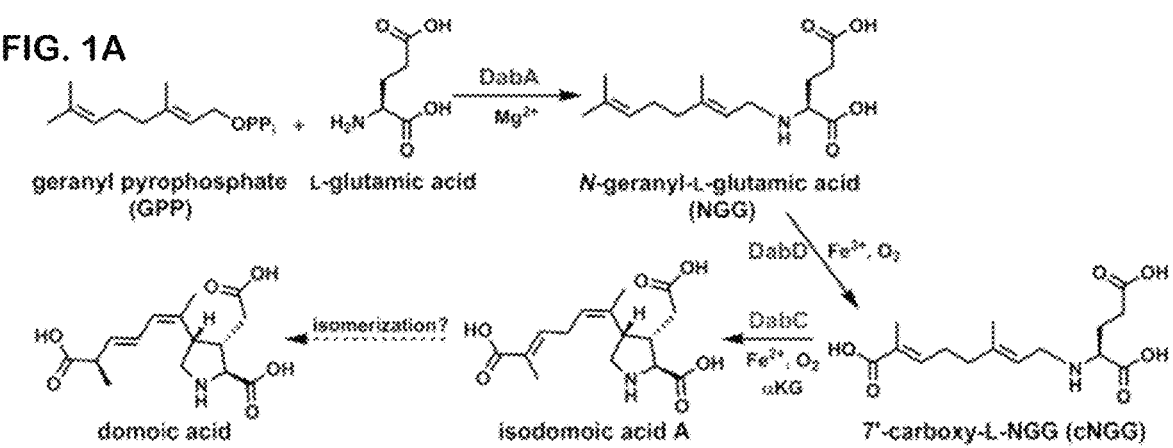
FIG. 1A
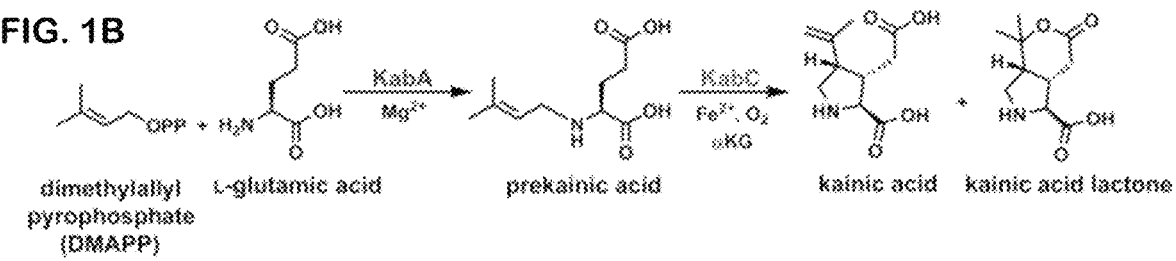
FIG. 1B
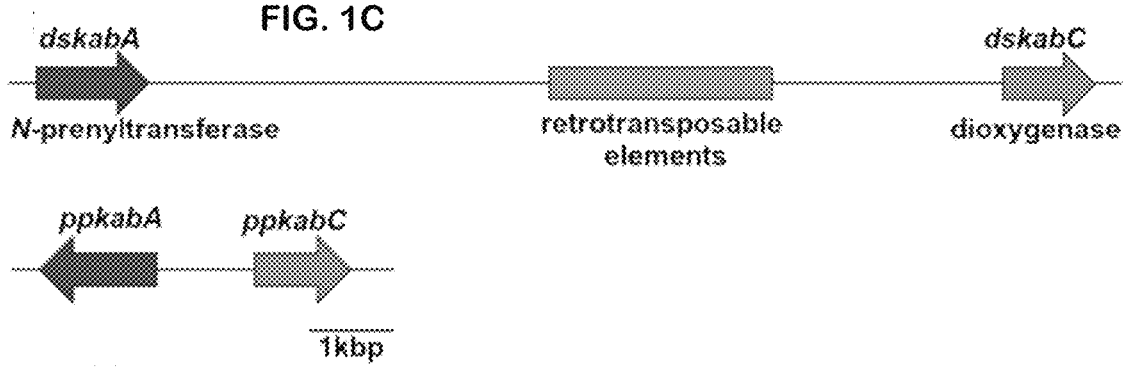
FIG. 1C
FIG. 1D

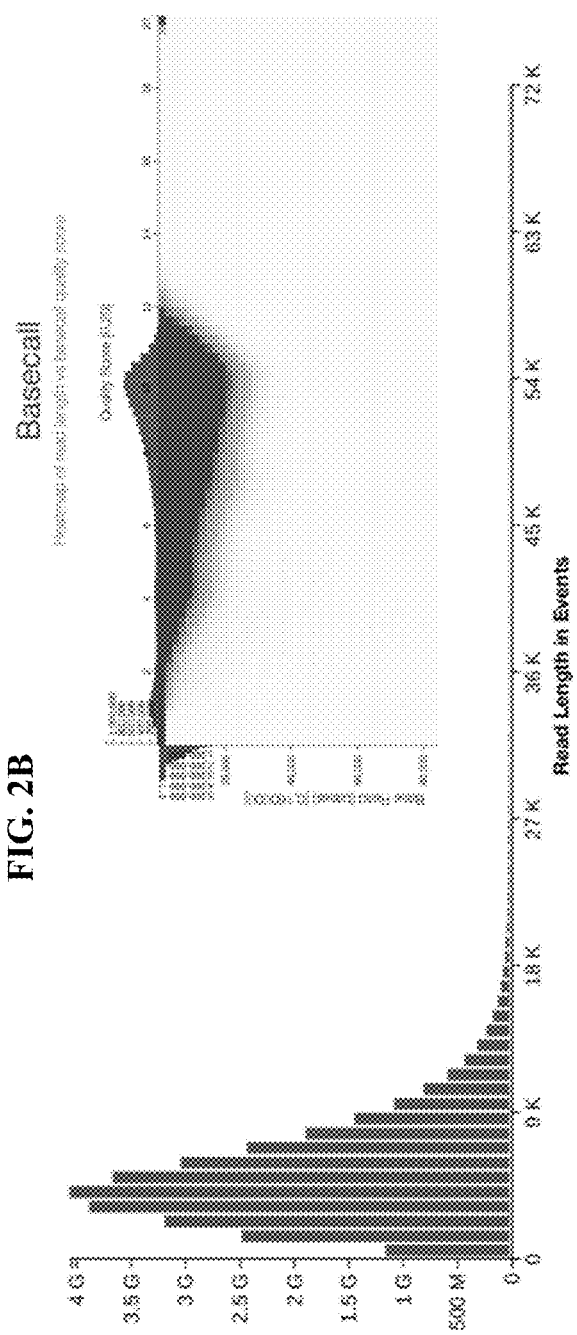
FIG. 2A
FIG. 2B
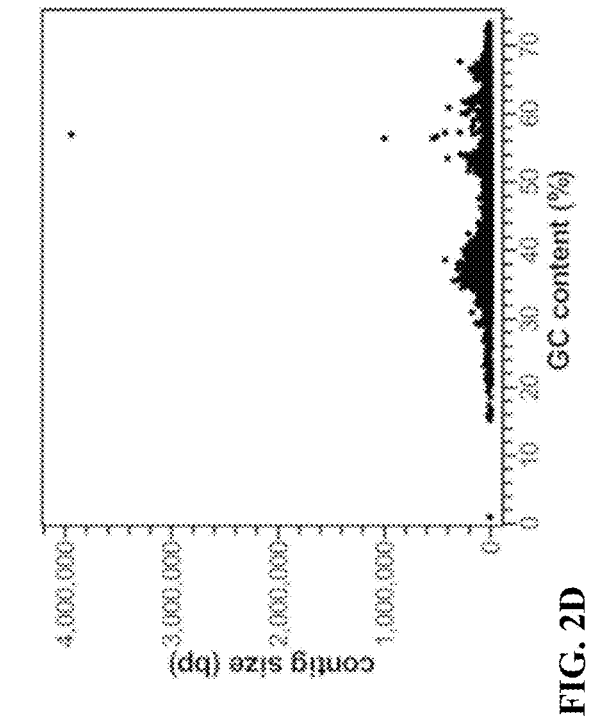
FIG. 2D
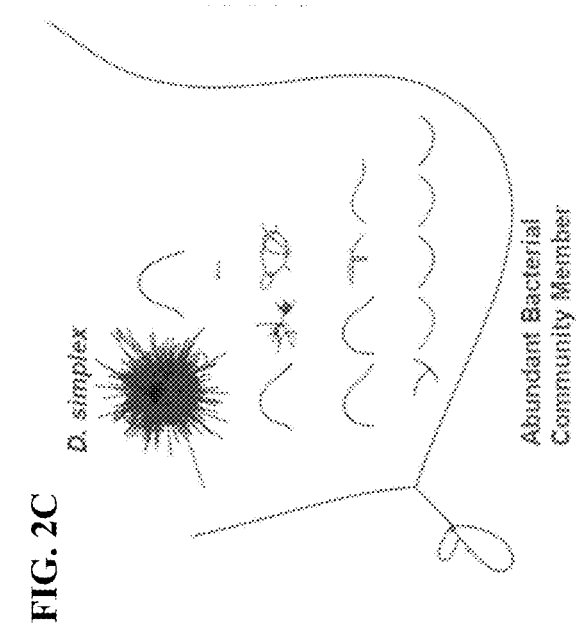
FIG. 2C

FIG. 14
NMR Analysis
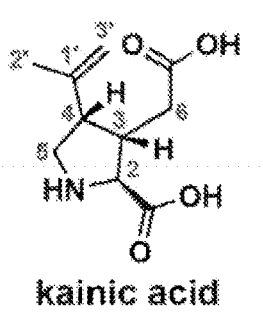
kainic acid
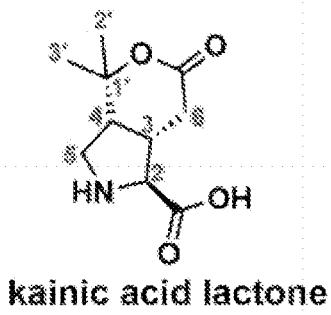
kainic acid lactone
NMR Comparison (Chemical shifts)
| Proton | Literature Kainic Acid[17] | Literature allo-kainic acid[17] | Purified Kainic Acid | Proton | Literature Kainic acid lactone[18] | Purified Kainic acid lactone |
|---|---|---|---|---|---|---|
| 2 | 4.01 | 3.37 | 4.07 | 2 | 3.98 | 3.97 |
| 3 | 3.00 | 3.10 | 3.05 | 5a | 3.76 | 3.73 |
| 4 | 3.00 | 2.90 | 2.97 | 3, 5b, 6a* | 3.1-3.4 | 3.13-3.24 |
| 5a | 3.54 | 3.54 | 3.60 | 5b | | 3.24 |
| 5b | 3.34 | 3.30 | 3.40 | 3 | | 3.20 |
| 6a | 2.3 | 2.35 | 2.34 | 6a | | 3.15 |
| 6b | 2.38 | 2.41 | 2.44 | 4 | 2.82 | 2.79 |
| 2' | 1.67 | 1.68 | 1.73 | 6b | 2.60 | 2.55 |
| 3' | 4.95 | 4.97 | 4.98, 4.73 | 2' | 1.50 | 1.48 |
| | | | | 3' | 1.42 | 1.39 |
*Literature kainic acid lactone shifts of these protons are reported as a range.

FIG. 15
NMR Correlations
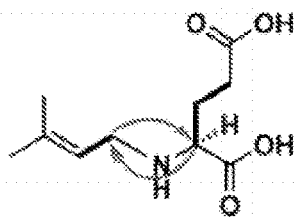
prekainic acid
(enzymatic)
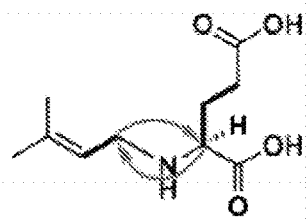
prekainic acid
(synthetic)
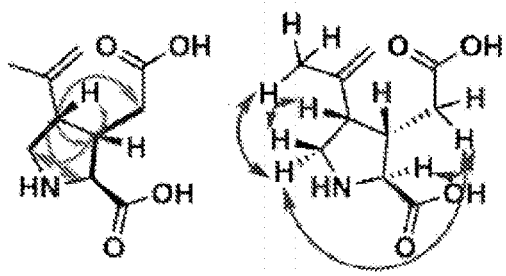
kainic acid
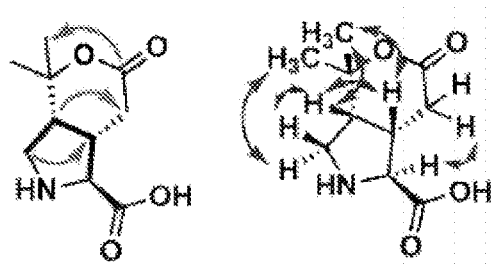
kainic acid lactone FIG. 17
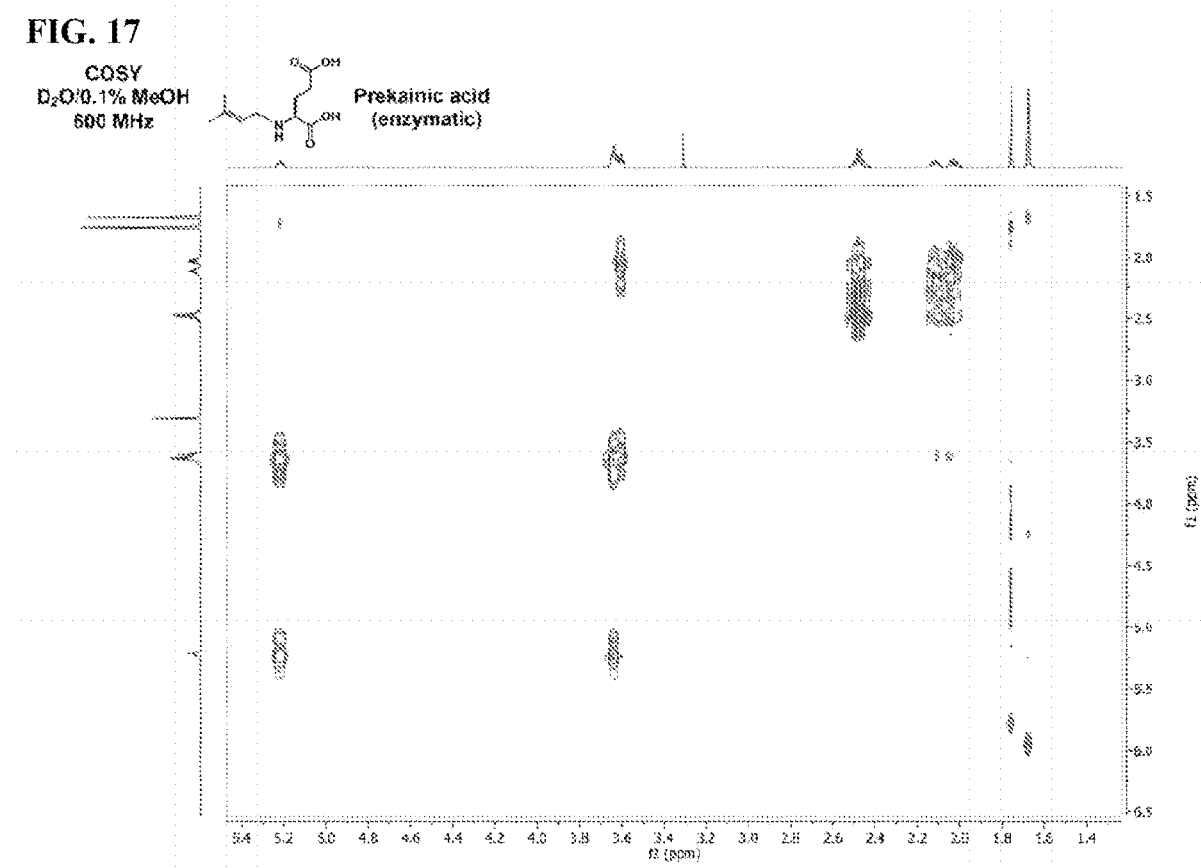
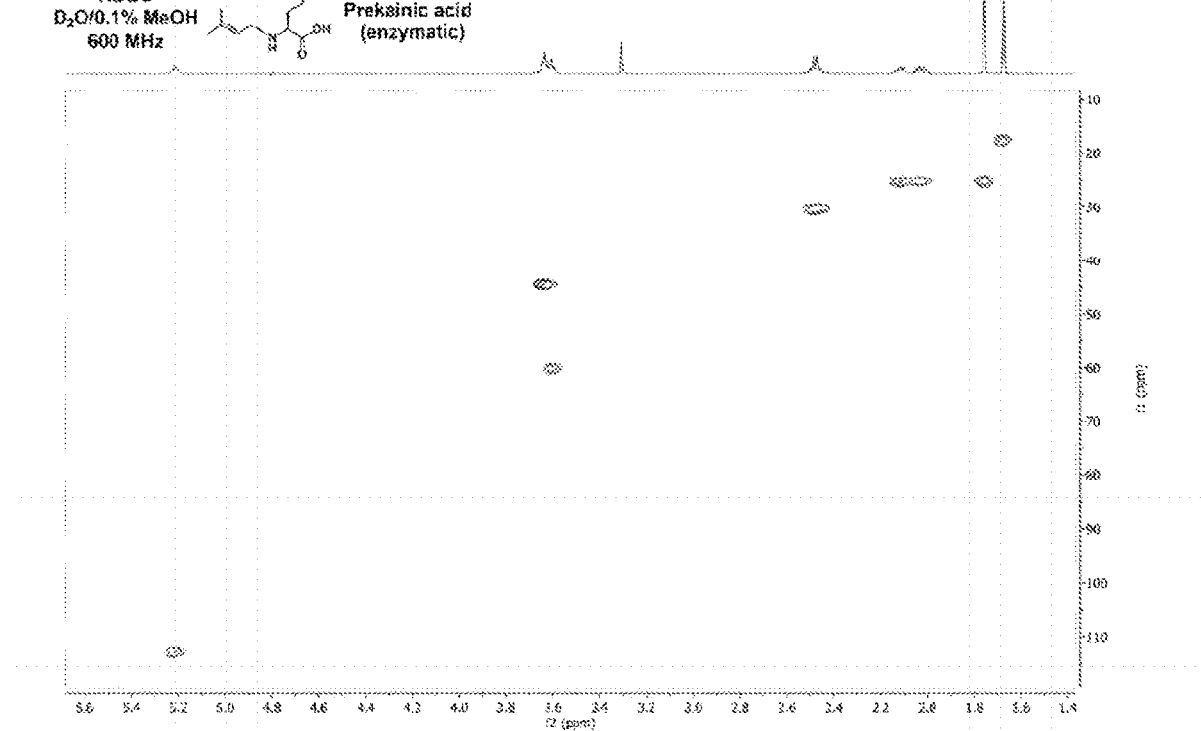

SCALABLE BIOSYNTHESIS OF THE SEAWEED NEUROCHEMICAL KAINIC ACID

RELATED PATENT APPLICATION

This patent application claims the benefit of U.S. Provisional Patent Application No. 62/775,327 filed on Dec. 4, 2018. The entire content of the foregoing patent application is incorporated herein by reference, including all text, tables and drawings.

STATEMENT OF GOVERNMENT SUPPORT

This invention was made with government support under GM085770 awarded by the National Institutes of Health. The government has certain rights in the invention.

BACKGROUND

Kainic acid, the flagship member of the kainoid family of natural neurochemicals, is a widely used neuropharmacology agent that helped unravel the key role of ionotropic glutamate receptors, including the kainate receptor, in the central nervous system. Worldwide shortages of this seaweed natural product in 2000 prompted numerous chemical syntheses that now number in excess of 70, including scalable preparations with as few as six-steps. Recently, the biosynthesis of the kainoid domoic acid was established in Pseudo-nitzschia diatoms that revealed nature's molecular logic in efficiently constructing their shared pyrrolidine ring with three contiguous stereogenic centers.

SUMMARY

Improved methods for the production of kainic acid and kainic acid lactone are needed. In embodiments, methods and compositions of the present disclosure address this need, and provide additional advantages as well.

A two-enzyme biosynthetic pathway to kainic acid was discovered in red macro algae. The biosynthetic genes appear to be co-clustered in genomes of *Digenea simplex* and the edible *Palmaria palmata*. A series of scalable biosynthetic strategies were explored to efficiently generate kainic acid on a gram scale which strategies included enzyme total synthesis, fermentation in a heterologous host, chemoenzymatic synthesis, and biotransformation.

BRIEF DESCRIPTION OF THE DRAWINGS

FIG. 1A shows domoic acid biosynthetic pathways, in accordance with some embodiments. FIG. 1B shows kainic acid biosynthetic pathways, in accordance with some embodiments. An illustrative kainic acid biosynthesis (kab) gene cluster from *D. simplex* (FIG. 1C) and *P. palmata* are also shown. Scale bar is representative for both FIG. 1C and FIG. 1D.

FIG. 2A. High Molecular Weight (HMW) DNA was sequenced on the PromethION platform producing 47 Gb of long read sequencing data with an N50 read length of 7 kb. FIG. 2B. Nanopore sequence has an average quality score of 10. FIG. 2C. Zoomed in view of assembly graph color coded by GC % reveals *D. simplex* genome contigs (red), bacterial contigs (blue), and low, unclassified contigs (green). *D. simplex* genome contigs are clustered in a hairball due to the repeat structures in this genome. One bacterium appeared as a 6 Mb assembly. FIG. 2D. GC % by length plot reveals *D. simplex* genome and bacterial genomes.

FIG. 4A shows two-enzyme biosynthesis. FIG. 4B shows one-enzyme chemoenzymatic synthesis. FIG. 4C shows bacterial fermentation. FIG. 4D shows biotransformation. FIG. 4E shows lyophilized kainic acid in a scintillation vial Bold arrows highlight a strategy to produce large scale amounts of kainic acid.

FIG. 5 shows amino acid sequence alignment of the domoic acid DabA and kainic acid KabA proteins. The accession numbers for proteins from this study can be found in Table S3 and the Pseudo-nitzschia multiseries DabA NCBI accession number is AYD91073.1.

FIG. 6 shows amino acid sequence alignment of the domoic acid DabC and kainic acid KabC proteins. The accession numbers for proteins from this study can be found in Table S3 and the Pseudo-nitzschia multiseries DabC NCBI accession number is AYD91075.1.

FIG. 14 presents data that relates to NMR analysis of kainic acid and kainic acid lactone.

FIG. 15 shows NMR correlations for prekainic acid, kainic acid, and kainic acid lactone.

FIG. 17 shows COSY and HSQC analysis of prekainic acid (enzymatic product).

DETAILED DESCRIPTION OF THE INVENTION

Figure 3:
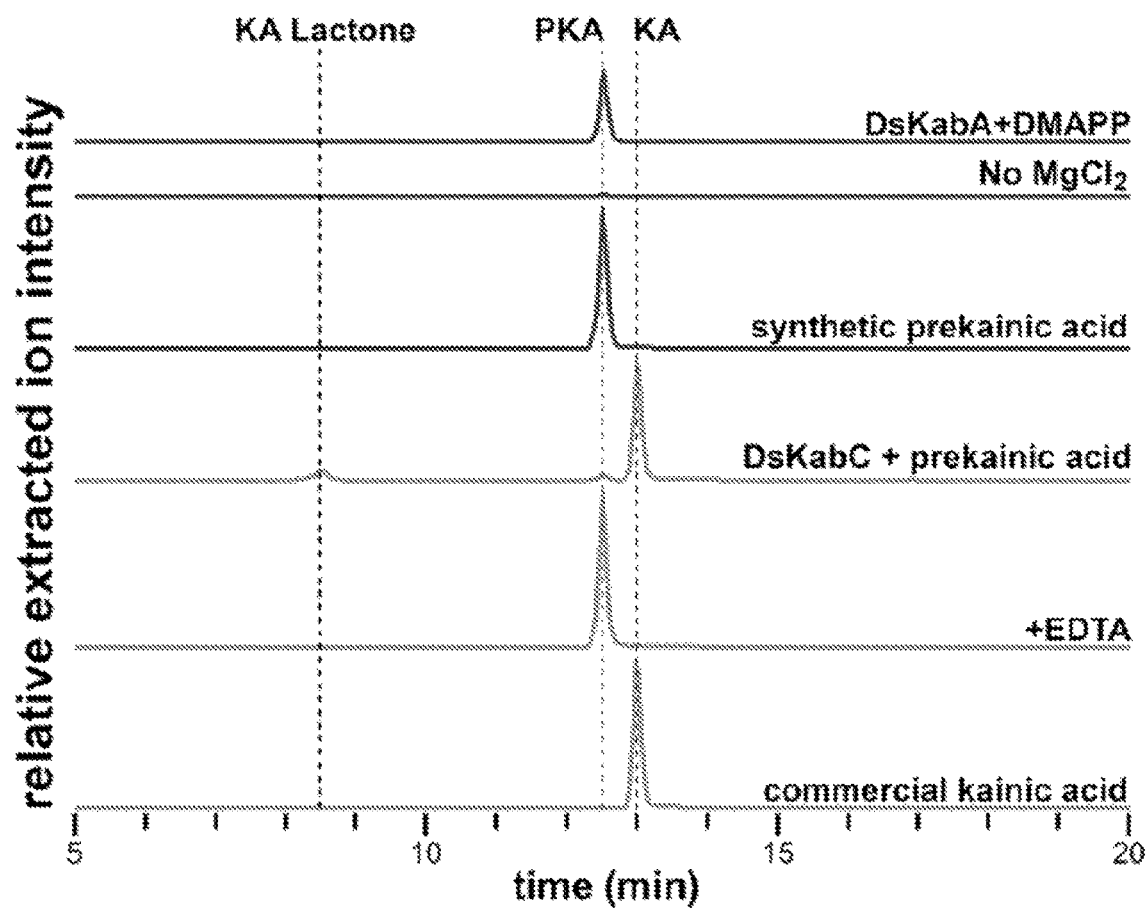
FIG. 3 shows LCMS analysis of DsKabA and DsKabC in vitro assays. Each trace represents the $(M-H)^-$ extracted ion chromatogram for prekainic acid (214.1:0.5 m/z) and kainic acid (212.1:0.5 m/z). DsKabA converts L-Glu and DMAPP to prekainic acid in a $Mg^{2+}$-dependent manner (purple traces). DsKabC can convert prekainic acid (PKA) to kainic acid (KA) and kainic acid lactone (KA Lactone), but turnover is nearly undetectable when the iron chelator EDTA is added (cyan traces).

Provided herein, inter alia, are processes for preparation of kainic acid and kainic acid lactone. In one aspect, provided herein is a process for the preparation of a compound with the formula,

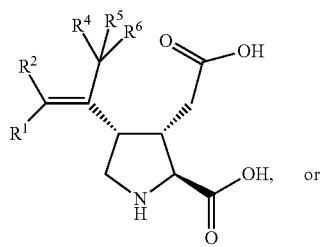

(Ia)

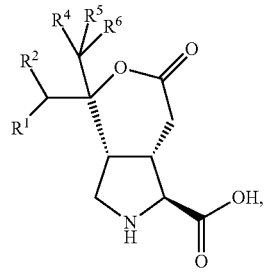

(Ib)

or a salt thereof.

The compound or a salt of Formula (Ia) or (Ib) is prepared by cyclizing a compound of formula II:

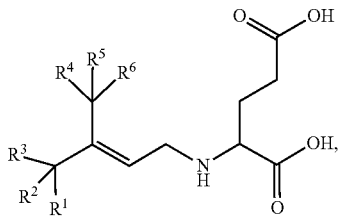

Formula II or a salt thereof.

In Formula II, (a) at least one of $R^1$, $R^2$, $R^3$, $R^4$, $R^5$ or $R^6$ is hydrogen, and (b) $R^1$ is hydrogen, halogen, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{1A}$R$^{1B}$, —OR$^{1A}$, —SR$^{1A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is hydrogen, halogen, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{2A}$R$^{2B}$, —OR$^{2A}$, —SR$^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is hydrogen, halogen, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{3A}$R$^{3B}$, —OR$^{3A}$, —SR$^{3A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ is hydrogen, halogen, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{4A}$R$^{4B}$, —OR$^{4A}$, —SR$^{4A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$ is hydrogen, halogen, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{5A}$R$^{5B}$, —OR$^{5A}$, —SR$^{5A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^6$ is hydrogen, halogen, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{6A}$R$^{6B}$, —OR$^{6A}$, —SR$^{6A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. any two of $R^1$, $R^2$ or $R^3$ substituents or any two of $R^4$, $R^5$ or $R^6$ substituents may optionally be joined to form a substituted or unsubstituted aryl or substituted or unsubstituted heteroaryl. any one of $R^1$, $R^2$ or $R^3$ and any one of $R^4$, $R^5$ or $R^6$ may optionally be joined to form a substituted or unsubstituted cycloalkyl, substituted or unsubstituted aryl or substituted or unsubstituted heteroaryl.

each $R^{1A}$, $R^{2A}$, $R^{3A}$, $R^{4A}$, $R^{5A}$, $R^{6A}$, $R^{1B}$, $R^{2B}$, $R^{3B}$, $R^{4B}$, $R^{5B}$, and $R^{6B}$ is independently a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

Cyclization of compound of Formula II is accomplished by contacting compound of Formula II with a recombinant KabC polypeptide.

In another aspect, provided herein is a process for the preparation of a compound with the formula,

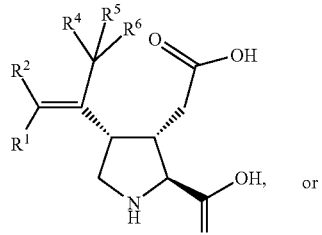

(Ia)

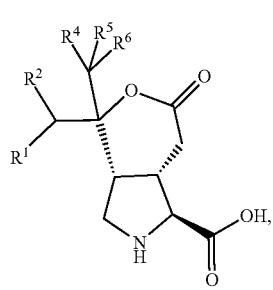

(Ib)

or a salt thereof.

The compound or a salt of Formula (Ia) or (Ib) is prepared by contacting a compound of Formula III:

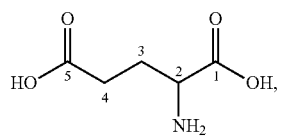

Formula III or a salt thereof, with a compound of Formula V:

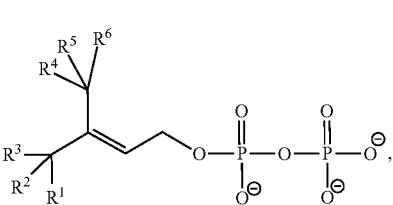

Formula V or a salt thereof, a recombinant KabA polypeptide, a recombinant KabC polypeptide, and a α-keto-glutarate.

In an aspect, provided herein is a compound of formula II:

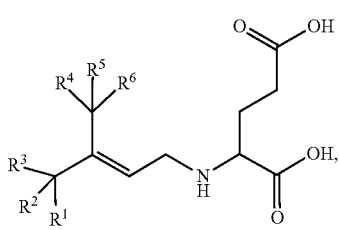

Formula II or a salt thereof.

In an aspect, provided herein is a compound of Formula VI:

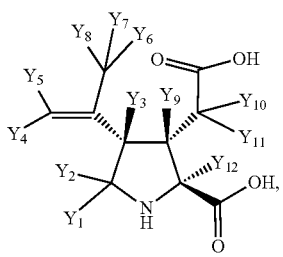

Formula VI or a salt thereof. In Formula VI, one of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ is a hydrogen that is isotopically enriched with deuterium or tritium, and the rest of $Y_1$, $Y_2$, $Y_3$, $Y_4$, $Y_5$, $Y_6$, $Y_7$, $Y_8$, $Y_9$, $Y_{10}$, $Y_{11}$, and $Y_{12}$ are non-enriched hydrogen atoms.

In an aspect, provided herein is a compound of Formula VII:

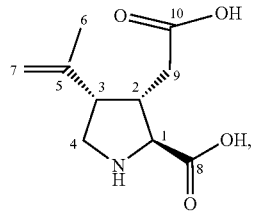

Formula VII or a salt thereof. In Formula VII, 1, 2, 3, 4, 5, 6, 7, 8, 9, and 10 are carbon atoms. At least one of 1, 2, 3, 4, 5, 6, 7, 8, 9, or 10 carbon atoms is isotopically enriched with carbon-13 or carbon-14.

In an aspect, provided herein is a compound of Formula VIII:

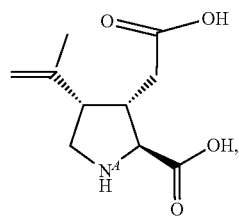

Formula VIII or a salt thereof. In Formula VIII, $N^4$ is a nitrogen atom which is isotopically enriched with nitrogen-15.

In an aspect, provided herein is a recombinant polynucleotide encoding a KabA polypeptide, a KabC polypeptide, or both.

In an aspect, provided herein is an expression vector comprising the recombinant polynucleotide.

In an aspect, provided herein is a recombinant cell which includes a polynucleotide or an expression vector.

In an aspect, provided herein is a process for the preparation of a compound with the formula,

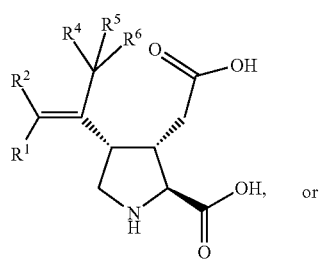

(Ia)

or

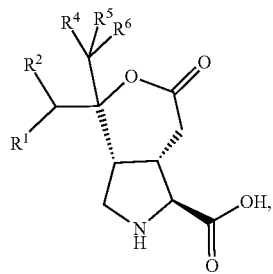

(Ib)

or a salt thereof.

In embodiments, the compound or a salt of Formula (Ia) or (Ib) is prepared by culturing a recombinant cell in a culture medium.

DETAILED DESCRIPTION

The practice of the technology described herein will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Examples of such techniques are available in the literature. Methods, devices and materials similar or equivalent to those described herein can be used in the practice of this invention.

All patents, patent applications, articles and publications mentioned herein, both supra and infra, are hereby expressly incorporated herein by reference in their entireties.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms "a", "an", and "the" include the plural reference unless the context clearly indicates otherwise.

Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein, the term "control" or "control experiment" is used in accordance with its plain and ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

As used herein, the term "complement" is used in accordance with its plain and ordinary meaning and refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (matching) nucleotide of guanosine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, sequences in a pair of complementary sequences form portions of a single polynucleotide with non-base-pairing nucleotides (e.g., as in a hairpin structure, with or without an overhang) or portions of separate polynucleotides. In embodiments, one or both sequences in a pair of complementary sequences form portions of longer polynucleotides, which may or may not include additional regions of complementarity.

As used herein, the term "contacting" is used in accordance with its plain ordinary meaning and refers to the process of allowing at least two distinct species (e.g. chemical compounds including biomolecules or cells) to become sufficiently proximal to react, interact or physically touch. However, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound, a protein or enzyme.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the TUPAC-TUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

"Nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a linear sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g. polynucleotides contemplated herein include any types of RNA, e.g. mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another:
1) Alanine (A), Glycine (G);
2) Aspartic acid (D), Glutamic acid (E);

3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

As used herein, the terms "analogue" and "analog", in reference to a chemical compound, refers to a compound having a structure similar to that of another one, but differing from it in respect of one or more different atoms, functional groups, or substructures that are replaced with one or more other atoms, functional groups, or substructures. In the context of a nucleotide, a nucleotide analog refers to a compound that, like the nucleotide of which it is an analog, can be incorporated into a nucleic acid molecule (e.g., an extension product) by a suitable polymerase, for example, a DNA polymerase in the context of a nucleotide analogue. The terms also encompass nucleic acids containing known nucleotide analogs or modified backbone residues or linkages, which are synthetic, naturally occurring, or non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, e.g., see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

As used herein, a "native" nucleotide is used in accordance with its plain and ordinary meaning and refers to a naturally occurring nucleotide that does not include an exogenous label (e.g., a fluorescent dye, or other label) or chemical modification such as may characterize a nucleotide analog. Examples of native nucleotides useful for carrying out procedures described herein include: dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate); and dUTP (2'-deoxyuridine-5'-triphosphate).

As used herein, the term "modified nucleotide" is used in accordance with its plain and ordinary meaning and refers to nucleotide modified in some manner. Typically, a nucleotide contains a single 5-carbon sugar moiety, a single nitrogenous base moiety and 1 to three phosphate moieties. In embodiments, a nucleotide can include a blocking moiety and/or a label moiety. A blocking moiety on a nucleotide prevents formation of a covalent bond between the 3' hydroxyl moiety of the nucleotide and the 5' phosphate of another nucleotide. A blocking moiety on a nucleotide can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. A label moiety of a nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both.

As used herein, the term "selective" or "selectivity" or the like of a compound refers to the compound's ability to discriminate between molecular targets.

As used herein, the terms "specific", "specifically", "specificity", or the like of a compound refers to the compound's ability to cause a particular action, such as binding, to a particular molecular target with minimal or no action to other proteins in the cell.

As used herein, the terms "bind" and "bound" are used in accordance with their plain and ordinary meanings and refer to an association between atoms or molecules. The association can be direct or indirect. For example, bound atoms or molecules may be directly bound to one another, e.g., by a covalent bond or non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). As a further example, two molecules may be bound indirectly to one another by way of direct binding to one or more intermediate molecules, thereby forming a complex.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

The terms "KabA protein" and "KabA polypeptide" refer to a protein (including homologs, isoforms, and functional fragments thereof). The term includes any recombinant or naturally-occurring form of a KabA polypeptide or variants thereof that maintain KabA polypeptide activity (e.g. within at least 30%, 40%, 50%, 60%, 70%, 80%, 90%, 95%, or 100% activity compared to wildtype KabA). In embodiments, a KabA polypeptide encoded by a kabA gene has an amino acid sequence set forth in any one of SEQ ID NOs:11-15. In embodiments, the amino acid sequence or nucleic acid sequence is the sequence known at the time of filing of the present application.

The terms "KabC protein" and "KabC polypeptide" refer to a protein (including homologs, isoforms, and functional fragments thereof). The term includes any recombinant or naturally-occurring form of a KabC polypeptide or variants thereof that maintain KabC polypeptide activity (e.g. within at least 30%, 40%, 50%, 60%, 70%, 80%, 90%, 95%, or 100% activity compared to wildtype KabC). In embodiments, a KabC polypeptide encoded by a kabC gene has an amino acid sequence set forth in any one of SEQ ID NOs:1-5. In embodiments, the kabC gene comprises a nucleic acid sequence set forth in any one of SEQ ID NOs:6-10. In embodiments, the amino acid sequence or nucleic acid sequence is the sequence known at the time of filing of the present application.

The terms "KabA gene" and "KabA polynucleotide" as used herein refer to the any of the recombinant or naturally-occurring forms of a kabA gene or variants or homologs thereof that code for a KabA polypeptide capable of maintaining the activity of a KabA polypeptide (e.g., within at least 50%, 80%, 90%, 95%, 96%, 97%, 98%, 99% or 100% activity compared to an endogenous KabA polypeptide). In some aspects, the variants or homologs have at least 90%, 95%, 96%, 97%, 98%, 99% or 100% nucleic acid sequence identity across the whole sequence or a portion of the sequence (e.g., a 50, 100, 150 or 200 continuous nucleic acid portion) compared to a naturally occurring kabA gene. In some embodiments, a KabA polynucleotide comprises a nucleotide sequence having at least 90%, 95%, 96%, 97%, 98%, 99% or 100% nucleic acid sequence identity to NCBI Accession Numbers QCC62379, QCC62384, QCC62371, QCC62373, QCC62377, or a portion thereof. In some embodiments, a KabA polynucleotide comprises a nucleotide sequence having at least 90%, 95%, 96%, 97%, 98%, 99% or 100% nucleic acid sequence identity to any one of SEQ ID NOs:16-20.

The terms "KabC gene" and "KabC polynucleotide" as used herein refer to the any of the recombinant or naturally-occurring forms of a kabC gene or variants or homologs thereof that code for a KabC polypeptide capable of maintaining the activity of a KabC polypeptide (e.g., within at least 50%, 80%, 90%, 95%, 96%, 97%, 98%, 99% or 100% activity compared to an endogenous KabC polypeptide). In some aspects, the variants or homologs have at least 90%, 95%, 96%, 97%, 98%, 99% or 100% nucleic acid sequence identity across the whole sequence or a portion of the sequence (e.g., a 50, 100, 150 or 200 continuous nucleic acid portion) compared to a naturally occurring kabC gene. In some embodiments, a KabC polynucleotide comprises a nucleotide sequence having at least 90%, 95%, 96%, 97%, 98%, 99% or 100% nucleic acid sequence identity to NCBI Accession Numbers QCC62383, QCC62385, QCC62372, QCC62374, QCC62378, or a portion thereof. In some embodiments, a KabC polynucleotide comprises a nucleotide sequence having at least 90%, 95%, 96%, 97%, 98%, 99% or 100% nucleic acid sequence identity to SEQ ID NO:33 or 34. In some embodiments, a KabC polynucleotide comprises a nucleotide sequence having at least 90%, 95%, 96%, 97%, 98%, 99% or 100% nucleic acid sequence identity to any one of SEQ ID NOs:6-10.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—S—$CH_2$, —S(O)—$CH_3$, —$CH_2$—$CH_2$—S(O)$_2$—$CH_3$, —CH=CHO—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "$\sim\!\!\sim\!\!\sim$" denotes the point of attachment of a chemical moiety to the remainder of a molecule or chemical formula.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

The term "alkylarylene" as an arylene moiety covalently bonded to an alkylene moiety (also referred to herein as an alkylene linker). In embodiments, the alkylarylene group has the formula:

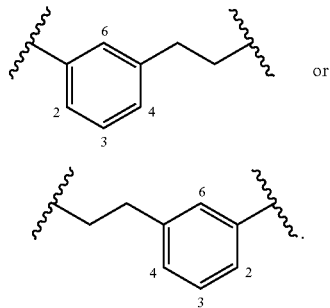

An alkylarylene moiety may be substituted (e.g. with a substituent group) on the alkylene moiety or the arylene linker (e.g. at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$— $SO_3H$, —$OSO_3H$, —$SO_2NH_2$, —$NHNH_2$, —$ONH_2$, —NHC(O)$NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C(O)NR"NR'''R'''', —CN, —NO$_2$, —NR'SO$_2$R", —NR'C(O)R", —NR'C(O)—OR", —NR'OR", in a number ranging from/zero to (2m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C(O)NR"NR'''R'''', —CN, —NO$_2$, —R', —$N_3$, —CH(Ph)$_2$, fluoro($C_1$-$C_4$)alkoxy, and fluoro($C_1$-$C_4$)alkyl, —NR'SO$_2$R", —NR'C(O)R", —NR'C(O)—OR", —NR'OR", in a number ranging from/zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R''', and R'''' groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(i) oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(a) oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, each substituted or unsubstituted heterocycloalkylene is a substituted or unsubstituted 3 to 7 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the terms "bioconjugate" and "bioconjugate linker" refers to the resulting association between atoms or molecules of "bioconjugate reactive groups" or "bioconjugate reactive moieties". The association can be direct or indirect. For example, a conjugate between a first bioconjugate reactive group (e.g., —NH2, —C(O)OH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., -sulfo-N-hydroxysuccinimide moiety) is covalently attached to the second bioconjugate reactive group (e.g. an amine).

Useful bioconjugate reactive moieties used for bioconjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido or maleimide groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold, or react with maleimides;

(h) amine or sulfhydryl groups (e.g., present in cysteine), which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(l) metal silicon oxide bonding; and (m) metal bonding to reactive phosphorus groups (e.g. phosphines) to form, for example, phosphate diester bonds.

(n) azides coupled to alkynes using copper catalyzed cycloaddition click chemistry.

(o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable agent" or "detectable moiety" is a composition detectable by appropriate means such as spectroscopic, photochemical, biochemical, immunochemical, chemical, magnetic resonance imaging, or other physical means. For example, useful detectable agents include $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{77}As$, $^{86}Y$, $^{90}Y$, $^{89}Sr$, $^{89}Zr$, $^{94}Tc$, $^{94}Tc$, $^{99m}Tc$, $^{99}Mo$, $^{105}Pd$, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154\text{-}158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorocarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154\text{-}158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$I, $^{198}$Au, $^{199}$Au, $^{211}$At, $^{211}$Pb, $^{212}$Bi, $^{212}$Pb, $^{213}$Bi, $^{223}$Ra and $^{225}$Ac. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "leaving group" is used in accordance with its ordinary meaning in chemistry and refers to a moiety (e.g., atom, functional group, molecule) that separates from the molecule following a chemical reaction (e.g., bond formation, reductive elimination, condensation, cross-coupling reaction) involving an atom or chemical moiety to which the leaving group is attached, also referred to herein as the "leaving group reactive moiety", and a complementary reactive moiety (i.e. a chemical moiety that reacts with the leaving group reactive moiety) to form a new bond between the remnants of the leaving groups reactive moiety and the complementary reactive moiety. Thus, the leaving group reactive moiety and the complementary reactive moiety form a complementary reactive group pair. Non limiting examples of leaving groups include hydrogen, hydroxide, organotin moieties (e.g., organotin heteroalkyl), halogen (e.g., Br), perfluoroalkylsulfonates (e.g. triflate), tosylates, mesylates, water, alcohols, nitrate, phosphate, thioether, amines, ammonia, fluoride, carboxylate, phenoxides, boronic acid, boronate esters, and alkoxides. In embodiments, two molecules with leaving groups are allowed to contact, and upon a reaction and/or bond formation (e.g., acyloin condensation, aldol condensation, Claisen condensation, Stille reaction) the leaving groups separates from the respective molecule. In embodiments, a leaving group is a bioconjugate reactive moiety. In embodiments, at least two leaving groups (e.g., $R^1$ and $R^{13}$) are allowed to contact such that the leaving groups are sufficiently proximal to react, interact or physically touch. In embodiments, the leaving groups is designed to facilitate the reaction.

The term "protecting group" is used in accordance with its ordinary meaning in organic chemistry and refers to a moiety covalently bound to a heteroatom, heterocycloalkyl, or heteroaryl to prevent reactivity of the heteroatom, heterocycloalkyl, or heteroaryl during one or more chemical reactions performed prior to removal of the protecting group. Typically a protecting group is bound to a heteroatom (e.g., O) during a part of a multipart synthesis wherein it is not desired to have the heteroatom react (e.g., a chemical reduction) with the reagent. Following protection the protecting group may be removed (e.g., by modulating the pH). In embodiments the protecting group is an alcohol protecting group. Non-limiting examples of alcohol protecting groups include acetyl, benzoyl, benzyl, methoxymethyl ether (MOM), tetrahydropyranyl (THP), and silyl ether (e.g., trimethylsilyl (TMS)). In embodiments the protecting group is an amine protecting group. Non-limiting examples of amine protecting groups include carbobenzyloxy (Cbz), tert-butyloxycarbonyl (BOC), 9-Fluorenylmethyloxycarbonyl (FMOC), acetyl, benzoyl, benzyl, carbamate, p-methoxybenzyl ether (PMB), and tosyl (Ts).

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or —$CH_3$). Likewise, for a linker variable (e.g., $L^1$, $L^2$, or $L^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

The term "exogenous" refers to a molecule or substance (e.g., a compound, nucleic acid or protein) that originates from outside a given cell or organism. For example, an "exogenous promoter" as referred to herein is a promoter that does not originate from the plant it is expressed by. Conversely, the term "endogenous" or "endogenous promoter" refers to a molecule or substance that is native to, or originates within, a given cell or organism.

The term "lipid moiety" is used in accordance with its ordinary meaning in chemistry and refers to a hydrophobic molecule which is typically characterized by an aliphatic hydrocarbon chain. In embodiments, the lipid moiety includes a carbon chain of 3 to 100 carbons. In embodiments, the lipid moiety includes a carbon chain of 5 to 50 carbons. In embodiments, the lipid moiety includes a carbon chain of 5 to 25 carbons. In embodiments, the lipid moiety includes a carbon chain of 8 to 525 carbons. Lipid moieties may include saturated or unsaturated carbon chains, and may be optionally substituted. In embodiments, the lipid moiety is optionally substituted with a charged moiety at the terminal end. In embodiments, the lipid moiety is an alkyl or heteroalkyl optionally substituted with a carboxylic acid moiety at the terminal end.

A charged moiety refers to a functional group possessing an abundance of electron density (i.e. electronegative) or is deficient in electron density (i.e. electropositive). Non-limiting examples of a charged moiety includes carboxylic acid, alcohol, phosphate, aldehyde, and sulfonamide. In embodiments, a charged moiety is capable of forming hydrogen bonds.

The term "coupling reagent" is used in accordance with its plain ordinary meaning in the arts and refers to a substance (e.g., a compound or solution) which participates in chemical reaction and results in the formation of a covalent bond (e.g., between bioconjugate reactive moieties, between a bioconjugate reactive moiety and the coupling reagent). In embodiments, the level of reagent is depleted in the course of a chemical reaction. This is in contrast to a solvent, which typically does not get consumed over the course of the chemical reaction. Non-limiting examples of coupling reagents include benzotriazol-1-yl-oxytripyrrolidinophosphonium hexafluorophosphate (PyBOP), 7-Azabenzotriazol-1-yloxy)tripyrrolidinophosphonium hexafluorophosphate (PyAOP), 6-Chloro-benzotriazole-1-yloxy-trispyrrolidinophosphonium hexafluorophosphate (PyClock), 1-[Bis(dimethylamino)methylene]-1H-1,2,3-triazolo[4,5-b]pyridinium 3-oxid hexafluorophosphate (HATU), or 2-(1H-benzotriazol-1-yl)-1,1,3,3-tetramethyluronium hexafluorophosphate (HBTU).

The term "solution" is used in accor and refers to a liquid mixture in which the minor component (e.g., a solute or compound) is uniformly distributed within the major component (e.g., a solvent).

The term "organic solvent" as used herein is used in accordance with its ordinary meaning in chemistry and refers to a solvent which includes carbon. Non-limiting examples of organic solvents include acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme (diethylene glycol, dimethyl ether), 1,2-dimethoxyethane (glyme, DME), dimethylformamide (DMF), dimethyl sulfoxide (DMSO), 1,4-dioxane, ethanol, ethyl acetate, ethylene glycol, glycerin, heptane, hexamethylphosphoramide (HMPA), hexamethylphosphorous, triamide (HMPT), hexane, methanol, methyl t-butyl ether (MTBE), methylene chloride, N-methyl-2-pyrrolidinone (NMP), nitromethane, pentane, petroleum ether (ligroine), 1-propanol, 2-propanol, pyridine, tetrahydrofuran (THF), toluene, triethyl amine, o-xylene, m-xylene, or p-xylene. In embodiments, the organic solvent is or includes chloroform, dichloromethane, methanol, ethanol, tetrahydrofuran, or dioxane.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The terms "bind" and "bound" as used herein is used in accordance with its plain and ordinary meaning and refers to the association between atoms or molecules. The association can be direct or indirect. For example, bound atoms or molecules may be direct, e.g., by covalent bond or linker (e.g. a first linker or second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like).

The term "capable of binding" as used herein refers to a moiety (e.g. a compound as described herein) that is able to measurably bind to a target (e.g., a NF-κB, a Toll-like receptor protein). In embodiments, where a moiety is capable of binding a target, the moiety is capable of binding with a Kd of less than about 10 μM, 5 μM, 1 μM, 500 nM, 250 nM, 100 nM, 75 nM, 50 nM, 25 nM, 15 nM, 10 nM, 5 nM, 1 nM, or about 0.1 nM.

As used herein, the term "conjugated" when referring to two moieties means the two moieties are bonded, wherein the bond or bonds connecting the two moieties may be covalent or non-covalent. In embodiments, the two moieties are covalently bonded to each other (e.g. directly or through a covalently bonded intermediary). In embodiments, the two moieties are non-covalently bonded (e.g. through ionic bond(s), van der waal's bond(s)/interactions, hydrogen bond(s), polar bond(s), or combinations or mixtures thereof).

The term "non-nucleophilic base" as used herein refers to any sterically hindered base that is a poor nucleophile.

The term "nucleophile" as used herein refers to a chemical species that donates an electron pair to an electrophile to form a chemical bond in relation to a reaction. All molecules or ions with a free pair of electrons or at least one pi bond can act as nucleophiles.

The term "strong acid" as used herein refers to an acid that is completely dissociated or ionized in an aqueous solution. Examples of common strong acids include hydrochloric acid (HCl), nitric acid ($HNO_3$), sulfuric acid ($H_2SO_4$), hydrobromic acid (HBr), hydroiodic acid (HI), perchloric acid ($HClO_4$), or chloric acid ($HClO_3$).

The term "carbocation stabilizing solvent" as used herein refers to any polar protic solvent capable of forming dipole-dipole interactions with a carbocation, thereby stabilizing the carbocation.

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed within the invention. The upper and lower limits of any such smaller range (within a more broadly recited range) may independently be included in the smaller ranges, or as particular values themselves, and are also encompassed within the invention, subject to any specifically excluded limit in the stated range. Where the stated range includes one or both of the limits, ranges excluding either or both of those included limits are also included in the invention.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Kainic acid, the flagship member of the kainoid family of natural neurochemicals, is a widely used neuropharmacology agent that helped unravel the key role of ionotropic glutamate receptors, including the kainate receptor, in the central nervous system. Worldwide shortages of this seaweed natural product in 2000 prompted numerous chemical syntheses that now number in excess of 70, including scalable preparations with as few as six-steps. Recently, the biosynthesis of the kainoid domoic acid was established in Pseudo-nitzschia diatoms that revealed nature's molecular logic in efficiently constructing their shared pyrrolidine ring with three contiguous stereogenic centers.

The tropical seaweed *Digenea simplex* has been used for centuries in Asia as an antihelmenthic agent to treat parasitic worm infections[1]. In the 1950s, the active compound, kainic acid, was isolated[2,3], enabling its use as a combination treatment for *Ascaris* infections up until the 1990s[4]-6. While the exact antihelmenthic mechanism of action remains unclear, kainic acid functions as an ionotropic glutamate receptor (iGluR) agonist[7]. iGluRs mediate neuronal cell-cell commutation by binding to glutamate and facilitating influx of $Ca^{2+}$ into the cell[8]. Structurally similar to glutamic acid, kainic acid can bind more efficiently to iGluRs and thereby stimulate excessive influx of $Ca^{2+}$, which leads to excitotoxicity and cell death9. In fact, kainic acid was important in the initial discovery and characterization of several classes of iGluRs, particularly the eponymous kainate receptor[10]. The iGluR agonistic bioactivity is shared with the other members of the kainoid natural product family, namely domoic acid[11] and acromelic acid[12]. Notably, domoic acid is a major environmental toxin produced primarily by oceanic diatom blooms[13,14] and causes severe neurological problems when consumed through contaminated seafood[15,16]. While kainic acid does not appear to produce excitotoxic effects for humans in vivo, its bioactivity has been exploited to create mouse model systems to study neurological diseases17, particularly temporal lobe epilepsy[18,19].

Even though kainic acid was discovered more than 50 years ago and over 70 synthetic routes have been established[20], there has been little progress made on elucidating how it is constructed by seaweeds. In fact, although red macroalgae are prolific producers of natural products, with over 700 compounds identified, only five genomes are currently available, which has curtailed biosynthetic discovery science in algae through modern genome mining approaches[21]. Recently, we established the biosynthetic logic for domoic acid production in microalgal Pseudo-nitzschia multiseries diatoms through the discovery of a four-gene cassette (dabA-D) and the confirmation of their in vitro enzymatic functions[22]. The structural similarity between domoic acid and kainic acid allowed us to propose a conserved route of biosynthesis (FIG. 1A). N-prenylation of L-glutamate with dimethylallyl pyrophosphate (DMAPP) via a DabA homolog would produce a "prekainic acid" pathway intermediate that could conceivably be directly cyclized with a DabC homolog to generate kainic acid. Using a genomics approach, we identified red macroalgal kainic acid gene clusters and leveraged these newly identified enzymes to develop in vitro and in vivo kainic acid production routes. Together, our results demonstrate the advantages of new sequencing technologies to discover biosynthesis genes from challenging eukaryotic genomes and further reinforce the utility of enzymes in the manufacturing of fine chemicals.

In one aspect, provided herein is a process for the preparation of a compound with the formula,

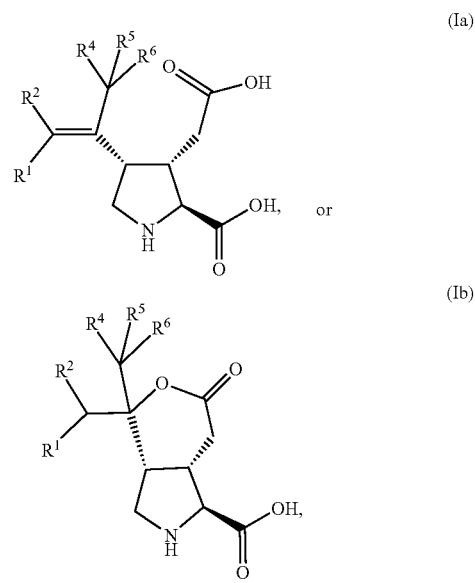

or a salt thereof.

The compound or a salt of Formula (Ia) or (Ib) is prepared by cyclizing a compound of formula II.

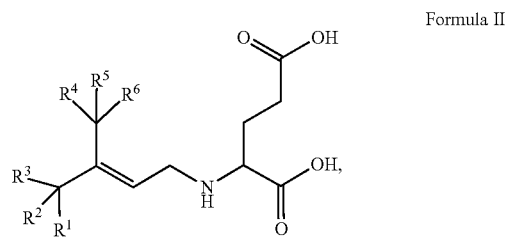

or a salt thereof.

In Formula II, (a) at least one of $R^1$, $R^2$, $R^3$, $R^4$, $R^5$ or $R^6$ is hydrogen, and (b) $R^1$ is hydrogen, halogen, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{1A}$R$^{1B}$, —OR$^{1A}$, —SR$^{1A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is hydrogen, halogen, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{2A}$R$^{2B}$, —OR$^{2A}$, —SR$^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is hydrogen, halogen, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{3A}$R$^{3B}$, —OR$^{3A}$, —SR$^{3A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ is hydrogen, halogen, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{4A}$R$^{4B}$, —OR$^{4A}$, —SR$^{4A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$ is hydrogen, halogen, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{5A}$R$^{5B}$, —OR$^{5A}$, —SR$^{5A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^6$ is hydrogen, halogen, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{6A}$R$^{6B}$, —OR$^{6A}$, —SR$^{6A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^1$ and $R^2$ may optionally be joined to form an oxo. Any two of $R^1$, $R^2$ or $R^3$ substituents or any two of $R^4$, $R^5$ or $R^6$ substituents may optionally be joined to form a substituted or unsubstituted aryl or substituted or unsubstituted heteroaryl. Any one of $R^1$, $R^2$ or $R^3$ and any one of $R^4$, $R^5$ or $R^6$ may optionally be joined to form a substituted or unsubstituted cycloalkyl, substituted or unsubstituted aryl or substituted or unsubstituted heteroaryl. Each $R^{1A}$, $R^{2A}$, $R^{3A}$, $R^{4A}$, $R^{5A}$, $R^{6A}$, $R^{1B}$, $R^{2B}$, $R^{3B}$, $R^{4B}$, $R^{5B}$, and $R^{6B}$ is independently a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, the cyclization of compound of Formula II is accomplished by contacting compound of Formula II with a recombinant KabC polypeptide. In embodiments, the cyclization of compound of Formula II is accomplished by contacting compound of Formula II with a purified KabC polypeptide and a α-keto-glutarate.

In embodiments, the process for the preparation of compound having the formula (Ia) or (Ib) includes the incubation of *D. simplex* KabC (DsKabC), compound of Formula II (prekainic acid), α-keto-glutarate, L-ascorbate and ferrous iron.

Particular process conditions, including one or more of reaction time, temperature, solvent, reagent, amount of reagent(s) order of reagent addition, pH etc. may be selected in order to optimize reaction product purity and/or yield.

In embodiments, ferrous iron is ferrous hydroxide, ferrous halide, ferrous nitrate, ferrous sulfate, ferrous oxide, ferrous carbonate, ferrous acetate, ferrous chromate. In embodiments, ferrous iron is ferrous sulfate.

In embodiments, the incubation is carried out in a buffer at pH of about 5.0, about 5.5, about 6.0, about 6.5, about 7.0, about 7.5, about 8.0, about 8.5, about 9.0, about 9.5, or about 10.0. In embodiments, the incubation is carried out in a buffer of 300 mM potassium chloride and 50 mM HEPES pH 8.0.

In embodiments, the incubation is carried out at about 5° C., about 10° C., about 15° C., about 20° C., about 25° C., about 30° C., about 35° C., about 40° C., or about 45° C. In embodiments, the incubation is carried out at about 22° C. In embodiments, the incubation is carried out for about 5 hours, about 10 hours, about 15 hours, about 20 hours, about 25 hours, about 30 hours, about 35 hours, about 40 hours, or about 45 hours. In embodiments, the incubation is carried out for about 18 hours.

In embodiments, (a) at least one of $R^1$, $R^2$, $R^3$, $R^4$, $R^5$ or $R^6$ in Formula II is a hydrogen, and (b) $R^1$ is hydrogen, substituted or unsubstituted $C_1$-$C_{10}$ alkyl, substituted or unsubstituted $C_5$-$C_{10}$ aryl, or substituted or unsubstituted 5 to 10 membered heteroaryl. $R^2$ is hydrogen, substituted or unsubstituted $C_1$-$C_{10}$ alkyl, substituted or unsubstituted $C_5$-$C_{10}$ aryl, or substituted or unsubstituted 5 to 10 membered heteroaryl. $R_3$ is hydrogen, substituted or unsubstituted $C_1$-$C_{10}$ alkyl, substituted or unsubstituted $C_5$-$C_{10}$ aryl, or substituted or unsubstituted 5 to 10 membered heteroaryl. $R^4$ is hydrogen, substituted or unsubstituted $C_1$-$C_{10}$ alkyl, substituted or unsubstituted $C_5$-$C_{10}$ aryl, or substituted or unsubstituted 5 to 10 membered heteroaryl. $R^5$ is hydrogen, substituted or unsubstituted $C_1$-$C_{10}$ alkyl, substituted or unsubstituted $C_5$-$C_{10}$ aryl, or substituted or unsubstituted 5 to 10 membered heteroaryl. $R^6$ is hydrogen, substituted or unsubstituted $C_1$-$C_{10}$ alkyl, substituted or unsubstituted $C_5$-$C_{10}$ aryl, or substituted or unsubstituted 5 to 10 membered heteroaryl. any two of $R^1$, $R^2$ or $R^3$ substituents or any two of $R^4$, $R^5$ or $R^6$ substituents may optionally be joined to form a substituted or unsubstituted $C_5$-$C_{10}$ aryl or substituted or unsubstituted 5 to 10 membered heteroaryl. Any one of $R^1$, $R^2$ or $R^3$ and any one of $R^4$, $R^5$ or $R^6$ may optionally be joined to form a substituted or unsubstituted $C_3$-$C_8$ cycloalkyl, substituted or unsubstituted $C_5$-$C_{10}$ aryl or substituted or unsubstituted 5 to 10 membered heteroaryl.

In embodiments, (a) at least one of $R^1$, $R^2$, $R^3$, $R^4$, $R^5$ or $R^6$ in Formula II is a hydrogen, and (b) $R^1$ is hydrogen or substituted or unsubstituted $C_1$-$C_{10}$ alkyl. $R^2$ is hydrogen or substituted or unsubstituted $C_1$-$C_{10}$ alkyl. $R^3$ is hydrogen or substituted or unsubstituted $C_1$-$C_{10}$ alkyl. $R^4$ is hydrogen or substituted or unsubstituted $C_1$-$C_{10}$ alkyl. $R^5$ is hydrogen or substituted or unsubstituted $C_1$-$C_{10}$ alkyl. $R^6$ is hydrogen or substituted or unsubstituted $C_1$-$C_{10}$ alkyl. any two of $R^1$, $R^2$ or $R^3$ substituents or any two of $R^4$, $R^5$ or $R^6$ substituents may optionally be joined to form a substituted or unsubstituted $C_5$-$C_{10}$ aryl or substituted or unsubstituted 5 to 10 membered heteroaryl. Any one of $R^1$, $R^2$ or $R^3$ and any one of $R^4$, $R^5$ or $R^6$ may optionally be joined to form a substituted or unsubstituted $C_3$-$C_8$ cycloalkyl, substituted or unsubstituted $C_5$-$C_{10}$ aryl or substituted or unsubstituted 5 to 10 membered heteroaryl.

In embodiments, $R^1$, $R^2$, $R^3$, $R^4$, $R^5$ and $R^6$ are hydrogen.

In embodiments, $R^1$ is hydrogen, halogen, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{1A}$R$^{1B}$, —OR$^{1A}$, —SR$^{1A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^1$ is hydrogen, halogen, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{1A}$R$^{1B}$, —OR$^{1A}$, —SR$^{1A}$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, where $R^1$ is substituted, $R^1$ is substituted with a substituent group. In embodiments, where $R^1$ is substituted, $R^1$ is substituted with a size-limited substituent group. In embodiments, where $R^1$ is substituted, $R^1$ is substituted with a lower substituent group.

In embodiments, $R^{1A}$ is independently hydrogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{1A}$ is independently hydrogen or substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl).

In embodiments, $R^{1A}$ is independently hydrogen.

In embodiments, $R''$ is independently hydrogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{1B}$ is independently hydrogen or substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl).

In embodiments, $R^{1B}$ is independently hydrogen.

In embodiments, $R^2$ is hydrogen, halogen, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{2A}$R$^{2B}$, —OR$^{2A}$, —SR$^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^2$ is hydrogen, halogen, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{1A}$R$^{1B}$, —OR$^{1A}$, —SR$^{1A}$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, where $R^2$ is substituted, $R^2$ is substituted with a substituent group. In embodiments, where $R^2$ is substituted, $R^2$ is substituted with a size-limited substituent group. In embodiments, where $R^2$ is substituted, $R^2$ is substituted with a lower substituent group.

In embodiments, $R^{2A}$ is independently hydrogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{2A}$ is independently hydrogen or substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl).

In embodiments, $R^{2A}$ is independently hydrogen.

In embodiments, $R^{2B}$ is independently hydrogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{2B}$ is independently hydrogen or substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl).

In embodiments, $R^{2B}$ is independently hydrogen.

In embodiments, $R^3$ is hydrogen, halogen, —CN, —C(O)OH, —$CONH_2$, —$NO_2$, —$SO_2Cl$, —$SO_2NH_2$, —$NHNH_2$, —$NHSO_2CH_3$, —$N_3$, —$NR^{2A}R^{2B}$, —$OR^{2A}$, —$SR^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^3$ is hydrogen, halogen, —CN, —C(O)OH, —$CONH_2$, —$NO_2$, —$SO_2Cl$, —$SO_2NH_2$, —$NHNH_2$, —$NHSO_2CH_3$, —$N_3$, —$NR^{1A}R^{1B}$, —$OR^{1A}$, —$SR^{1A}$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, where $R^3$ is substituted, $R^3$ is substituted with a substituent group. In embodiments, where $R^3$ is substituted, $R^3$ is substituted with a size-limited substituent group. In embodiments, where $R^3$ is substituted, $R^3$ is substituted with a lower substituent group.

In embodiments, $R^{3A}$ is independently hydrogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{3A}$ is independently hydrogen or substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl).

In embodiments, $R^{3A}$ is independently hydrogen.

In embodiments, $R^{3B}$ is independently hydrogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{3B}$ is independently hydrogen or substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl).

In embodiments, $R^{3B}$ is independently hydrogen.

In embodiments, $R^4$ is hydrogen, halogen, $-CN$, $-C(O)OH$, $-CONH_2$, $-NO_2$, $-SO_2Cl$, $-SO_2NH_2$, $-NHNH_2$, $-NHSO_2CH_3$, $-N_3$, $-NR^{2A}R^{2B}$, $-OR^{2A}$, $-SR^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^4$ is hydrogen, halogen, $-CN$, $-C(O)OH$, $-CONH_2$, $-NO_2$, $-SO_2Cl$, $-SO_2NH_2$, $-NHNH_2$, $-NHSO_2CH_3$, $-N_3$, $-NR^{1A}R^{1B}$, $-OR^{1A}$, $-SR^{1A}$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, where $R^4$ is substituted, $R^4$ is substituted with a substituent group. In embodiments, where $R^4$ is substituted, $R^4$ is substituted with a size-limited substituent group. In embodiments, where $R^4$ is substituted, $R^4$ is substituted with a lower substituent group.

In embodiments, $R^{4A}$ is independently hydrogen, $-CCl_3$, $-CBr_3$, $-CF_3$, $-CI_3$, $-CH_2Cl$, $-CH_2Br$, $-CH_2F$, $-CH_2I$, $-CHCl_2$, $-CHBr_2$, $-CHF_2$, $-CHI_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCBr_3$, $-OCF_3$, $-OCI_3$, $-OCH_2Cl$, $-OCH_2Br$, $-OCH_2F$, $-OCH_2I$, $-OCHCl_2$, $-OCHBr_2$, $-OCHF_2$, $-OCHI_2$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{4A}$ is independently hydrogen or substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl).

In embodiments, $R^{4A}$ is independently hydrogen.

In embodiments, $R^{4B}$ is independently hydrogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{4B}$ is independently hydrogen or substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl).

In embodiments, $R^{4B}$ is independently hydrogen.

In embodiments, $R^5$ is hydrogen, halogen, —CN, —C(O)OH, —$CONH_2$, —$NO_2$, —$SO_2Cl$, —$SO_2NH_2$, —$NHNH_2$, —$NHSO_2CH_3$, —$N_3$, —$NR^{2A}R^{2B}$, —$OR^{2A}$, —$SR^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^5$ is hydrogen, halogen, —CN, —C(O)OH, —$CONH_2$, —$NO_2$, —$SO_2Cl$, —$SO_2NH_2$, —$NHNH_2$, —$NHSO_2CH_3$, —$N_3$, —$NR^{1A}R^{1B}$, —$OR^{1A}$, —$SR^{1A}$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, where $R^5$ is substituted, $R^5$ is substituted with a substituent group. In embodiments, where $R^5$ is substituted, $R^5$ is substituted with a size-limited substituent group. In embodiments, where $R^5$ is substituted, $R^5$ is substituted with a lower substituent group.

In embodiments, $R^{5A}$ is independently hydrogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{5A}$ is independently hydrogen or substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl).

In embodiments, $R^{5A}$ is independently hydrogen.

In embodiments, $R^{5B}$ is independently hydrogen, —$CCl_3$, —$CBr_3$, —$CF_3$, —$CI_3$, —$CH_2Cl$, —$CH_2Br$, —$CH_2F$, —$CH_2I$, —$CHCl_2$, —$CHBr_2$, —$CHF_2$, —$CHI_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCBr_3$, —$OCF_3$, —$OCI_3$, —$OCH_2Cl$, —$OCH_2Br$, —$OCH_2F$, —$OCH_2I$, —$OCHCl_2$, —$OCHBr_2$, —$OCHF_2$, —$OCHI_2$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{5B}$ is independently hydrogen or substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl).

In embodiments, $R^{5B}$ is independently hydrogen.

In embodiments, $R^6$ is hydrogen, halogen, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{2A}$R$^{2B}$, —OR$^{2A}$, —SR$^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^6$ is hydrogen, halogen, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{1A}$R$^{1B}$, —OR$^{1A}$, —SR$^{1A}$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, where $R^6$ is substituted, $R^6$ is substituted with a substituent group. In embodiments, where $R^6$ is substituted, $R^6$ is substituted with a size-limited substituent group. In embodiments, where $R^6$ is substituted, $R^6$ is substituted with a lower substituent group.

In embodiments, $R^{6A}$ is independently hydrogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{6A}$ is independently hydrogen or substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl).

In embodiments, $R^{6A}$ is independently hydrogen.

In embodiments, $R^{6B}$ is independently hydrogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCBr$_3$, —OCF$_3$, —OCI$_3$, —OCH$_2$Cl, —OCH$_2$Br, —OCH$_2$F, —OCH$_2$I, —OCHCl$_2$, —OCHBr$_2$, —OCHF$_2$, —OCHI$_2$, substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl), substituted (e.g. with a substituent group, a size-limited substituent group or a lower substituent group) or unsubstituted heteroalkyl (e.g., 2 to 8 membered heteroalkyl, 2 to 6 membered heteroalkyl, or 2 to 4 membered heteroalkyl), substituted (e.g. with a substituent group, a size-limited substituent group or a lower substituent group) or unsubstituted cycloalkyl (e.g., $C_3$-$C_8$ cycloalkyl, $C_3$-$C_6$ cycloalkyl, or $C_5$-$C_6$ cycloalkyl), substituted (e.g. with a substituent group, a size-limited substituent group or a lower substituent group) or unsubstituted heterocycloalkyl (e.g., 3 to 8 membered heterocycloalkyl, 3 to 6 membered heterocycloalkyl, or 5 to 6 membered heterocycloalkyl), substituted (e.g. with a substituent group, a size-limited substituent group or a lower substituent group) or unsubstituted aryl (e.g., $C_6$-$C_{10}$ aryl, $C_{10}$ aryl, or phenyl), or substituted (e.g. with a substituent group, a size-limited substituent group or a lower substituent group) or unsubstituted heteroaryl (e.g., 5 to 10 membered heteroaryl, 5 to 9 membered heteroaryl, or 5 to 6 membered heteroaryl).

In embodiments, $R^{6B}$ is independently hydrogen or substituted (e.g. with a substituent group, a size-limited substituent group or a lower substituent group) or unsubstituted alkyl (e.g., $C_1$-$C_8$ alkyl, $C_1$-$C_6$ alkyl, or $C_1$-$C_4$ alkyl).

In embodiments, $R^{6B}$ is independently hydrogen.

In embodiments, provided herein is a process for the preparation of compound of Formula II, or a salt thereof. In embodiments, the preparation of compound of Formula II, or a salt thereof, includes (a) contacting a compound of Formula III:

Formula III

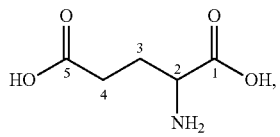

or a salt thereof, with a compound of Formula IV:

Formula IV

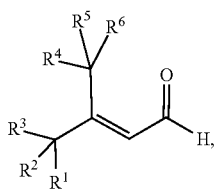

or a salt thereof, to form an imine; and (b) reducing the imine to produce the compound of Formula II. $R^1$, $R^2$, $R^3$, $R^4$, $R^5$, and $R^6$ are as described herein, including embodiments.

In embodiments, the process for the preparation of compound of Formula II (prekainic acid), or a salt thereof, includes the incubation of compound of Formula III (glutamic acid) with compound of Formula IV (3-methyl-2-butenal).

Particular process conditions, including one or more of reaction time, temperature, solvent, reagent, amount of reagent(s) order of reagent addition, pH etc. may be selected in order to optimize reaction product purity and/or yield.

In embodiments, compound of Formula III is in an aqueous solution. In embodiments, a base is added to aqueous solution of compound of Formula III. In embodiments, the base is lithium hydroxide, sodium hydroxide, potassium hydroxide, rubidium hydroxide, cesium hydroxide, calcium hydroxide, strontium hydroxide, or barium hydroxide. In embodiments the base is sodium hydroxide.

In embodiments, compound of Formula IV is added to the basic aqueous solution of compound of Formula III. In embodiments, the incubation is carried out for about 1 minute, 5 minutes, about 10 minutes, about 15, minutes, about 20 minutes, about 25 minutes, about 30 minutes, about 40 minutes, about 50 minutes, or about 60 minutes. In embodiments, the incubation is carried out at about −10° C., about −5° C., about 0° C., about 5° C., about 10° C., about 15° C., or about 20° C.

In embodiments, following the incubation of compound of Formula IV with basic aqueous solution of compound of Formula III the formed imine is reduced with a base. In embodiments, the imine reducing base is a metal borohydride. In embodiments, the metal borohydride is lithium borohydride, zinc borohydride or sodium borohydride. In embodiments, the imine reducing base is sodium borohydride, lithium borohydride, zinc borohydride, sodium cyanoborohydride, sodium tri-acetoxyborohydride or lithium aluminum hydride.

In another aspect, provided herein is a process for the preparation of a compound with the formula,

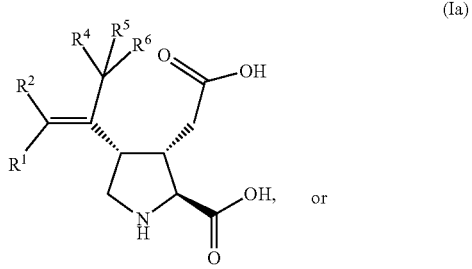

(Ia)

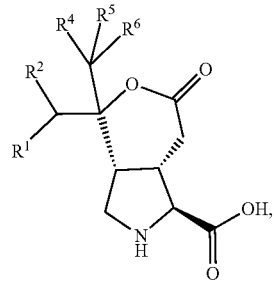

(Ib)

or a salt thereof. $R^1$, $R^2$, $R^3$, $R^4$, $R^5$, and $R^6$ are as described herein, including embodiments.

The compound or a salt of Formula (Ia) or (Ib) is prepared by contacting a compound of Formula III:

Formula III

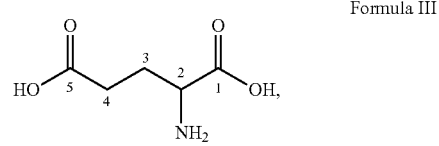

or a salt thereof, with a compound of Formula V:

Formula V

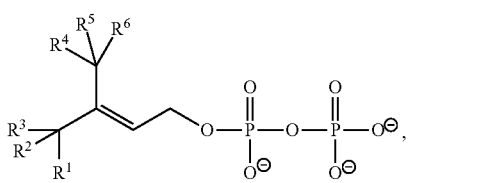

or a salt thereof, a recombinant KabA polypeptide, a recombinant KabC polypeptide, and a α-keto-glutarate. $R^1$, $R^2$, $R^3$, $R^4$, $R^5$, and $R^6$ are as described herein, including embodiments.

In embodiments, compound of Formula II, or a salt thereof, is prepared by contacting a compound of Formula III:

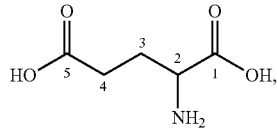

Formula III or a salt thereof, with a compound of Formula V:

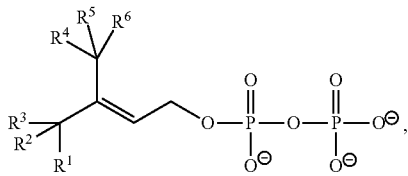

Formula V or a salt thereof, and a recombinant KabA polypeptide. $R^1$, $R^2$, $R^3$, $R^4$, $R^5$, and $R^6$ are as described herein, including embodiments.

In embodiments, the process for the preparation of compound of Formula (Ia) or (Ib), or a salt thereof, includes the incubation of compound of Formula III (glutamic acid) with compound of Formula V (DMAPP), *D. simplex* KabC (DsKabC), *D. simplex* KabA (DsKabA), α-keto-glutarate, L-ascorbate, $Mg^{+2}$ cofactor, and ferrous iron.

Particular process conditions, including one or more of reaction time, temperature, solvent, reagent, amount of reagent(s) order of reagent addition, pH etc. may be selected in order to optimize reaction product purity and/or yield.

In embodiments, ferrous iron is ferrous hydroxide, ferrous halide, ferrous nitrate, ferrous sulfate, ferrous oxide, ferrous carbonate, ferrous acetate, ferrous chromate. In embodiments, ferrous iron is ferrous sulfate.

In embodiments, $Mg^{+2}$ cofactor is magnesium halide, magnesium sulfate, magnesium nitrate, magnesium carbonate, or magnesium acetate. In embodiments, $Mg^{+2}$ cofactor is magnesium halide. In embodiments, $Mg^{+2}$ cofactor is magnesium chloride.

In embodiments, the incubation is carried out in a buffer at pH of about 5.0, about 5.5, about 6.0, about 6.5, about 7.0, about 7.5, about 8.0, about 8.5, about 9.0, about 9.5, or about 10.0. In embodiments, the incubation is carried out in a buffer of 300 mM potassium chloride and 50 mM HEPES pH 8.0. In embodiments, the incubation is carried out at about 5° C., about 10° C., about 15° C., about 20° C., about 25° C., about 30° C., about 35° C., about 40° C., or about 45° C. In embodiments, the incubation is carried out at about 22° C. In embodiments, the incubation is carried out for about 5 hours, about 10 hours, about 15 hours, about 20 hours, about 25 hours, about 30 hours, about 35 hours, about 40 hours, or about 45 hours. In embodiments, the incubation is carried out for about 18 hours.

In an aspect, provided herein is a compound of formula II:

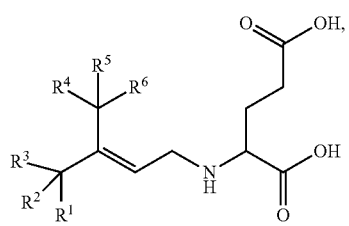

Formula II or a salt thereof. $R^1$, $R^2$, $R^3$, $R^4$, $R^5$, and $R^6$ are as described herein, including embodiments.

In an aspect, provided herein is a compound of formula VI:

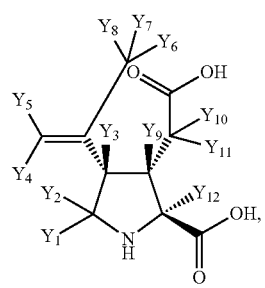

Formula VI or a salt thereof. In Formula VI, one of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ is a hydrogen that is isotopically enriched with deuterium or tritium. In embodiments, one of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ is a hydrogen that is isotopically enriched with deuterium. one of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ is a hydrogen that is isotopically enriched with tritium.

In embodiments, any two of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with deuterium or tritium. In embodiments, any three of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with deuterium or tritium. In embodiments, any four of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with deuterium or tritium. In embodiments, any five of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with deuterium or tritium. In embodiments, any six of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with deuterium or tritium. In embodiments, any seven of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with deuterium or tritium. In embodiments, any eight of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with deuterium or tritium. In embodiments, any nine of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with deuterium or tritium. In embodiments, any ten of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with deuterium or tritium. In embodiments, any eleven of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with deuterium or tritium. In embodiments, all of $Y_1$, $Y_2$, $Y_3$, $Y_4$, $Y_5$, $Y_6$, $Y_7$, $Y_8$, $Y_9$, $Y_{10}$, $Y_{11}$, and $Y_{12}$ are hydrogens that are isotopically enriched with deuterium or tritium.

In embodiments, any two of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with deuterium. In embodiments, any three of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with deuterium. In embodiments, any four of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with deuterium. In embodiments, any five of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with deuterium. In embodiments, any six of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with deuterium. In embodiments, any seven of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with deuterium. In embodiments, any eight of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with deuterium. In embodiments, any nine of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with deuterium. In embodiments, any ten of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with deuterium. In embodiments, any eleven of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with deuterium. In embodiments, all of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with deuterium.

In embodiments, any two of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with tritium. In embodiments, any three of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with tritium. In embodiments, any four of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with tritium. In embodiments, any five of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with tritium. In embodiments, any six of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with tritium. In embodiments, any seven of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with tritium. In embodiments, any eight of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with tritium. In embodiments, any nine of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with tritium. In embodiments, any ten of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with tritium. In embodiments, any eleven of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with tritium. In embodiments, all of $Y_1$, $Y_2$, $Y_3$, $Y_4$, $Y_5$, $Y_6$, $Y_7$, $Y_8$, $Y_9$, $Y_{10}$, $Y_{11}$, or $Y_{12}$ are hydrogens that are isotopically enriched with tritium.

In an aspect, provided herein is a compound of formula VII:

Formula VII or a salt thereof. In Formula VII, 1, 2, 3, 4, 5, 6, 7, 8, 9, and 10 are carbon atoms, wherein at least one of 1, 2, 3, 4, 5, 6, 7, 8, 9, or 10 carbon atoms is isotopically enriched with carbon-13 or carbon-14. In embodiments, at least one of 1, 2, 3, 4, 5, 6, 7, 8, 9, or 10 carbon atoms is isotopically enriched with carbon-13. In embodiments, at least one of 1, 2, 3, 4, 5, 6, 7, 8, 9, or 10 carbon atoms is isotopically enriched with carbon-14.

In embodiments, any two of 1, 2, 3, 4, 5, 6, 7, 8, 9, or 10 carbon atoms are isotopically enriched with carbon-13 or carbon-14. In embodiments, any three of 1, 2, 3, 4, 5, 6, 7, 8, 9, or 10 carbon atoms are isotopically enriched with carbon-13 or carbon-14. In embodiments, any four of 1, 2, 3, 4, 5, 6, 7, 8, 9, or 10 carbon atoms are isotopically enriched with carbon-13 or carbon-14. In embodiments, any five of 1, 2, 3, 4, 5, 6, 7, 8, 9, or 10 carbon atoms are isotopically enriched with carbon-13 or carbon-14. In embodiments, any six of 1, 2, 3, 4, 5, 6, 7, 8, 9, or 10 carbon atoms are isotopically enriched with carbon-13 or carbon-14. In embodiments, any seven of 1, 2, 3, 4, 5, 6, 7, 8, 9, or 10 carbon atoms are isotopically enriched with carbon-13 or carbon-14. In embodiments, any eight of 1, 2, 3, 4, 5, 6, 7, 8, 9, or 10 carbon atoms are isotopically enriched with carbon-13 or carbon-14. In embodiments, any nine of 1, 2, 3, 4, 5, 6, 7, 8, 9, or 10 carbon atoms are isotopically enriched with carbon-13 or carbon-14. In embodiments, all carbon atoms are isotopically enriched with carbon-13 or carbon-14.

In embodiments, any two of 1, 2, 3, 4, 5, 6, 7, 8, 9, or 10 carbon atoms are isotopically enriched with carbon-13. In embodiments, any three of 1, 2, 3, 4, 5, 6, 7, 8, 9, or 10 carbon atoms are isotopically enriched with carbon-13. In embodiments, any four of 1, 2, 3, 4, 5, 6, 7, 8, 9, or 10 carbon atoms are isotopically enriched with carbon-13. In embodiments, any five of 1, 2, 3, 4, 5, 6, 7, 8, 9, or 10 carbon atoms are isotopically enriched with carbon-13. In embodiments, any six of 1, 2, 3, 4, 5, 6, 7, 8, 9, or 10 carbon atoms are isotopically enriched with carbon-13. In embodiments, any seven of 1, 2, 3, 4, 5, 6, 7, 8, 9, or 10 carbon atoms are isotopically enriched with carbon-13. In embodiments, any eight of 1, 2, 3, 4, 5, 6, 7, 8, 9, or 10 carbon atoms are isotopically enriched with carbon-13. In embodiments, any nine of 1, 2, 3, 4, 5, 6, 7, 8, 9, or 10 carbon atoms are isotopically enriched with carbon-13. In embodiments, all carbon atoms are isotopically enriched with carbon-13.

In embodiments, any two of 1, 2, 3, 4, 5, 6, 7, 8, 9, or 10 carbon atoms are isotopically enriched with carbon-14. In embodiments, any three of 1, 2, 3, 4, 5, 6, 7, 8, 9, or 10 carbon atoms are isotopically enriched with carbon-14. In embodiments, any four of 1, 2, 3, 4, 5, 6, 7, 8, 9, or 10 carbon atoms are isotopically enriched with carbon-14. In embodiments, any five of 1, 2, 3, 4, 5, 6, 7, 8, 9, or 10 carbon atoms are isotopically enriched with carbon-14. In embodiments, any six of 1, 2, 3, 4, 5, 6, 7, 8, 9, or 10 carbon atoms are isotopically enriched with carbon-14. In embodiments, any seven of 1, 2, 3, 4, 5, 6, 7, 8, 9, or 10 carbon atoms are isotopically enriched with carbon-14. In embodiments, any eight of 1, 2, 3, 4, 5, 6, 7, 8, 9, or 10 carbon atoms are isotopically enriched with carbon-14. In embodiments, any nine of 1, 2, 3, 4, 5, 6, 7, 8, 9, or 10 carbon atoms are isotopically enriched with carbon-14. In embodiments, all carbon atoms are isotopically enriched with carbon-14.

In an aspect, provided herein is a compound of formula VIII:

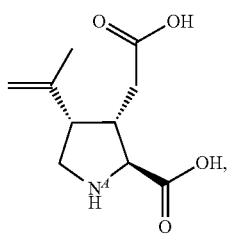

Formula VIII or a salt thereof. In Formula VIII, $N^4$ is a nitrogen atom which is isotopically enriched with nitrogen-15.

In some embodiments, a process of preparing a kainic acid (e.g., a compound of Formula Ia or Ib) comprises contacting one or more compounds disclosed herein with a KabC and/or a KabA polypeptide, or a composition comprising a KabC polypeptide and/or a KabA polypeptide, optionally in the presence of one or more substrates, additives or salts.

In some embodiments, a process of preparing a kainic acid (e.g., a compound of Formula Ia or Ib) comprises contacting one or more compounds disclosed herein with a KabC polypeptide or a composition comprising a KabC polypeptide, and optionally one or more substrates (e.g., α-keto-glutarate (aKG)). In some embodiments, a process comprises cyclizing a compound disclosed herein, wherein the process comprises contacting a compound disclosed herein with a KabC polypeptide or a composition comprising a KabC polypeptide. In some embodiments, a compound of Formula II, or a salt thereof, is contacted with a KabC polypeptide, or a composition comprising a KabC polypeptide. In some embodiments, a compound of Formula III, or a salt thereof, is contacted with a KabC polypeptide, or a composition comprising a KabC polypeptide. In some embodiments, a compound of Formula V, or a salt thereof, is contacted with a KabC polypeptide, or a composition comprising a KabC polypeptide. In some embodiments, a compound of Formula III, or a salt thereof, and a compound of Formula V, or a salt thereof, is contacted with a KabC polypeptide, or a composition comprising a KabC polypeptide. In certain embodiments, a compound disclosed herein is contacted with a KabC polypeptide, or a composition comprising a KabC polypeptide, thereby forming a compound of Formula Ia or Ib, or a salt thereof.

In some embodiments, a process of preparing a kainic acid (e.g., a compound of Formula Ia or Ib) comprises contacting a compound disclosed herein with a KabA polypeptide or a composition comprising a KabA polypeptide, and optionally one or more substrates (e.g., α-keto-glutarate (aKG)). In some embodiments, a process comprises cyclizing a compound disclosed herein, wherein the process comprises contacting a compound disclosed herein with a KabA polypeptide or a composition comprising a KabA polypeptide. In certain embodiments, a compound disclosed herein is contacted with a KabA polypeptide, or a composition comprising a KabA polypeptide, thereby forming a compound of Formula Ia or Ib, or a salt thereof. In some embodiments, a compound of Formula II, or a salt thereof, is contacted with a KabA polypeptide, or a composition comprising a KabA polypeptide. In some embodiments, a compound of Formula III, or a salt thereof, is contacted with a KabA polypeptide, or a composition comprising a KabA polypeptide. In some embodiments, a compound of Formula V, or a salt thereof, is contacted with a KabA polypeptide, or a composition comprising a KabA polypeptide. In some embodiments, a compound of Formula III, or a salt thereof, and a compound of Formula V, or a salt thereof, is contacted with a KabA polypeptide, or a composition comprising a KabA polypeptide.

In some embodiments, a process of preparing a kainic acid (e.g., a compound of Formula Ia or Ib) comprises contacting a compound disclosed herein with a KabC polypeptide and/or a KabA polypeptide. In some embodiments, one or more compounds disclosed herein are contacted with a KabC polypeptide and/or a KabA polypeptide and a substrate, non-limiting examples of which include one or more of α-keto-glutarate (αKG), L-glutamate, glucose, dimethylallyl pyrophosphate (DMAPP), dimethylallyl diphosphate (DMADP), L-ascorbate, magnesium and iron, the like, a salt thereof or a combination thereof. In some embodiments, one or more compounds disclosed herein are contacted with a KabC polypeptide and/or a KabA polypeptide, L-glutamate and DMAPP. In some embodiments, one or more compounds disclosed herein are contacted with a KabC polypeptide and/or a KabA polypeptide and α-keto-glutarate. For example, in certain embodiments, a compound of Formula II, or a salt thereof, is contacted with a KabC polypeptide or a composition comprising a KabC polypeptide and α-keto-glutarate. In certain embodiments, a process comprises contacting a compound of Formula III, or a salt thereof, and a compound of Formula V, or a salt thereof, with a KabC polypeptide, a KabA polypeptide and α-keto-glutarate.

In some embodiments, a KabC polypeptide and/or a KabA polypeptide, or a composition comprising a KabC polypeptide and/or a KabA polypeptide, is contacted with DMAPP and L-glutamate. In some embodiments, a KabC polypeptide and/or a KabA polypeptide, or a composition comprising a KabC polypeptide and/or a KabA polypeptide, is contacted with DMAPP, L-glutamate and αKG, optionally in the presence of one or more of iron, magnesium and/or oxygen.

In some embodiments a composition comprising a KabC polypeptide and/or a KabA polypeptide comprises a crude, partially purified or purified KabC or KabA polypeptide. In some embodiments a composition comprising KabC polypeptide and/or a KabA polypeptide comprises a crude extract (e.g., a cell lysate) or conditioned media comprising a KabC polypeptide and/or a KabA polypeptide. In some embodiments, a composition comprising a KabC polypeptide and/or a KabA polypeptide comprises one or more recombinant organisms, for example a genetically modified microorganism engineered to express a recombinant KabC and/or KabA polypeptide. Accordingly, in certain embodiments, a process comprises contacting one or more compounds and/or substrates disclosed herein with one or more microorganisms (e.g., bacteria or yeast) that express a KabC and/or KabA polypeptide. In some embodiments, a process comprises contacting one or more compounds and/or substrates disclosed herein with a recombinant E. coli that expresses a recombinant KabC and/or a KabA polypeptide.

In some embodiments, a process of making a compound disclosed herein comprises culturing, propagating or growing a recombinant cell described herein in a suitable culture medium. In some embodiments, a process of making a compound disclosed herein (e.g., a compound of Formula Ia or Ib) comprises culturing, growing or expanding one or more recombinant cells configured to express a KabC and/or a KabA polypeptide, and contacting the cultured recombinant cells with a compound of Formula II, III, IV, V, a salt thereof, or a combination thereof. In some embodiments, a process of making a compound disclosed herein comprises culturing one or more recombinant cells configured to express a KabC and/or a KabA polypeptide, and contacting the cultured recombinant cells with a compound of Formula II, III, IV, V, a salt thereof, or a combination thereof, and one or more substrates (e.g., selected from α-keto-glutarate (αKG), L-glutamate, glucose, dimethylallyl pyrophosphate (DMAPP), dimethylallyl diphosphate (DMADP), L-ascorbate, magnesium, iron, the like, and salts thereof). In certain embodiments, a process further comprises isolating or purifying a compound of Formula Ia or Ib, or a salt thereof, from a culture medium (i.e., conditioned media) or from a recombinant cell described herein using a suitable method.

In some embodiments, a partially purified KabC and/or KabA polypeptide is in a range of 10%-90% pure, 10%-80% pure, 10%-60% pure or 30% to 60% pure. In certain embodiments, a purified KabC and/or KabA polypeptide is at least 75% pure, at least 80% pure, at least 90% pure, at least 95% pure or at least 98% pure. In some embodiments, a purified KabC and/or a purified KabA polypeptide is 90-100%, 95-100% pure or 98-100% pure.

In some embodiments, a KabC and/or KabA polypeptide is a recombinant polypeptide. A recombinant KabC and/or KabA polypeptide can be expressed by a suitable recombinant organism, non-limiting examples of which include a genetically modified plant, algae, mammalian cell, bacteria or yeast. In some embodiments, a recombinant KabC and/or KabA polypeptide can be expressed by a suitable recombinant microorganism, non-limiting examples of which include a genetically modified bacteria or yeast. An organism can be genetically modified using any suitable method, system or vector. For example, a microorganism can be genetically modified by stable or transient integration of a recombinant polynucleotide (e.g., a recombinant expression vector) using a suitable vector or delivery system, non-limiting examples of which include a virus, phage, plasmid, cosmid, BAC, CRISPR element, the like or combinations thereof.

In some embodiments, a recombinant KabC and/or KabA polypeptide is expressed by a suitable expression system non-limiting examples of which include an insect expression system (e.g., baculovirus mediated expression), a plant expression system, an algae expression system, a mammalian expression system, a yeast expression system and a prokaryotic (e.g., bacterial) expression system. In some embodiments, a recombinant KabC and/or KabA polypeptide is generated, expressed and/or produced by a suitable bacteria. In certain embodiments, a recombinant KabC and/or KabA polypeptide is generated, expressed and/or produced by a recombinant bacteria of the genus *Escherichia*. In certain embodiments, a recombinant KabC and/or KabA polypeptide is generated, expressed and/or produced by a recombinant *Escherichia coli* (*E. coli*), or a suitable strain thereof.

In some embodiments, presented herein is recombinant polynucleotide comprising a polynucleotide encoding a KabA polypeptide and/or a KabC polypeptide. In some embodiments, presented herein is an expression vector comprising a recombinant polynucleotide encoding a KabA polypeptide and/or a KabC polypeptide. In some embodiments, an expression vector comprises a polynucleotide encoding a KabA polypeptide and a KabC polypeptide. In some embodiments, an expression vector comprises one or more polynucleotides selected from SEQ ID NOs:6-10 and 33-34. In certain embodiments, an expression vector disclosed herein is configured to express a KabA polypeptide and/or a KabC polypeptide in a suitable organism, microorganism or expression system. Accordingly, an expression vector often comprises one or more suitable promoters that are operably linked to a polynucleotide encoding a KabA polypeptide and/or KabC polypeptide.

In some embodiments, presented herein is a suitable recombinant cell comprising a polynucleotide encoding a KabA polypeptide and/or a KabC polypeptide. In some embodiments, a recombinant cell is configured to express a KabA polypeptide and/or a KabC polypeptide. In some embodiments, a recombinant cell comprises an expression vector described herein. In certain embodiments, a recombinant cell is a genetically modified mammalian, insect, plant, yeast or prokaryotic cell that is configured to express a KabA polypeptide and/or a KabC polypeptide. In certain embodiments, a recombinant cell is a bacterial cell. In some embodiments a recombinant cell is a recombinant or genetically modified *E. coli*.

In some embodiments, a KabC polypeptide comprises an amino acid sequence that is 70%-100%, 80%-100%, 90%-100%, 95%-100% or 98%-100% identical to the amino acid sequence of any one of SEQ ID NOs:1-5, a conservatively modified variant thereof, or an enzymatically active portion thereof. A KabC polypeptide that is 70%-100%, 80%-100%, 90%-100%, 95%-100% or 98%-100% identical to the amino acid sequence of any one of SEQ ID NOs:1-5, or a portion thereof, may comprise non-identical amino acids that are conservative substitutions. Accordingly, a KabC polypeptide described herein is sometimes a conservatively modified variant of KabC polypeptide of any one of SEQ ID NOs:1-5. In certain embodiments, a KabC polypeptide comprises an amino acid sequence that is at least 70%, at least 75%, at least 80%, at least 85%, at least 90%, at least 90% or at least 95% identical to the amino acid sequence of any one of SEQ ID NOs:1-5. In embodiments, the KabC polypeptide comprises an amino acid sequence that is at least 80% identical to the amino acid sequence of any one of SEQ ID NOs: 1-5. In embodiments, the KabC polypeptide comprises an amino acid sequence that is at least 90% identical to the amino acid sequence of any one of SEQ ID NOs: 1-5. In embodiments, the KabC polypeptide comprises an amino acid sequence that is at least 95% identical to the amino acid sequence of any one of SEQ ID NOs: 1-5. In certain embodiments, a KabC polypeptide comprises an amino acid sequence of any one of SEQ ID NOs: 1-5. In embodiments, the KabC polypeptide comprises an amino acid sequence of SEQ ID NO: 1, or a conservatively modified variant thereof. In embodiments, the KabC polypeptide comprises an amino acid sequence of SEQ ID NO: 2, or a conservatively modified variant thereof. In embodiments, the KabC polypeptide comprises an amino acid sequence of SEQ ID NO: 3, or a conservatively modified variant thereof. In embodiments, the KabC polypeptide comprises an amino acid sequence of SEQ ID NO: 4, or a conservatively modified variant thereof. In embodiments, the KabC polypeptide comprises an amino acid sequence of SEQ ID NO: 5, or a conservatively modified variant thereof.

In some embodiments, a KabC polypeptide comprises an amino acid sequence encoded by a polynucleotide comprising a sequence that is 70%-100%, 80%-100%, 90%-100%, 95%-100% or 98%-100% identical to the polynucleotide sequence of any one of SEQ ID NOs:6-10 and 33-34, or a portion thereof. In certain embodiments, a KabC polypeptide comprises an amino acid sequence encoded by a polynucleotide that is at least 70%, at least 75%, at least 80%, at least 85%, at least 90%, at least 90% or at least 95% identical to the polynucleotide sequence of any one of SEQ ID NOs:6-10 and 33-34. In embodiments, the polynucleotide comprises a sequence that is at least about 80% identical to any one of SEQ ID NOs: 6-10 and 33-34. In embodiments, the polynucleotide comprises a sequence that is at least about 90% identical to any one of SEQ ID NOs: 6-10 and 33-34. In embodiments, the polynucleotide comprises a sequence that is at least about 95% identical to any one of SEQ ID NOs: 6-10 and 33-34. In certain embodiments, a KabC polypeptide is encoded by a polynucleotide sequence of any one of SEQ ID NOs:6-10 and 33-34.

In some embodiments, a KabA polypeptide comprises an amino acid sequence that is 70%-100%, 80%-100%, 90%-100%, 95%-100% or 98%-100% identical to the amino acid sequence of any one of SEQ ID NOs:11-15, a conservatively modified variant thereof, or an enzymatically active portion thereof. A KabA polypeptide that is 70%-100%, 80%-100%, 90%-100%, 95%-100% or 98%-100% identical to the amino acid sequence of any one of SEQ ID NOs: 11-15, or a portion thereof, may comprise non-identical amino acids that are conservative substitutions. Accordingly, a KabA polypeptide described herein is sometimes a conservatively modified variant of KabA polypeptide of any one of SEQ ID NOs:11-15. In certain embodiments, a KabA polypeptide comprises an amino acid sequence that is at least 70%, at least 75%, at least 80%, at least 85%, at least 90%, at least 90% or at least 95% identical to the amino acid sequence of any one of SEQ ID NOs: 11-15. In embodiments, the KabA polypeptide comprises an amino acid sequence that is at least 80% identical to the amino acid sequence of any one of SEQ ID NOs: 11-15. In embodiments, the KabA polypeptide comprises an amino acid sequence that is at least 90% identical to the amino acid sequence of any one of SEQ ID NOs: 11-15. In embodiments, the KabA polypeptide comprises an amino acid sequence that is at least 95% identical to the amino acid sequence of any one of SEQ ID NOs: 11-15. In certain embodiments, a KabA polypeptide comprises an amino acid sequence of any one of SEQ ID NOs:11-20. In embodiments, the KabA polypeptide comprises an amino acid sequence of SEQ ID NO: 11, or a conservatively modified variant thereof. In embodiments, the KabA polypeptide comprises an amino acid sequence of SEQ ID NO: 12, or a conservatively modified variant thereof. In embodiments, the KabA polypeptide comprises an amino acid sequence of SEQ ID NO: 13, or a conservatively modified variant thereof. In embodiments, the KabA polypeptide comprises an amino acid sequence of SEQ ID NO: 14, or a conservatively modified variant thereof. In embodiments, the KabA polypeptide comprises an amino acid sequence of SEQ ID NO: 15, or a conservatively modified variant thereof.

In some embodiments, a KabA polypeptide comprises an amino acid sequence encoded by a polynucleotide comprising a sequence that is 70%-100%, 80%-100%, 90%-100%, 95%-100% or 98%-100% identical to the polynucleotide sequence of any one of SEQ ID NOs:16-20, or a portion thereof. In certain embodiments, a KabA polypeptide comprises an amino acid sequence encoded by a polynucleotide that is at least 70%, at least 75%, at least 80%, at least 85%, at least 90%, at least 90% or at least 95% identical to the polynucleotide sequence of any one of SEQ ID NOs:16-20. In embodiments, the polynucleotide comprises a sequence that is at least about 80% identical to any one of SEQ ID NOs:16-20. In embodiments, the polynucleotide comprises a sequence that is at least about 90% identical to any one of SEQ ID NOs:16-20. In embodiments, the polynucleotide comprises a sequence that is at least about 95% identical to any one of SEQ ID NOs:16-20. In certain embodiments, a KabA polypeptide is encoded by a polynucleotide sequence of any one of SEQ ID NOs:16-20.

In certain embodiments, a KabC or KabA polypeptide (or polynucleotide encoding the same) is obtained or derived from algae (e.g., a red algae), comprising the sequence of the corresponding protein, or a conservatively modified variant thereof. In certain embodiments, a KabC or KabA polypeptide (or a polynucleotide encoding the same) is obtained or derived from an organism of the class Florideophyceae. In certain embodiments, a KabC or KabA polypeptide (or polynucleotide encoding the same) is obtained or derived from an organism of the genus *Digenea, Palmaria, Rhodophysema*, or *Grateloupia*. In some embodiments, a KabC or KabA polypeptide (or polynucleotide encoding the same) is a *Digenea* spp. polypeptide, a *Rhodophysema* spp. polypeptide, a *Palmaria* spp. polypeptide or a *Grateloupia* spp. polypeptide. In certain embodiments, a KabC or KabA polypeptide (or polynucleotide encoding the same) is obtained or derived from *Digenea simplex, Rhodophysema elegans, Palmaria palmata, Palmaria hecatensis* or *Grateloupia filicina*. Additional algal sources of KabA and/or KabC are disclosed herein, including within the figures. In embodiments, the KabA and KabC are obtained or derived from the same genus or species. In embodiments, the KabA and KabC are obtained or derived from different genera or species.

EXAMPLES

The following illustrative examples are representative of embodiments of compositions and methods described herein and are not meant to be limiting in any way.

Example 1

Genomic Sequencing and Gene Cluster Identification

Whole genome sequencing was performed of the well-studied kainic acid producer *D. simplex* to identify the kainic acid biosynthetic genes and determine their genetic context. Red macroalgae genomes have proven challenging due to their close association with a diverse array of marine microbes and crustaceans, which means sequencing efforts result in highly complex metagenomes. Illumina short read sequencing results in assemblies of millions of small contigs making it difficult to impossible to resolve large genic blocks in red macroalgae genomes. Therefore, we sequenced *D. simplex* with the Oxford Nanopore Technology (ONT), which produces long, single molecule sequences that greatly facilitate assembly of large genomes [23]. While the *D. simplex* genome was predicted to be ~200 Mb, the high microbial level in the isolated DNA was sequenced on the high throughput PromtheION ONT platform, producing 47 Gb of sequence. The resulting genome assembly was 299 Mb in length, with 8,246 contigs and the longest contig 3.9 Mb, with a contig N50 of 57 kb (FIG. 2). Based on GC % analysis, we predicted that 205 Mb of the assembly were found to be associated with *D. simplex*, while 88 Mb were associated with high QC % bacterial contigs.

Figure 5:
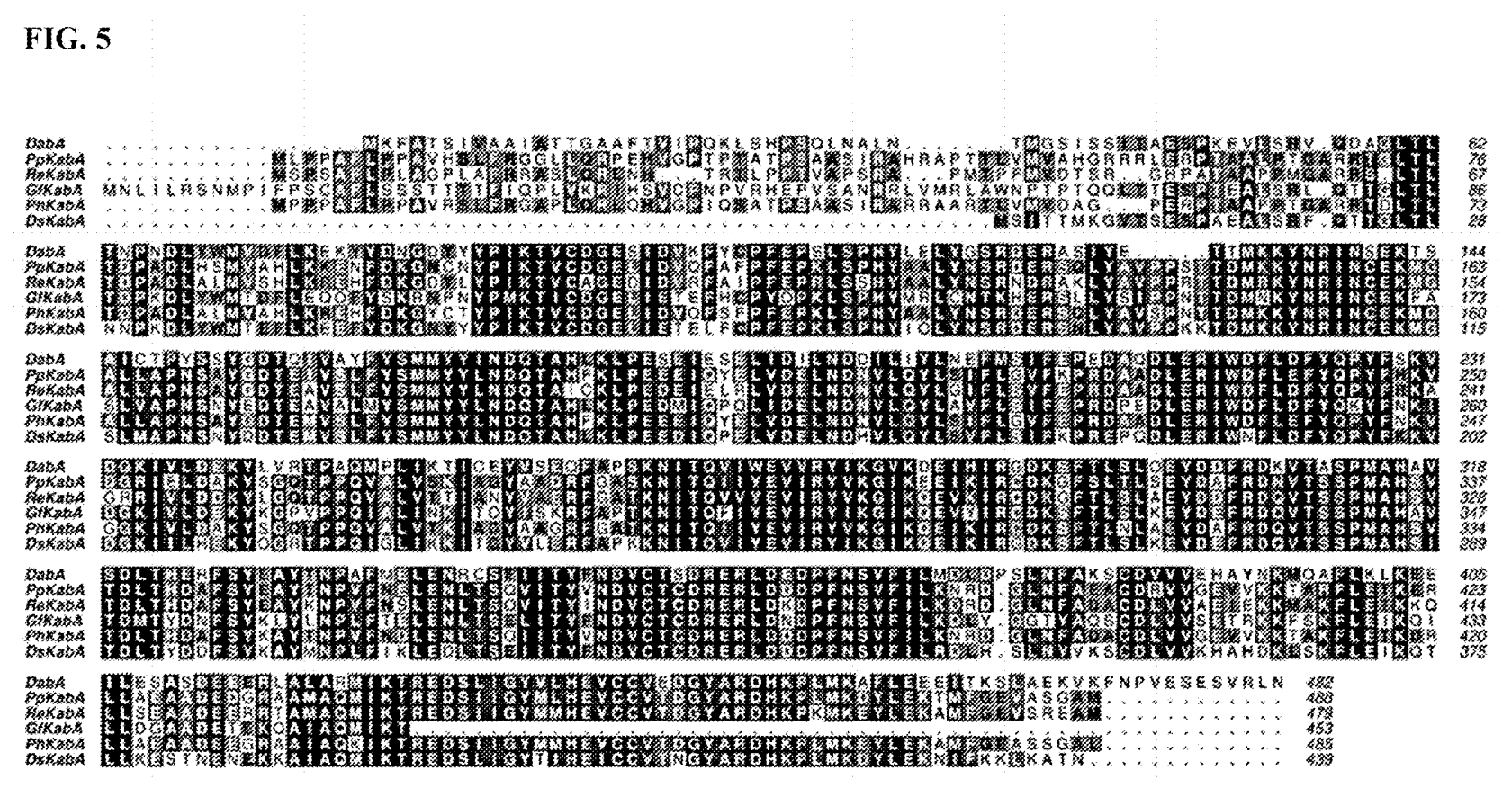
Figure 6:
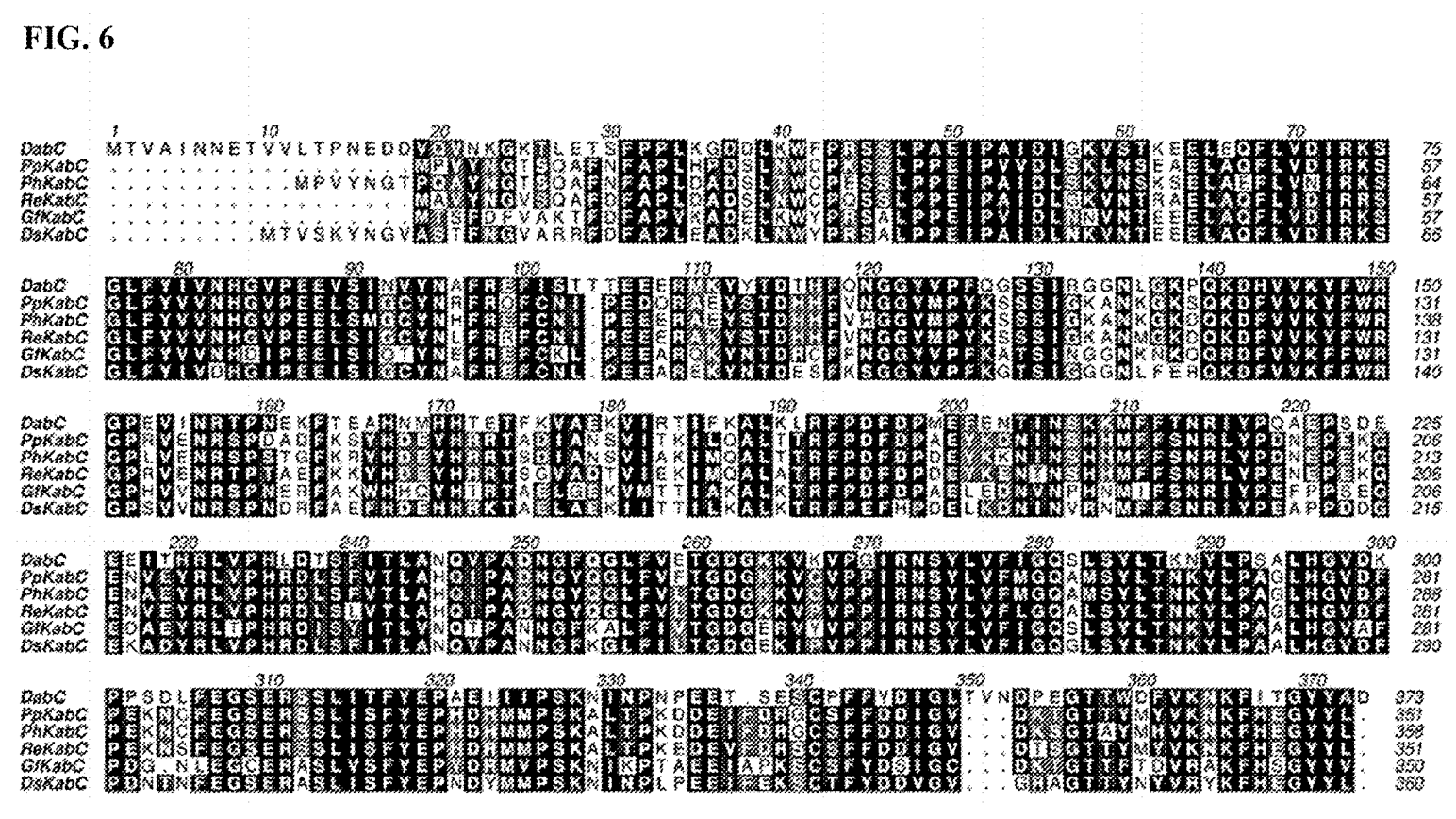

Upon analyzing the *D. simplex* genome for the presence of homologs to the domoic acid biosynthetic (dab) genes, we uncovered a 12 kb three-gene kainic acid biosynthesis (kab) cluster containing an annotated N-prenyltransferase, α-ketoglutarate (αKG) dependent dioxygenase, and several retrotransposable elements (integrase, reverse transcriptase, and RNase H domains) (FIG. 1, view (C)). Many organisms, including bacteria, fungi, and even plants, are known to cluster genes within the same biosynthetic pathway [24,25]. The kab gene clustering is consistent with early examples of red algae clustering genes [26] and suggested that it could also be a feature in red algal specialized metabolism. Analysis of the NCBI transcriptome database identified similar kab transcripts from four different red algae, namely Palmaria palmata, Grateloupia filicina, Palmaria hecatensis, and Rhodophysema elegans [27,28]. Notably, kainic acid has been previously isolated from P. palmata [29], while the other three red algae are not known producers. Sequence alignment of the KabA N-prenyltransferase and KabC αKG-dependent dioxygenase proteins revealed high levels of conservation (FIG. 5 and FIG. 6). Both the domoic acid N-prenyltransferase dabA [22] and most of the KabA proteins contain a non-conserved N-terminal region that may function as a signal peptide to localize the protein to a cellular compartment (FIG. 5). However, the D. simplex KabA (DskabA) lacks this sequence and is thus expected to remain within the cytosol.

Bundled between the D. simplex kabAC genes is a viral reverse transcriptase domain-containing gene, kabB. This association suggests that both kabA and kabC could be part of a mobile genetic element that could facilitate horizontal transfer between different algae and could potentially explain the mixed phylogenetic distribution of kainic acid biosynthetic gene containing red algae. Mobile genetic elements are common across plants, bacteria, and fungi and have been shown to be integral in meditating horizontal gene transfer of entire pathways [30]. To evaluate whether this feature is conserved within the kab clusters, we performed genome sequencing of a second known kainic acid producer, P. palmata, to determine the genetic context of its kab genes. As with D. simplex, the kainic acid genes were found to be tightly clustered. However, the gene synteny was not found to be conserved with only a short 1.2 kb intergenic region between ppkabA and ppkabC and with different gene orientation. Immediately outside the P. palmata cluster is a transposable element, which is distinct from the type observed in D. simplex. While this difference suggested that the retrotransposon was either not the mode of gene transport or that it had since been subsequently lost, more clusters could be studied to validate this trend.

TABLE S3

NCBI accession codes for deposited sequencing data and previously published RNASeq data.

|  | Organism | NCBI Accession Number |
|---|---|---|
| Digenea simplex bioproject | | PRJNA509898 |
| Digenea simplex hologenome | | RXNZ00000000 |
| Digenea simplex SRA | | SRR8325638, SRR8325637, SRR8325636 |
| Digenea simplex kainic acid cluster | | MK312630 |
| Palmaria palmata bioproject | | PRJNA509900 |
| Palmaria palmata SRA | | SRR8325558, SRR8325559 |
| Palmaria palmata kainic acid cluster | | MK312631 |
| PpKabA from published transcriptomics [28] | Palmaria palmata | QCC62375 |
| PpKabC from published transcriptomics [28] | Palmaria palmata | QCC62376 |
| DsKabA | Digenea simplex | QCC62379 |
| DsKabC | Digenea simplex | QCC62383 |
| PpKabA | Palmaria palmata | QCC62384 |
| PpKabC | Palmaria palmata | QCC62385 |
| ReKabA | Rhodophysema elegans | QCC62371 |
| ReKabC | Rhodophysema elegans | QCC62372 |
| PhKabA | Palmaria hecatensis | QCC62373 |
| PhKabC | Palmaria hecatensis | QCC62374 |
| GfKabA (partial sequence) [27] | Grateloupia filicina | QCC62377 |
| GfKabC [27] | Grateloupia filicina | QCC62378 |

Validation of the Kainic Acid Biosynthesis Enzymes KabA and KabC

Figure 7:
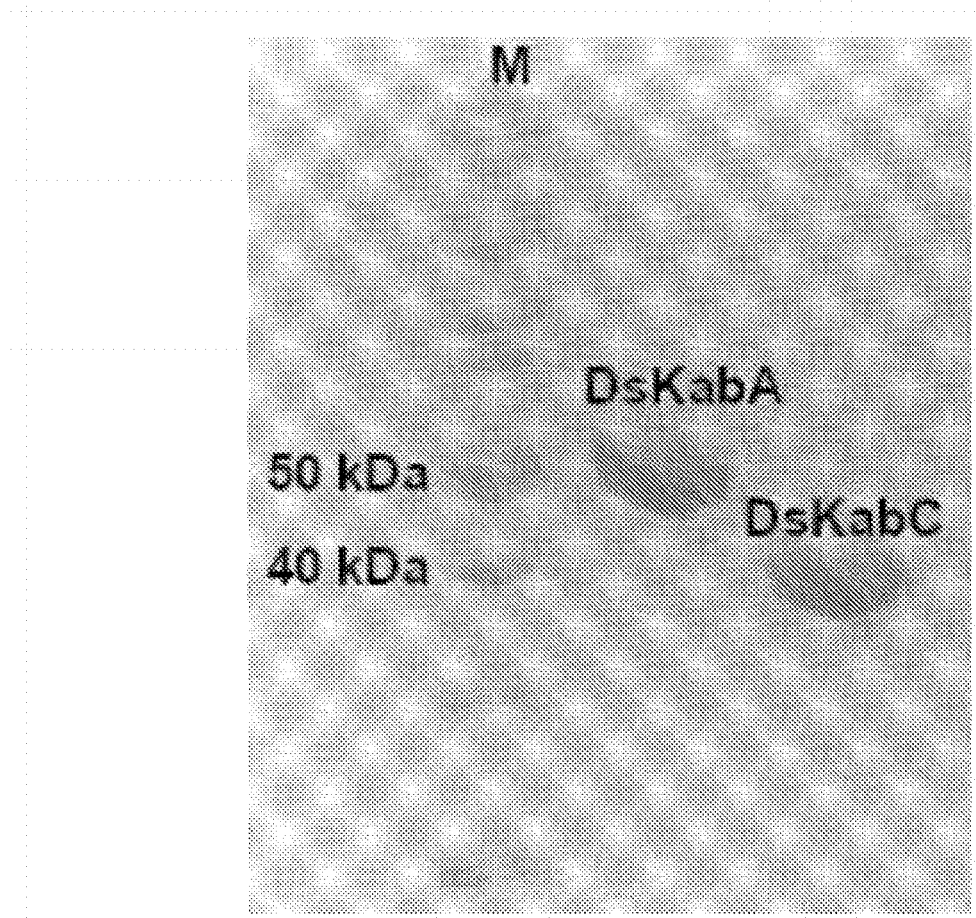
FIG. 7 shows 12% SDS-PAGE loaded with EZ-Run Rec Protein Ladder (Fisher Bioreagents), DsKabA, and DsKabC.
Figure 8:
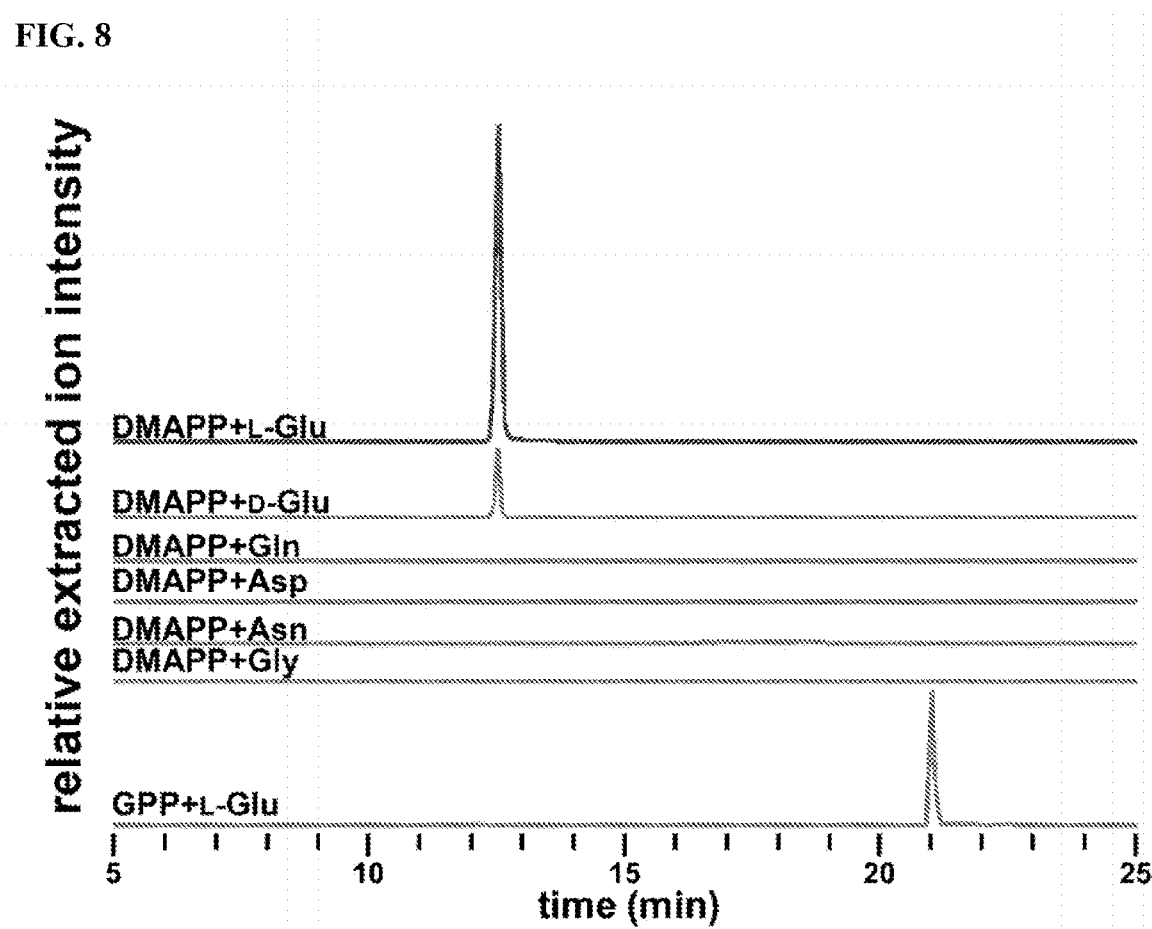
FIG. 8 shows that DsKabA substrate specificity was analyzed by LCMS. Each trace represents the extracted ion chromatogram for the expected $(M-H)^-$ product mass±0.5 m/z. DMAPP+L-Glu: 214.1 m/z, DMAPP+D-Glu: 214.1 m/z, DMAPP+L-Gln: 213.1 m/z, DMAPP+L-Asp: 200.1 m/z, DMAPP+L-Asn: 199.1 m/z, DMAPP+Gly: 142.2 m/z, and GPP+L-Glu: 282.2 m/z.
Figure 9:
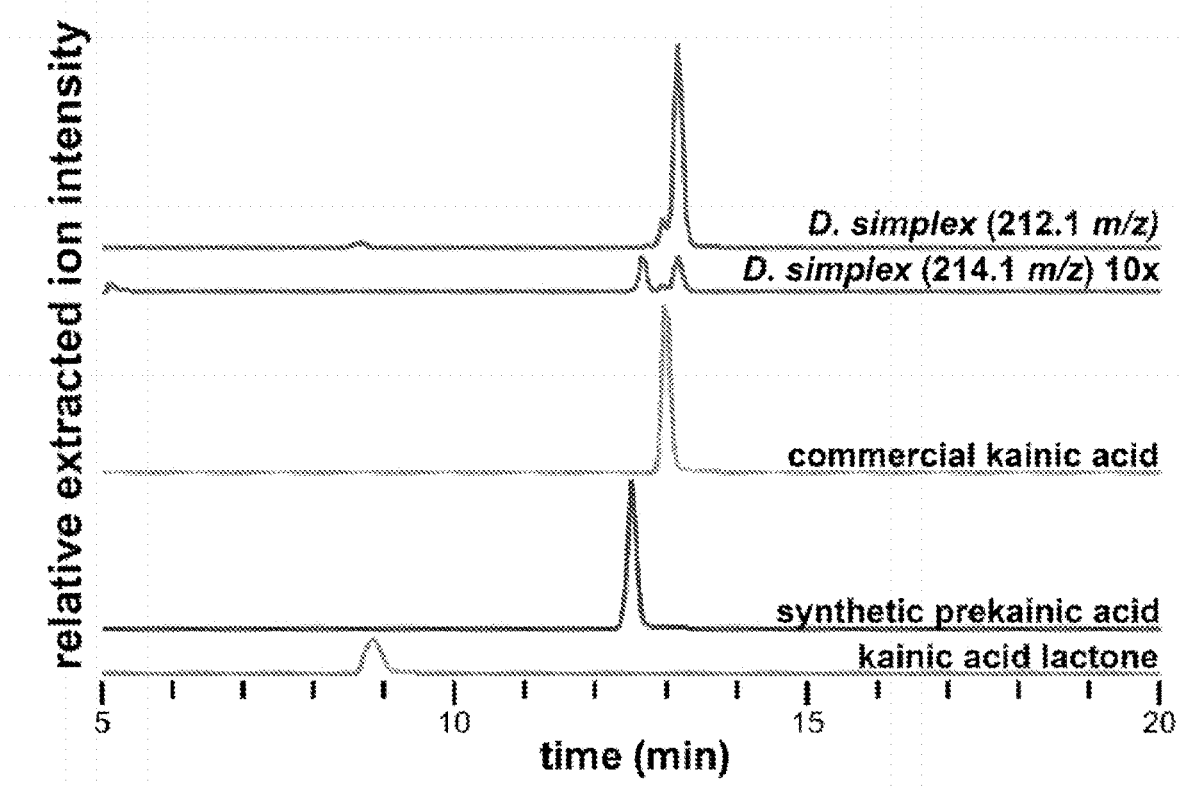
FIG. 9 shows that an aqueous *D. simplex* extract was analyzed by LCMS and compared to synthetic/enzymatic standards to verify the presence of kainic acid, kainic acid lactone, and prekainic acid. Each trace represents the $(M-H)^-$ extracted ion chromatogram for prekainic acid (214.1±0.1 m/z) and kainic acid/kainic acid lactone (212.1±0.1 m/z). The *D. simplex* trace extracted for the prekainic acid mass (214.1±0.1 m/z) was magnified tenfold.

To confirm the proposed kainic acid biosynthetic pathway, dsKabA and dsKabC were successfully expressed in Escherichia coli and purified to homogeneity (FIG. 7). Incubation of DsKabA with the anticipated substrates DMAPP and L-glutamate produced N-dimethylallyl-L-glutamic acid (prekainic acid) as confirmed by NMR structural elucidation and LCMS comparison with a synthetic standard (FIG. 3). Consistent with other members of the terpene cyclase family fold, $Mg^{2+}$ is a required cofactor in the reaction (FIG. 3). We next explored the substrate selectivity of DsKabA. Exchange of L-glutamate for D-glutamate showed diminished turnover while L-glutamine, L-aspartate, L-asparagine, and glycine did not produce appreciable amounts of N-prenylated product (FIG. 8). In contrast, when we replaced DMAPP with GPP in the reaction with L-glutamate, we observed the formation of N-geranyl-L-glutamic acid (L-NGG), the first biosynthetic precursor to domoic acid (FIG. 8). This high level of amino acid selectivity and modest prenyl donor promiscuity was also observed with DabA from domoic acid biosynthesis [22]. To give evidence to the physiological relevance of prekainic acid in the biosynthesis of kainic acid, we examined the aqueous extract of D. simplex. High resolution LCMS analysis revealed the presence of a compound with both the exact mass and retention time of prekainic acid (FIG. 9).

Figure 10:
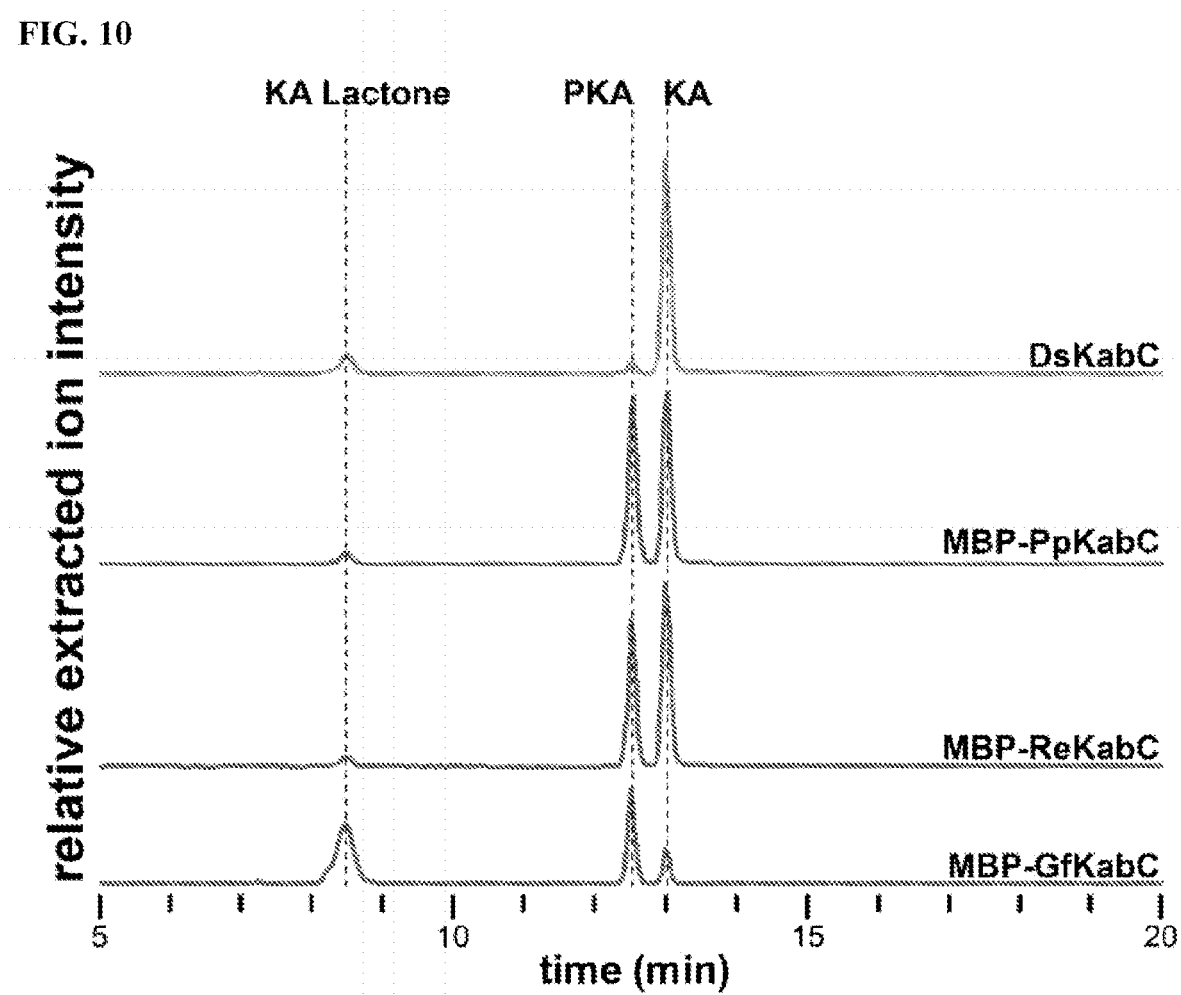
FIG. 10 shows the reaction products of KabC enzymes from *D. simplex*, *P. palmata*, *R. elegans*, and *G. filicinia* were analyzed by LCMS following a 5 h incubation. DsKabC was used in the His6 tag cleaved form while the other three homologs were tested as an MBP-fusion. Each trace represents the $(M-H)^-$ extracted ion chromatogram for both prekainic acid (214.1±0.5 m/z) and kainic acid/kainic acid lactone (212.1±0.5 m/z).

After reconstituting DsKabA activity, we next aimed to determine if DsKabC could directly convert prekainic acid to kainic acid. Incubation of DsKabC with prekainic acid, αKG, L-ascorbate, and Fe$^{2+}$ resulted in the conversion of prekainic acid to two products with the expected mass of kainic acid (FIG. 3). Addition of the iron chelator EDTA nearly abolished activity. The major product had the same HPLC retention time and MS of commercially available kainic acid, and was further confirmed by to be kainic acid following NMR structural elucidation. Examination of the in vitro products of other algal KabC enzymes revealed a similar trend, wherein prekainic acid was converted to kainic acid and another minor isomeric product (FIG. 10). Notably, the KabC ortholog from *G. filicinia*, GfKabC, produced primarily this other kainic acid isomer. By scaling up the GfKabC reaction, we isolated and characterized this product by NMR to reveal kainic acid lactone (FIG. 1, view (B)). Kainic acid lactone has been previously isolated from kainic acid producing red algae [31] and shown to be an iGluR antagonist [32], in contrast to the agonistic activity of kainic acid. While kainic acid lactone has been isolated in small quantities from several red algae, it can be produced from kainic acid under acidic conditions, which prompted the initial concern that it may simply be an isolation artifact. However, the combination of our in vitro experiments and *D. simplex* distilled water extractions suggest that this bicyclic kainoid is an authentic natural product (FIG. 9). The relative ratio of kainic acid to kainic acid lactone appeared to vary depending on the particular KabC ortholog (FIG. 10).

Scalable Bioproduction of Kainic Acid

Figure 11:
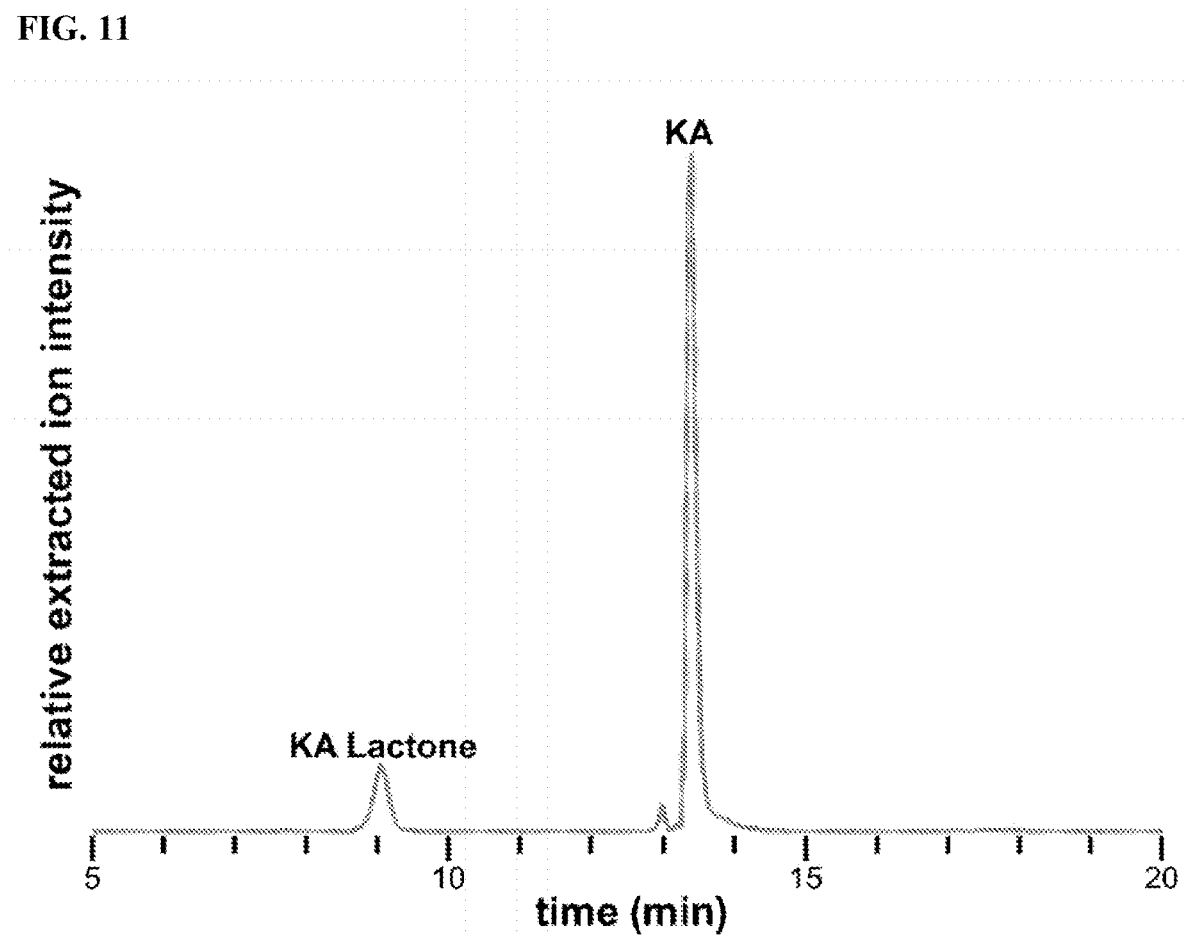
FIG. 11 shows kainic acid production by in vitro conversion of synthetic prekainic acid by DsKabC. The trace represents the $(M-H)^-$ extraction ion chromatogram for prekainic acid (PKA, 214.1±0.1 m/z) and kainic acid/kainic acid lactone (KA/KA Lactone, 212.1±0.1 m/z). The prekainic acid peak is <0.3% of the kainic acid intensity and is not visible.
Figure 29:
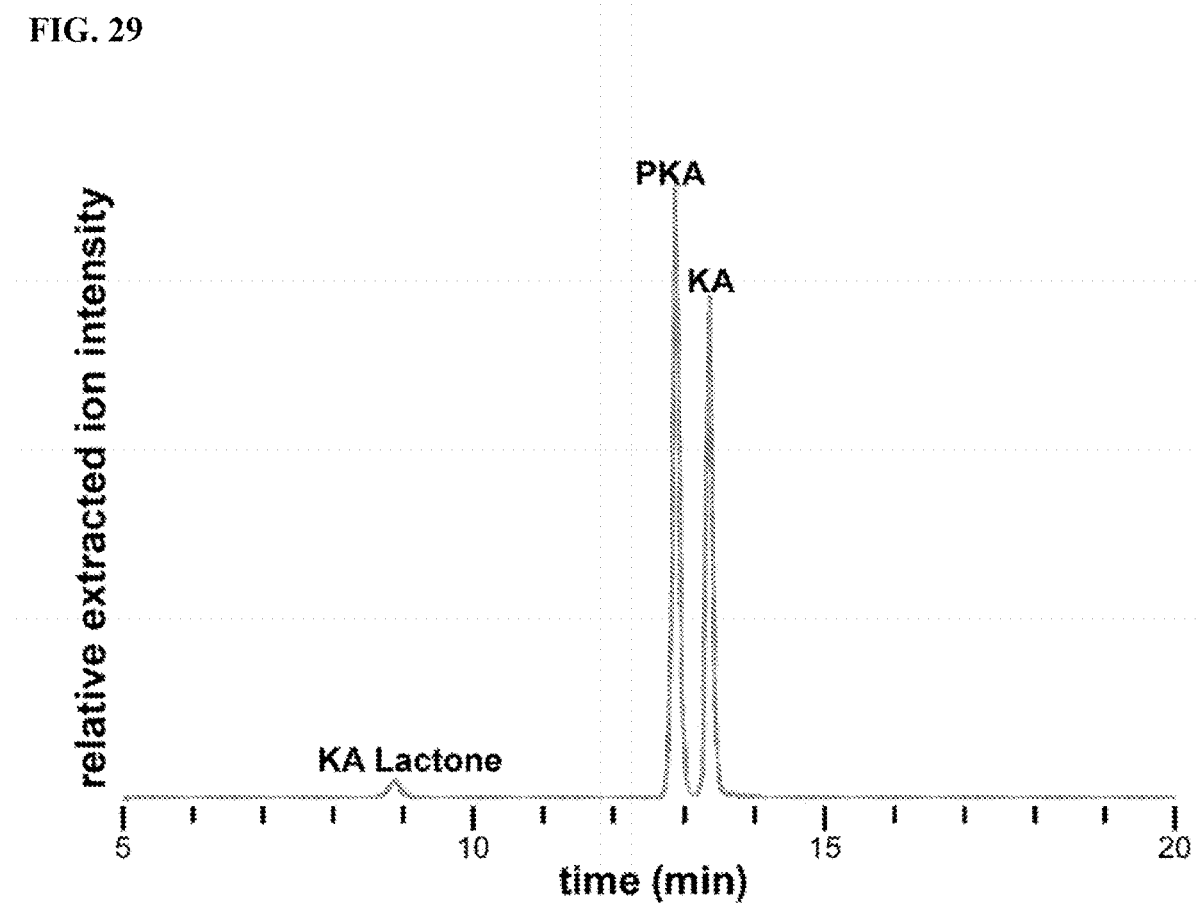
FIG. 29 shows analysis of kainic acid production by a coupled in vitro reaction of DsKabA and DsKabC as monitored by LCMS after an 18 h incubation. The trace represents the (M−H)⁻ extracted ion chromatogram for prekainic acid (PKA, 214.1±0.1 m/z) and kainic acid/kainic acid lactone (KA/KA Lactone, 212.1±0.1 m/z).

Once the Kab enzymatic functions were validated, we focused on the development of a practical kainic acid production system. As the biosynthesis requires only two enzymes, we initially envisioned two complementary in vitro production routes. First, we evaluated an enzymatic total biosynthesis wherein kainic acid is produced from the three substrates, DMAPP, L-Glu, and αKG (FIG. 4, view (a)). In a single pot reaction, we showed that recombinant DsKabA and DsKabC, each isolated from 1 L *E. coli* culture, could be coupled together to produce kainic acid. While kainic acid was successfully produced, the reaction did not go to completion and only afforded <1 mg of kainic acid with an approximate <10% yield (FIG. 29). As this procedure is also limited by the need to purify two enzymes, we developed a two-step chemoenzymatic method necessitating just one biocatalyst. We replaced KabA and its expensive DMAPP substrate with a simplified synthetic preparation of prekainic acid by reductive amination of L-glutamate with 3-methyl-2-butenal (FIG. 4, view (b)). Upon purification, synthetic prekainic acid was then completely enzymatically converted with DsKabC, producing 4.6 mg kainic acid with a 46% yield from 1 L of purified protein and a 26% overall yield starting from L-Glu (FIG. 11). Although the chemoenzymatic route was simpler, neither approach appeared to be readily applicable for large scale production of kainic acid.

Figure 4:
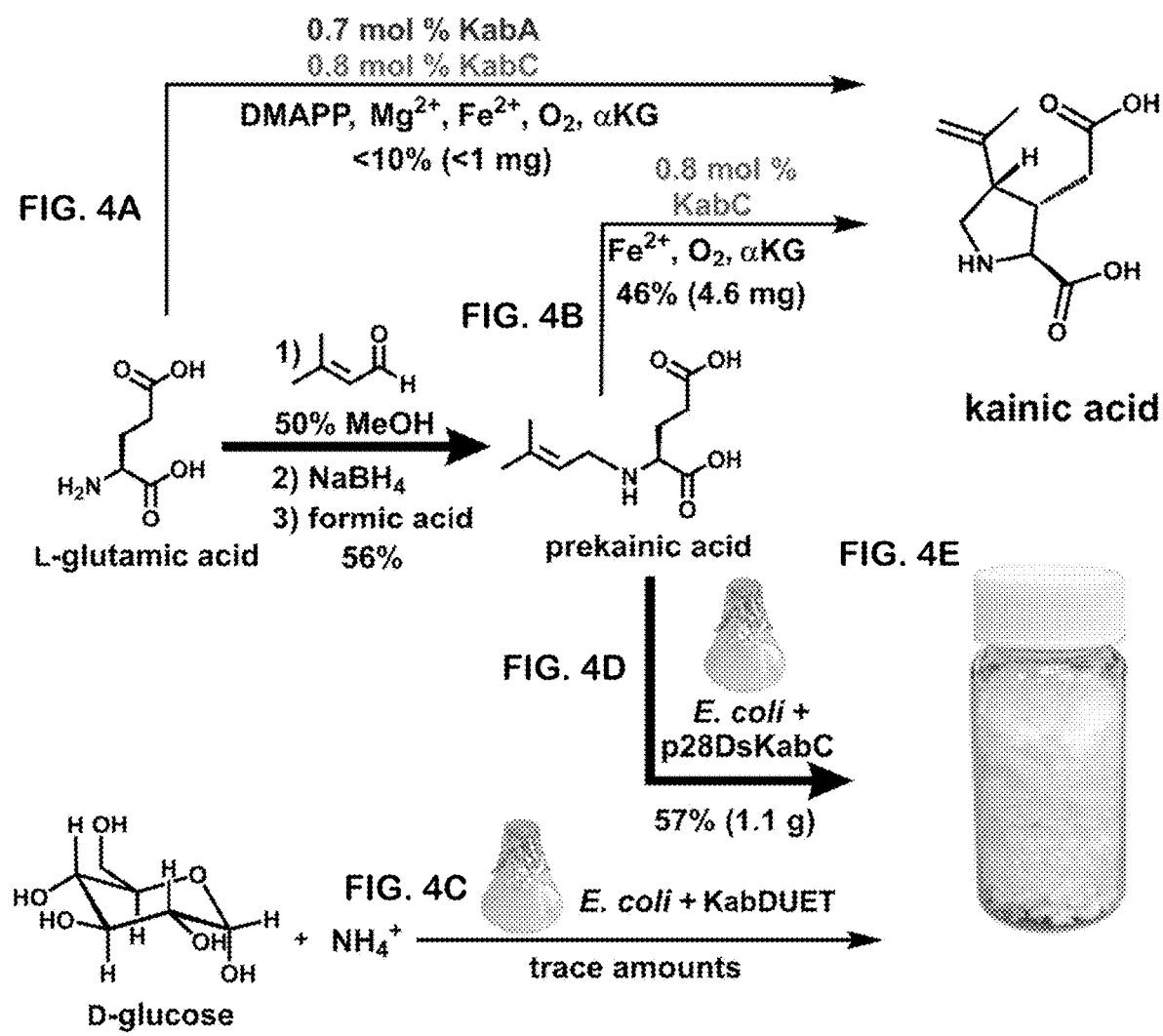
FIGS. 4A-4E show that the discovery of the kainic acid biosynthetic genes enabled new kainic acid production routes
Figure 30:
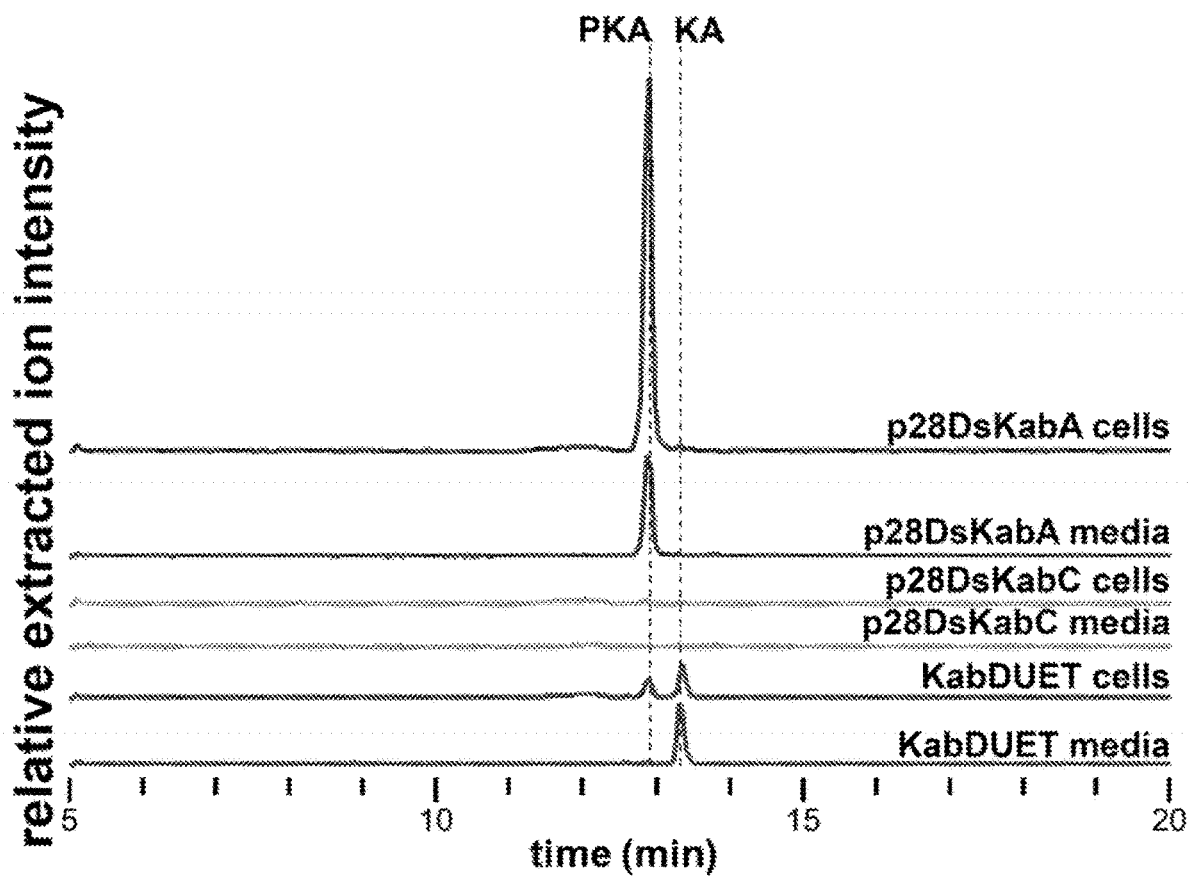
FIG. 30 shows LCMS analyses of lysed cell pellets/M9 media of *E. coli* expressing different DsKab gene combinations. Samples were tested for the presence of both prekainic acid (PKA) and kainic acid (KA). Each trace represents the (M-H)⁻ extracted ion chromatogram for prekainic acid (214.1±0.1 m/z) and kainic acid (212.1±0.1 m/z).

To complement the in vitro production methods, we next aimed to develop an *E. coli* fermentation system (FIG. 4, view (c)). As kainic acid is biosynthesized from the primary metabolites L-glutamate and DMAPP, we reasoned that co-expression of dskabA and dskabC as part of a pETDuet vector (KabDUET) should enable production of kainic acid. Examination of both the cell extract and fermentation media by LCMS, however, indicated only trace amounts of kainic acid (FIG. 30).

Figure 12:
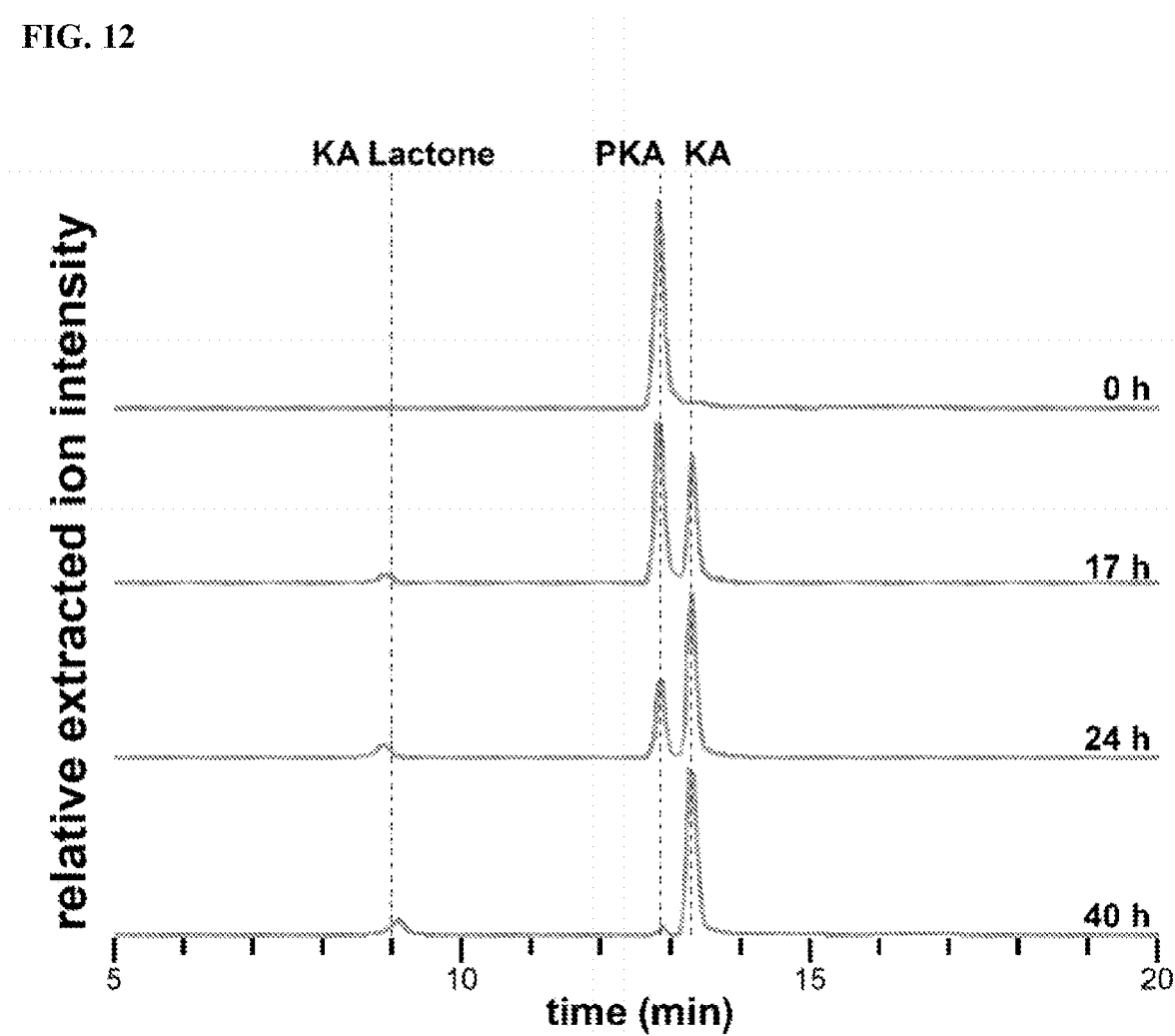
FIG. 12 shows a time course of the conversion of prekainic acid to kainic acid in the media of *E. coli* expressing the dskabC gene on a pET28 vector. Each trace represents the $(M-H)^-$ extracted ion chromatogram for both prekainic acid (214.1±0.1 m/z) and kainic acid (212.1±0.1 m/z).

As the Kab enzymes appeared active within the *E. coli* fermentation conditions, we next evaluated a biotransformation strategy. We had earlier observed kainic acid present both within the cells and the media, while prekainic acid was not observed (FIG. 30). This observation suggested that DsKabA catalyzes the limiting reaction and that kainic acid can exchange between the media and cells by either active or passive transport. Therefore, we explored a biotransformation strategy with synthetic prekainic acid and *E. coli* cells expressing DsKabC (FIG. 4, view (d)). Initially we purified synthetic prekainic acid prior to addition to the *E. coli* culture, but ultimately, we developed a simpler strategy in which we added the entire unpurified crude reaction materials to the *E. coli* medium. After 40 h, we observed nearly complete consumption of an 8 mmol prekainic acid synthetic reaction in a 3×1 L *E. coli* biotransformation to primarily kainic acid and some kainic acid lactone (~10% by ion intensity) (FIG. 12). Employing a simple two-step purification using activated carbon followed by preparatory reversed phase HPLC, we purified 1.1 g of kainic acid from 6 L of minimal media with a combined overall yield of 32% and >95% purity as assessed by NMR.

Discussion

As new DNA sequencing technologies are released, genomes of complex organisms can be assembled more quickly and at relatively low cost. This enables the opportunity to study underexplored classes of organisms. By focusing on a producer of the iconic natural product kainic acid, we have shown that biosynthetic genes can be clustered in red macroalgae. While the enzymatic activities were consistent with our initial hypothesis, the transformations they catalyze remain extremely unusual. N-prenylation is much less common than either C- or O-prenylation and typically utilizes a secondary amine instead of primary amine [35]. To our knowledge, KabA and DabA represent the first examples of N-prenylation of a free amino acid with intriguingly high specificity. Additionally, αKG dioxygenases are most known for hydroxylation, desaturation, chlorination, or epimerization chemistry [36]. The observed C—C bond formation by KabC and DabC was reportedly rare within this family of enzymes, with only a few examples [37,38].

In addition to simply discovering and validating the kainic acid biosynthetic cluster, the short route of biosynthesis presented an excellent opportunity to demonstrate the utility of a natural product biosynthetic enzyme to produce a fine chemical. The global emphasis on developing biocompatible green chemistry positions enzymes to be viable replacements for certain transformations [39]. In particular, reactions that require high levels of stereo- and regiospecificity are ideal candidates for enzymatic biocatalysts. This is exemplified in KabC, which catalyzes the formation of a five-membered ring while installing two stereocenters. Although there are already many scalable synthetic processes for kainic acid, the procedures generally require at least 6 synthetic steps with yields <40% [20,40] and produce environmentally toxic waste products such as heavy metals, cyanides, or halogenated organics. In contrast, the biotransformation approach developed in this work is biocompatible with only unreacted glutamic acid, prenol, and boric acid as the byproducts of the synthetic step and only minimal use of non-aqueous solvents. Furthermore, this procedure is economically attractive, with reagents costing less than 10% of other kainic acid syntheses while also greatly simplifying the purification procedure and remaining scalable. In embodiments, this biotransformation strategy is employed to produce additional kainoids such as domoic acid, and novel kainic acid analogs from synthetic precursors.

Overall, combining genomic information with in vitro enzymatic characterization disclosed herein enabled discovery of the enzymes responsible for the biosynthesis of a seaweed natural product, and also to develop new methods to produce this important research tool.

REFERENCES OF EXAMPLE 1

1. Higa, T. & Kuniyoshi, M. Toxins associated with medicinal and edible seaweeds. J. Toxicol. —Toxin Rev. 19, 119-137 (2000).
2. Nitta, I., Watase, H. & Tomiie, Y. Structure of kainic acid and its isomer, allokainic acid. Nature 181, 761-2 (1958).
3. Murakami, S., Takemoto, T. & Shimizu, Z. Studies on the effective principles of *Digenea simplex* Aq. I. Yakugaku Zasshi 73, 1026-1028 (1953).
4. Komiya, Y. & Kobayashi, A. Techniques applied in Japan for the control of *Ascaris* and hookworm infections—a review. Jpn. J. Med. Sci. Biol. 18, 1-17 (1965).
5. Lee, S. H., Kang, S. C., Ahn, J. H., Lee, J. W. & Rim, H. J. Santonin-kainic acid complex as a mass chemotherapeutic of *Ascaris lumbricoides* control in Korea. Korean J. Parasitol. 10, 79-85 (1972).
6. Tremblay, J.-F. Shortage of kainic acid hampers neuroscience research. Chem. Eng. News 78, 14-15 (2000).
7. Werner, P., Voigt, M., Keinanen, K., Wisden, W. & Seeburg, P. H. Cloning of a putative high-affinity kainate receptor expressed predominantly in hippocampal CA3 cells. Nature 351, 742-4 (1991).
8. Dingledine, R., Borges, K., Bowie, D. & Traynelis, S. F. The glutamate receptor ion channels. Pharmacol. Rev. 51, 7-61 (1999).
9. Hampson, D. R. & Manalo, J. L. The activation of glutamate receptors by kainic acid and domoic acid. Nat. Toxins 6, 153-8 (1998).
10. Lodge, D. The history of the pharmacology and cloning of ionotropic glutamate receptors and the development of idiosyncratic nomenclature. Neuropharmacology 56, 6-21 (2009).
11. Pulido, O. M. Domoic acid toxicologic pathology: A review. Mar. Drugs 6, 180-219 (2008).
12. Konno, K., Hashimoto, K., Ohfune, Y., Shirahama, H. & Matsumoto, T. Acromelic acids A and B. Potent neuroexcitatory amino acids isolated from *Clitocybe acromelalga*. J. Am. Chem. Soc. 110, 4807-4815 (1988).
13. Lelong, A., Hégaret, H., Soudant, P. & Bates, S. S. Pseudo-nitzschia (Bacillariophyceae) species, domoic acid and amnesic shellfish poisoning: revisiting previous paradigms. Phycologia 51, 168-216 (2012).
14. Mos, L. Domoic acid: a fascinating marine toxin. Environ. Toxicol. Pharmacol. 9, 79-85 (2001).
15. Grattan, L. M. et al. Repeated dietary exposure to low levels of domoic acid and problems with everyday memory: research to public health outreach. Toxins (Basel). 10, 103 (2018).
16. Wright, J. L. C. et al. Identification of domoic acid, a neuroexcitatory amino acid, in toxic mussels from eastern Prince Edward Island. Can. J. Chem. 67, 481-490 (1989).
17. Zhu, J., Zheng, X. Y., Zhang, H. L. & Luo, Q. Kainic acid-induced neurodegenerative model: Potentials and limitations. J. Biomed. Biotechnol. 2011, (2011).
18. Ben-Ari, Y., Lagowska, J., Tremblay, E. & Le Gal La Salle, G. A new model of focal status epilepticus: intra-amygdaloid application of kainic acid elicits repetitive secondarily generalized convulsive seizures. Brain Res. 163, 176-9 (1979).
19. Levesque, M. & Avoli, M. The kainic acid model of temporal lobe epilepsy. Neurosci. Biobehav. Rev. 37, 2887-2899 (2013).
20. Stathakis, C. I., Yioti, E. G. & Gallos, J. K. Total syntheses of (−)-α-kainic acid. European J. Org. Chem. 4661-4673 (2012). doi:10.1002/ejoc.201200243
21. Holdt, S. L. & Kraan, S. Bioactive compounds in seaweed: Functional food applications and legislation. J. Appl. Phycol. 23, 543-597 (2011).
22. Brunson, J. K. et al. Biosynthesis of the neurotoxin domoic acid in a bloom-forming diatom. Science 361, 1356-1358 (2018).
23. Michael, T. P. et al. High contiguity *Arabidopsis thaliana* genome assembly with a single nanopore flow cell. Nat. Commun. 9, 1-8 (2018).
24. Boycheva, S., Daviet, L., Wolfender, J. & Fitzpatrick, T. B. The rise of operon-like gene clusters in plants. Trends Plant Sci. 19, 447-459 (2014).
25. Schlapfer, P. et al. Genome-wide prediction of metabolic enzymes, pathways, and gene clusters in plants. Plant Physiol. 173, 2041-2059 (2017).
26. Brawley, S. H. et al. Insights into the red algae and eukaryotic evolution from the genome of *Porphyra umbilicalis* (Bangiophyceae, Rhodophyta). Proc. Natl. Acad. Sci. 114, E6361-E6370 (2017).
27. Matasci, N. et al. Data access for the 1,000 Plants (1KP) project. Gigascience 3, 17 (2014).
28. Saunders, G. W., Jackson, C. & Salomaki, E. D. Phylogenetic analyses of transcriptome data resolve familial assignments for genera of the red-algal Acrochaetiales-Palmariales Complex (Nemaliophycidae). Mol. Phylogenet. Evol. 119, 151-159 (2018).
29. Ramsey, U. P., Bird, C. J., Shacklock, P. F., Laycock, M. V. & Wright, J. L. C. Kainic acid and 1′-hydroxykainic acid from palmariales. Nat. Toxins 2, 286-292 (1994).
30. Monier, A. et al. Horizontal gene transfer of an entire metabolic pathway between a eukaryotic alga and its DNA virus. Genome Res. 19, 1441-9 (2009).
31. Miyasaki, M., Watanabe, H., Takano, T. & Morimoto, A. Studies on the components of *Digenea simplex* Ag. VII. Yakugaku Zasshi 76, 189-191 (1956).
32. Goldberg, O., Luini, A. & Teichberg, V. I. Lactones derived from kainic acid: novel selective antagonists of amino acid-induced Na+ fluxes in rat striatum slices. Neurosci. Lett. 23, 187-91 (1981).
33. Coudert, E., Acher, F. & Azerad, R. A convenient and efficient synthesis of (2S,4R)- and (2S,4S)-4-methylglutamic acid. Synthesis (Stuttg). 1997, 863-865 (1997).
34. Gupta, D., Summers, M. L. & Basu, C. Engineering an isoprenoid pathway in *Escherichia coli* for production of 2-methyl-3-buten-2-ol: A potential biofuel. Mol. Biotechnol. 56, 516-523 (2014).
35. Winkelblech, J., Fan, A. & Li, S. M. Prenyltransferases as key enzymes in primary and secondary metabolism. Appl. Microbiol. Biotechnol. 99, 7379-7397 (2015).
36. Martinez, S. & Hausinger, R. P. Catalytic mechanisms of Fe(II)- and 2-oxoglutarate-dependent oxygenases. J. Biol. Chem. 290, 20702-11 (2015).
37. Siitonen, V. et al. Divergent non-heme iron enzymes in the nogalamycin biosynthetic pathway. Proc. Natl. Acad. Sci. 113, 5251-5256 (2016).
38. Tang, M.-C., Zou, Y., Watanabe, K., Walsh, C. T. & Tang, Y. Oxidative Cyclization in Natural Product Biosynthesis. Chem. Rev. acs.chemrev.6b00478 (2016). doi:10.1021/acs.chemrev.6b00478
39. Sheldon, R. A. & Woodley, J. M. Role of biocatalysis in sustainable chemistry. Chem. Rev. 118, 801-838 (2018).
40. Zhang, M. et al. A short scalable route to (−)-α-kainic acid using Pt-catalyzed direct allylic amination. Chemistry 21, 3937-41 (2015).

Example 2

General Methods

Materials: all materials were purchased from Fisher Scientific, Alfa Aesar, Sigma-Aldrich, or Chem-Impex.

Bacterial growth selection: all bacteria transformed with pET28 were grown in the presence of the corresponding antibiotic kanamycin (50 mg/L).

NMR: NMR spectroscopic data was collected on a Bruker Avance III spectrometer (600 MHz) using either a 1.7 mm inverse detection triple resonance (H-C/N/D) cryoprobe or a 5 mm inverse detection triple resonance (H-C/N/D) cryoprobe or a JEOL spectrometer (500 MHz). All samples were dissolved in D20 and supplemented with 0.1% methanol to serve as a reference standard.

Molecular Biology and Biochemical Methods

DNA Extraction

*Digenea simplex* was collected from Onna, Okinawa Prefecture, Japan. The sample was dried by lyophilization and finely ground. Five hundred milligrams of powder was resuspended in 10 mL of CTAB buffer (3% CTAB, 1.4 M NaCl, 20 mM EDTA, 100 mM Tris-HCl pH 8.0, 0.2% polyvinylpolypyrrolidone, 0.2% β-mercaptoethanol, 1.5 mg/mL RNase A, and 0.2 mg/mL proteinase K) and incubated at 55° C. for 2 hours with gentle mixing every 15 minutes. The cell debris was removed by centrifugation at 14,000×g for 10 minutes at room temperature. The supernatant was transferred and 2 mL of 5 M potassium acetate pH 8.0 was added. The mixture was gently mixed and cooled on ice for 30 minutes then centrifuged at 14,000×g for 15 minutes at 4° C. The supernatant was removed and extracted with one equivalent of phenol:chloroform:isoamyl alcohol 25:24:1 saturated with 10 mM Tris, pH 8.0, 1 mM EDTA. The mixture was centrifuged at 12,000×g for 5 minutes at 4° C. The aqueous layer was transferred to a new tube and extracted with one equivalent of chloroform and centrifuged at before. The aqueous layer was transferred and one equivalent of cold isopropanol was added and carefully mixed. The mixture was centrifuged at 12,000×g for 15 minutes at 4° C. The supernatant was removed and the pellet was carefully washed with 75% ethanol. The pellet was dried to remove the ethanol and carefully resuspended in 250 μL of elution buffer (10 mM Tris-HCl pH 8.0). To further remove RNA, 300 μg of RNase A was added and incubated at room temperature for 1 hour prior to incubation at 4° C. overnight. The RNase A treated DNA was extracted with phenol:chloroform:isoamyl alcohol 25:24:1 saturated with 10 mM Tris, pH 8.0, 1 mM EDTA followed by chloroform extraction as before. Sodium acetate (pH 5.2) was added to a final concentration of 0.3 M followed by three equivalents of cold ethanol and carefully mixed. The mixture was incubated at −20° C. for 2 hours and centrifuged at 16,000×g for 20 minutes at 4° C. The pellet was washed with 75% ethanol and dried. The pellet was resuspended with 100 μL elution buffer and further purified by a PippinHT with >8,000 bp size selection. *Palmaria palmata* was collected from Wallace Cove Lighthouse, Bay of Fundy, New Brunswick, Canada and dried in silica gel. The sample was further dried by lyophilization and ground into a powder. DNA was extracted in a similar manner to the previous method, except 20 mL of CTAB buffer was used for 500 mg of *P. palmata* powder and RNase A was omitted. Because RNA was not completely digested after the overnight incubation an additional 100 μg of RNase was added and further incubated as before. DNA was directly used for sequencing without a PippinHT purification step. between ppkabA and ppkabC and with different gene ori

Genome Sequencing

The high molecular weight (HMW) *D. simplex* and *P. palmata* DNA was sequenced by running on an Oxford Nanopore MinION or GridION sequencer (Oxford Nanopore Technologies, Oxford, UK). A one-dimensional (ld) library was prepared with 1.2 μg DNA using the Ligation Sequencing Kit (SQK-LSK109, Oxford Nanopore Technologies, Oxford, UK). The libraries were loaded on a R9.4 flowcell and run for 48 hr resulting in 6.7 Gb of sequencing with a read length N50 of 7.2 kb and 4.7 Gb of sequencing with a read length N50 of 8 kb for *D. simplex* and *P. palmata* respectively. Since the HMW DNA generated both long reads (good distribution) and throughput, 1 μg of DNA was used to make Id library for the PromethION (Oxford Nanopore Technologies, Oxford, UK) for *D. simplex*. The resulting sequencing run produced 47 Gb of sequence with a read length N50 of 7 kb.

Illumina Sequencing

NEBnext sequencing libraries were generated to polish the genome assemblies (New England Biolabs, Beverly, MA, USA). NEBnext sequencing libraries were created with 100 ng of DNA and quality controlled on a bioanalyzer. The resulting libraries were sequenced on an Illumina MiSeq 2×150 bp to check quality and quantity (Illumina, San Diego, CA). The libraries were then sequenced on an Illumina NovaSeq6000 2×150 bp run that resulted in 19 and 34 Gb of sequence for *D. simplex* and *P. palmata* respectively.

Genome Assembly

Sequencing reads resulting from the PromethION (47 Gb) were assembled using a correctionless overlap-layout-consensus strategy was taken to assemble the genome [1]. The resulting raw reads in fastq format were aligned (overlap) with minimap [2] and an assembly graph (layout) was generated with miniasm [3]. The resulting graph was inspected using Bandage [4]. A consensus sequence was generated by mapping reads to the assembly with minimap, and then Racon [5] three times. Finally, the assembly was polished with pilon [6] three times using the Illumina pairedend 2×150 bp sequence; the Illumina reads were mapped to the consensus assembly using minimap2.

P. palmata Kab Cluster

The 4.7 Gb of ONT sequence generated on the GridION for P. palamta was used to search for long reads containing the ppkab cluster. The fastq file was transformed to a fasta file and made into a blast database. The DsKab genes were then used to search the long-read blast database by tblastn and a 44 kb read was identified with the ppkab cluster. A consensus sequence was generated by mapping reads to the single 44 kb read with minimap [2], and then Racon [5] two times. Polishing with Illumina reads was attempted on the 44 kb consensus read but the ppkab cluster was flanked by repeat elements with 60,000 and 100,000-fold coverage, which resulted in poor polishing. Therefore, only the kab cluster was polished with pilon [6] five times using the Illumina paired-end 2×150 bp sequence.

PCR and Cloning

PCR of the Kab genes was performed with PrimeSTAR HS DNA Polymerase (Takara) according to the manufacturer's instructions using either genomic DNA or codon optimized synthetic genes as a template. pET28-MBP (Maltose Binding Protein)-TEV and pET28 vectors were amplified using PrimeSTAR MAX DNA Polymerase (Takara). PCR products were purified by agarose gel extraction and assembled into expression vectors using NEBuilder HiFi DNA Assembly mix and transformed into *E. coli* DH5a cells. Construction of vectors was confirmed by Sanger sequencing. The pET28-MBP-TEV vector produced proteins with a His$_6$-MBP-His$_6$ N-terminal tag and the pET28 vector produced proteins with a His$_6$ N-terminal tag. See Table S1 and S2 for a list of primers and synthetic genes respectively.

TABLE S1 primers used in this example.

| Name | Sequence | SEQ ID NO: |
|---|---|---|
| DsKabA p28 For | GGTGCCGCGCGGCAGCCATATGAGTATTAC CACTATGAAAGGAGTTACATC | 21 |
| DsKabA p28 Rev | GGTGGTGGTGGTGCTCGAGTTAATTTGTCGC CTTGAGTTTCTTAAAG | 22 |
| DsKabC p28 For | GGTGCCGCGCGGCAGCCATATGACAGTAAG TAAGTACAACGGTGTTG | 23 |
| DsKabC p28 Rev | GGTGGTGGTGGTGCTCGAGTTAAAGGTAGT ATCCTTCATGAAATTTG | 24 |
| GfKabC MBP For | CTGTACTTCCAATCCGGATCCATGACTTCTT TCGATTTCGTCGCTAAGACTTTC | 25 |
| GfKabC MBP Rev | GGTGGTGGTGGTGCTCGAGTTAGACGTAGT ACCCCGAGTGAAACTTTGC | 26 |
| PpKabC MBP For | CTGTACTTCCAATCCGGATCCATGCCTGTGT ATAATGGTACGTCACAAGC | 27 |
| PpKabC MBP Rev | GGTGGTGGTGGTGCTCGAGTTACAGGTAGT AACCTTCATGGAATTTGTTCTTG | 28 |
| ReKabC MBP For | CTGTACTTCCAATCCGGATCCATGGCGGTGT ACAATGGCGTCTCGCAGG | 29 |
| ReKabC MBP Rev | GGTGGTGGTGGTGCTCGAGCTATAGATAAT AGCCCTCGTGGAACTTATTTTTCACG | 30 |
| pET28 Up | CATATGGCTGCCGCGCGGCACC | 31 |
| pET28 Down | CTCGAGCACCACCACCACCACCACTGAG | 32 |

TABLE S2

Synthesized genes used in this study were purchased as codon optimized gBlocks from IDT.

| Name | Sequence | SEQ ID NO: |
|---|---|---|
| PpKabC | ATGCCTGTGTATAATGGTACGTCACAAG CATTCAATTTTGCGCCGCTGCACCCAGATAGTT TGAATTGGTGCCCAAAGTCGAGTCTTCCTCCAG AAATTCCTGTAGTGGATCTGTCAAAACTTAATT CTGAAGCCGAGCTGGCACAATTTCTTGTGGACA TTCGTAAGAGCGGGTTGTTTTATGTAGTCAATC ATGGTGTCCCGGAAGAACTTTCTATTGGGTGTT ACAATCGCTTCCGTCAATTCTGTAACATTCCTG AGGACCAACGTGCGGAATACTCGACCGACCAT CATTTTGTAAACGGGGCTACATGCCGTATAAG AGTTCCAGCATCGGCAAGGCAAATAAAGGTAA ATCTCAAAAGGACTTTGTGGTTAAATACTTCTG GCGTGGACCGCGCGTTGAGAACCGTAGTCCGG ATGCTGATTTCAAGAGCTATCACGACGAATACC ACCGTCGCACAGCTGATATCGCTAACAGCGTGA TTACTAAAATTCTTCAGGCCCTGACGACGCGTT TTCCTGACTTTGACCCTGCTGAATATAAAGATA ACATTAATTCCCATCATATGTTCTTCTCGAACCG CCTTTACCCAGACAACGAACCTGAGAAAGGCG AGAATGTAGAATACCGTTTAGTACCGCACCGTG ACCTGAGCTTCGTGACCCTTGCTCACCAAATCC CGGCGGACAACGGTTACCAAGGCCTTTTCGTTT TTACCGGCGATGGGAAGAAGGTTTGCGTGCCTC CGATTCGTAACAGCTATCTTGTCTTCATGGGAC AGGCAATGTCGTATCTGACGAATAAGTACTTAC CTGCAGGGTTGCATGGCGTGGATTTTCCTGAAA | 33 |

TABLE S2-continued

Synthesized genes used in this study were purchased as codon optimized gBlocks from IDT.

| Name | Sequence | SEQ ID NO: |
|---|---|---|
|  | AGAACTGTTTCGAGGGGTCTGAACGCTCCTCTC<br>TTATCTCATTTTACGAACCTCACGATCATATGAT<br>GCCCAGCAAAGCACTTACACCTAAGGATGATG<br>AGATCTTCGATCGTGGTTGTTCGTTCTTTGATGA<br>CATCGGCGTGGACAAAACAGGGACGACCTATA<br>TGTATGTCAAGAACAAATTCCATGAAGGTTACT<br>ACCTGTAAG |  |
| GfKabC | ATGACTTCTTTCGATTTCGTCGCTAAGAC<br>TTTCGATTTTGCTCCCGTCAAAGCTGACGAGTT<br>GAAGTGGTATCCACGTTCCGCGTTACCACCAGA<br>AATTCCTGTAATTGATTTGAACAACGTCAATAC<br>GGAGGAGGAGCTTGCACAGTTCCTGGTGGACA<br>TCCGCAAGTCTGGACTTTTCTACGTTGTCAACC<br>ACGATATCCCGGAGGAAATCTCAATCCAGACGT<br>ACAACGAATTTCGTGAGTTTTGTAAATTGCCAG<br>AAGAGGCCCGCCAAAAATACAATACTGATCGC<br>TGCTTCTTCAATGGGGATATGTTCCATTCAAA<br>GCCACGAGCATTAATGGGGTAATAAGAACAA<br>ACAGCAACGCGACTTTGTCGTGAAGTTTTTCTG<br>GCGCGGCCCACACGTGGTCAATCGTTCCCCCAA<br>TGAACGCTTTGCCAAATGGCACCATCAGTATCA<br>TACACGCACTGCTGAATTAGGTGAAAAGGTCAT<br>GACCACAATCGCAAAAGCTTTGAAGACGCGCTT<br>TCCTGACTTCGACCCGGCCGAACTGGAGGACAA<br>TGTGAACCCTCACAACATGATTTTTTCTAACCG<br>CATTTATCCGGAATTCCCACCCAGTGAAGGGGA<br>GGATGCTGAGTATCGCCTGACCCCCCACCGTGA<br>TATTTCCTACATTACCCTTGTGAATCAGACTCCT<br>GCCAATAACGGATTCAAAGCATTATTTATCGTA<br>ACCGGGGACGGCGAACGCGTTTACGTCCCTCCT<br>ATCCGCAACTCTTACTTGGTATTCATCGGGCAG<br>AGCTTGAGCTACCTTACCAATAAATACCTTCCA<br>GCGGCACTTCACGGGGTCGCTTTTCCGGACGGC<br>AATCTTGAGGGTTGCGAGCGTGCCTCACTGGTG<br>TCTTTCTATGAACCGTATGATCGCATGGTCCCA<br>TCGAAAAATATCAAACCAACGGCAGAAGAGAT<br>CGCTCCAAAATCCTGCTCCTTCTATGATTCGATT<br>GGGTGTGACAAGACAGGAACTACCTTTACTGAT<br>GTTCGTGCAAAGTTTCACTCGGGGTACTACGTC<br>TAA | 34 |

*Digenea simplex* Kainic Acid Extraction

Twenty milligrams of *D. simplex* were finely ground and soaked in 300 mL of distilled water for 2 h at 55° C. The sample was filtered and the flow through was analyzed by an Agilent Technologies 1200 Series system with a diode-array detector coupled to an Agilent Technologies 6530 accurate-mass Q-TOF LCMS using the following method on a Synergi Polar-PP 4μ. 250×4.6 mm column at 0.75 mL/min: 0% B (4.5 min), 0 to 5% B (0.5 min), 5 to 26% B (9 min), 26 to 80% B (9 min), 80 to 100% B (1 min), 100% B (1.5 min), 100 to 0% B (2.5 min), 0% B (2 min), wherein A=0.10% aqueous formic acid, and B=0.10% formic acid in acetonitrile. HRMS (ESI) calculated for prekainic acid ($C_{10}H_{16}NO_4^-$) 214.1085, found 214.1078 (M-H)$^-$; kainic acid ($C_{10}H_{14}NO_4^-$) 212.0928, found 212.0936 (M-H)$^-$; and kainic acid lactone ($C_{10}H_{14}NO_4^-$) 212.0928, found 212.0922 (M-H)$^-$.

Protein Purification

*E. coli* BL-21 co-transformed with the protein expression plasmid were shaken 37° C. in 1 L of terrific broth to an $OD_{600}$~0.8 and then cooled at 18° C. for 1 h before addition of 0.5 mM IPTG for pET28 vectors or 0.2 mM IPTG for MBP vectors. The flasks were shaken overnight and harvested by centrifugation the following morning to remove the media. The cells were resuspended in 25 mL of suspension buffer (500 mM NaCl, 20 mM Tris pH 8.0, and 10% glycerol) and lysed by sonication with a Qsonica 6 mm tip at 40% amplitude for 12 cycles of 15 seconds on and 45 seconds off. The cell lysate was centrifuged at 14,000×g for 25 minutes to removed insoluble debris. The cleared lysate was loaded at 2 mL/min onto a 5 mL HisTrap FF column (GE Healthcare Life Sciences) that was pre-equilibrated with buffer A (1 M NaCl, 30 mM imidazole, and 20 mM Tris pH 8.0) using an ÄKTA FPLC (GE Healthcare Life Sciences). After loading, the column was washed with 40 mL of buffer A. Protein was eluted using a linear gradient of 0-100% buffer B (1 M NaCl, 250 mM imidazole, and 20 mM Tris pH 8.0) over 40 mL and 5 mL fractions were collected. The fractions were analyzed by SDS-PAGE and fractions with at least 90% purity were combined. For the KabC proteins, 2 mM EDTA was added to remove any metals bound in the active site. If the $His_6$ tag was to be removed, 60 units of thrombin were added and incubated overnight at 4° C. Complete cutting was confirmed by SDS-PAGE. Protein was concentrated using Amicon Ultra Centrifugal Filters and further purified by gel filtration using a either a HiLoad 16/60 Superdex 75 or 200 prep grade gel filtration column (GE Healthcare Life Sciences) preequilibrated with 300 mM KCl and 50 mM HEPES pH 8.0. If the protein was to be frozen following gel filtration, 10% glycerol was also added.

Enzymatic Activity Assays

To test DsKabA activity and substrate specificity, a 50 μL reaction containing 5 mM $MgCl_2$, 5 mM amino acid (L-Glu, D-Glu, L-Gln, L-Asp, L-Asn, or Gly), 1 mM prenyl donor (DMAPP or GPP), and 20 μM DsKabA in a buffer of 300 mM KCl and 50 mM HEPES pH 8.0 was incubated at 23° C. for 5 h. One equivalent of 0.1% formic acid in $H_2O$ was added and filtered with a VWR PES 3 k 500 μL spin column. The flow through was analyzed by an Agilent Technologies 1200 Series system with a diode-array detector coupled to an Agilent Technologies 6530 accurate-mass Q-TOF LCMS using the following method on a Synergi Polar-RP 4μ 250×4.6 mm column at 0.75 mL/min: 0% B (4.5 min), 0 to 5% B (0.5 min), 5 to 26% B (9 min), 26 to 80% B (9 min), 80 to 100% B (1 min), 100% B (1.5 min), 100 to 0% B (2.5 min), 0% B (2 min), wherein A=0.1% aqueous formic acid, and B=0.1% formic acid in acetonitrile. For KabC activity and substrate specificity assays, 50 μL reactions containing 5 mM αKG, 1 mM L-ascorbic acid, 1 mM substrate (prekainic acid, NGG, or cNGG) 30 μM ferrous sulfate, and 20 μM KabC in a buffer of 300 mM KCl and 50 mM HEPES pH 8.0 were incubated at 23° C. for 5 h. One equivalent of 0.1% formic acid in $H_2O$ was added and filtered as before. The flow through was analyzed using the same methodology as DsKabA.

DsKabA Prekainic Acid Reaction Scaleup and Purification

A 5 mL reaction of 30 μM $His_6$-DsKabA, 5 mM L-Glu, 10 mM $MgCl_2$, and 5 mM DMAPP in a buffer of 300 mM KCl and 50 mM HEPES pH 8.0 was incubated at 22° C. for 18 h. The protein was separated from the reaction using a 30 kDa Amicon Ultra Centrifugal Filter and washed to recover all small molecule products. The collected flow through was lyophilized and resuspended in 0.1% aqueous formic acid before being purified by preparative RP-HPLC (Agilent PrepStar and ProStar 410 HPLC) using a Phenomenex Luna 5μ C18(2), 100×21.2 mm column at a flow rate of 10 mL/min with the following method: 2% B (5 min), 2 to 20% B (10 min), 20 to 95% B (1 min), 95% B (4 min), 95 to 2% B (2 min), 2% B (3 min), wherein A=0.1% aqueous formic acid, and B=0.1% formic acid in acetonitrile. Absorbance at 210 nm was monitored and the major peak was collected. Acetonitrile was removed by rotary evaporation before lyophilization to afford prekainic acid (3.7 mg, 56% yield) as a white powder. 1H NMR (599 MHz, $D_2O$) δ 5.22 (t, J=7.3 Hz, 1H), 3.64 (t, J=6.7 Hz, 2H), 3.61 (t, J=6.4 Hz, 1H), 2.55-2.42 (m, 2H), 2.12 (ddt, J=13.7, 7.3, 7.3 Hz, 1H), 2.03 (dtd, J=14.3, 7.3, 6.9 Hz, 1H), 1.76 (s, 3H), 1.68 (s, 3H). $^{13}$C NMR (151 MHz, $D_2O$): δ 177.6, 173.3, 144.8, 113.0, 60.2, 44.5, 30.5, 25.4, 25.4, 17.7; HRMS (ESI) calculated for $C_{10}H_{16}NO_4^-$ 214.1085, found 214.1088 (M-H)$^-$.

DsKabC Kainic Acid Reaction Scaleup and Purification

A 7.5 mL reaction of 30 μM $His_6$-DsKabC, 5 mM prekainic acid, 10 mM αKG, 2 mM L-ascorbate, and 50 μM ferrous sulfate in a buffer of 300 mM KCl and 50 mM HEPES pH 8.0 was incubated at 22° C. for 18 h. The protein was separated from the reaction using a 30 kDa Amicon Ultra Centrifugal Filter and washed to recover all small molecule products. The collected flow through was lyophilized and resuspended in 0.1% aqueous formic acid before being purified by preparative RP-HPLC (Agilent PrepStar and ProStar 410 HPLC) using a Phenomenex Luna 5μ C18(2), 100×21.2 mm column at a flow rate of 10 mL/min with the following method: 2% B (5 min), 2 to 20% B (10 min), 20 to 95% B (1 min), 95% B (4 min), 95 to 2% B (2 min), 2% B (3 min), wherein A=0.1% aqueous formic acid, and B=0.1% formic acid in acetonitrile. Absorbance at 210 nm was monitored and the major peak was collected. Acetonitrile was removed by rotary evaporation before lyophilization to afford kainic acid (4.5 mg, 46% isolated yield) as a white powder. $^1$H NMR (599 MHz, $D_2O$) δ 5.01 (s, 1H), 4.73 (s, 1H), 4.07 (d, J=3.0 Hz, 1H), 3.60 (dd, J=11.9, 7.3 Hz, 1H), 3.40 (dd, J=11.5, 11.5 Hz, 1H), 3.09-3.02 (m, 1H), 3.02-2.95 (m, 1H), 2.43 (dd, J=16.6, 6.4 Hz, 1H), 2.34 (dd, J=16.6, 8.4 Hz, 1H), 1.73 (s, 3H). $^{13}$C NMR (151 MHz, $D_2O$): δ 176.9, 173.6, 140.3, 113.6, 66.5, 46.8, 46.2, 40.8, 33.5, 22.1; HRMS (ESI) calculated for $C_{10}H_{14}NO_4^-$ 212.0928, found 212.0929 (M-H)$^-$.

GfKabC Kainic Acid Lactone Reaction Scaleup and Purification

Figure 13:
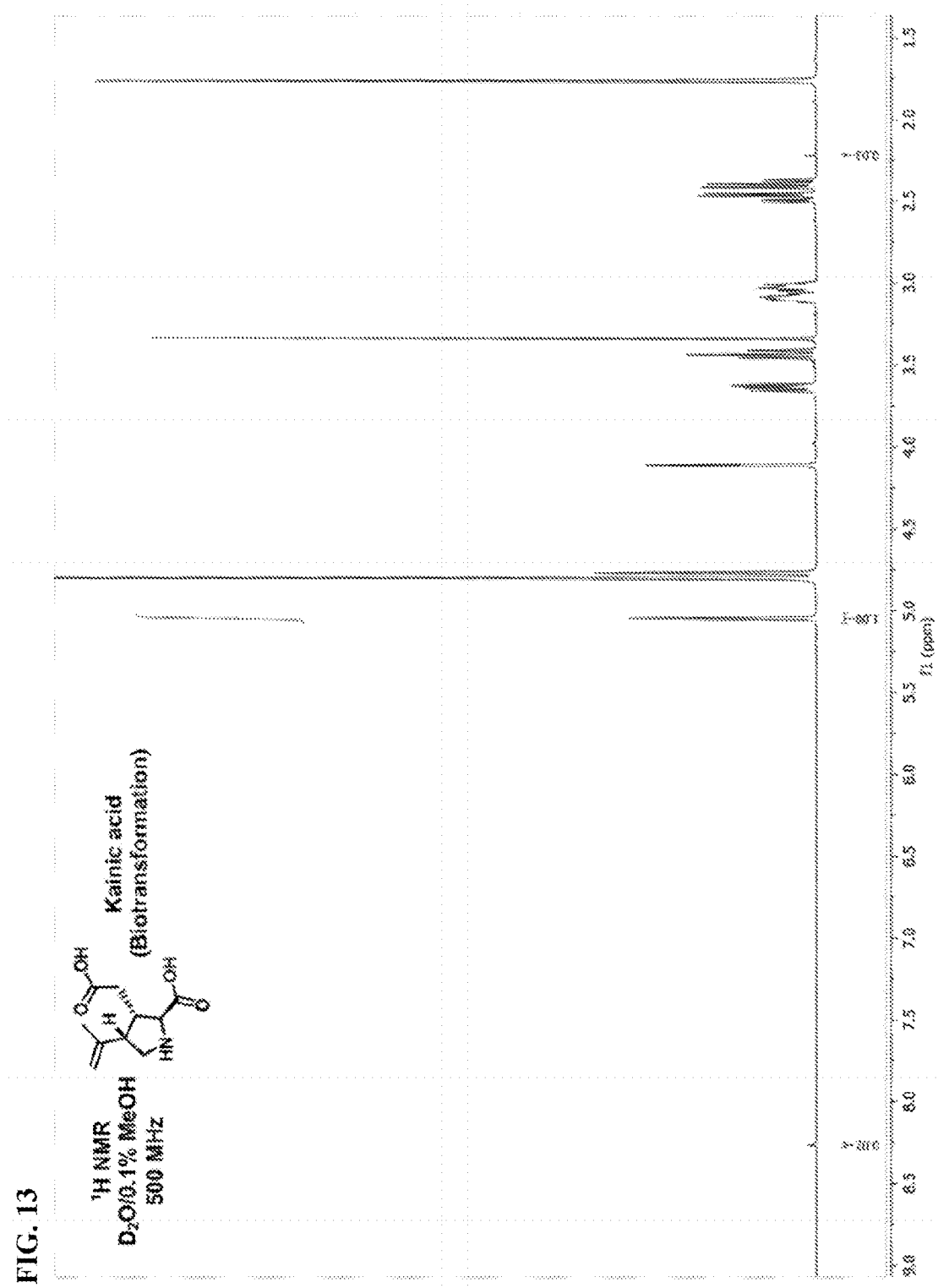
FIG. 13 shows results illustrating the purity of kainic acid isolated from biotransformation by *E. coli*, as tested by $^1$H NMR.
Figure 16:
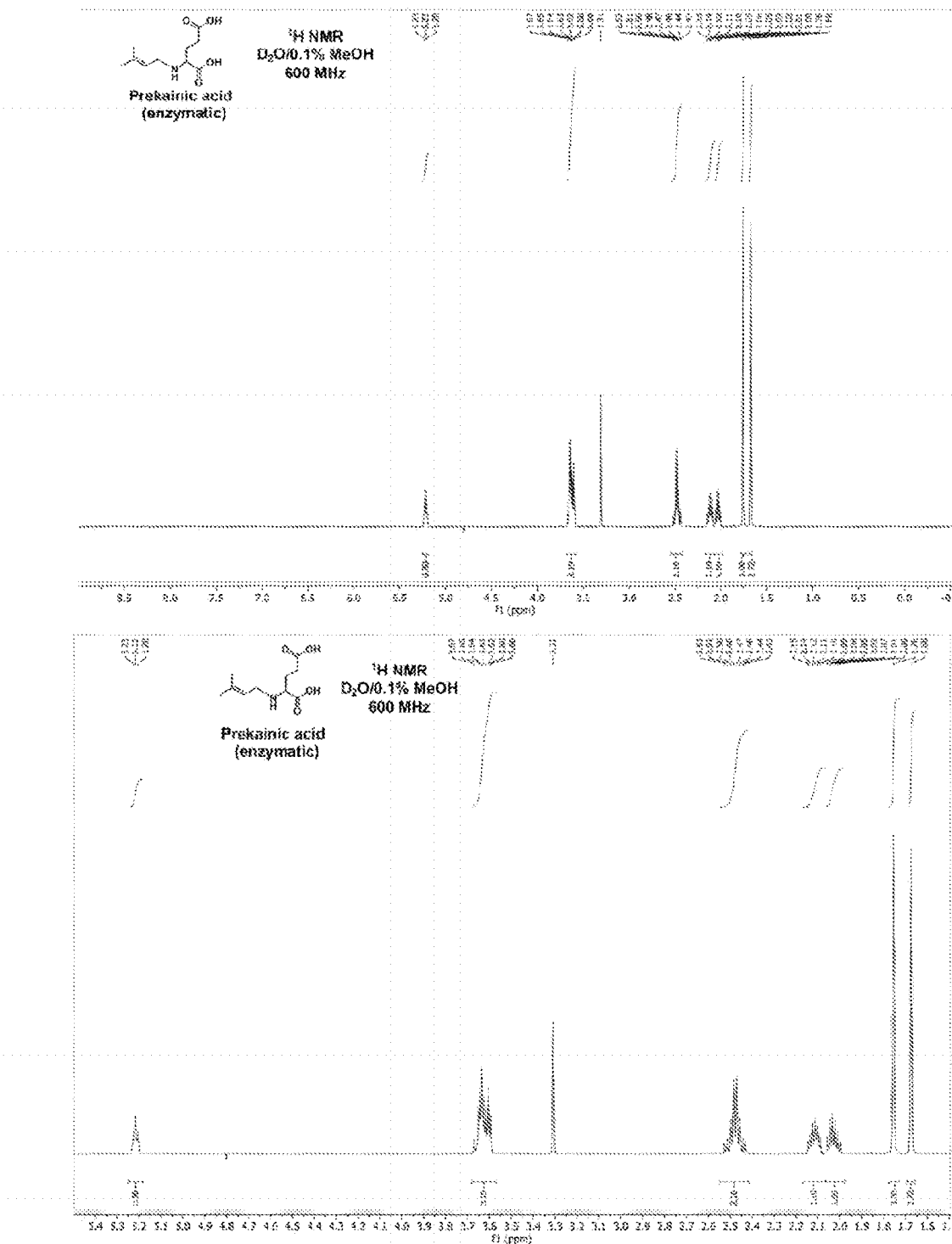
FIG. 16 shows $^1$H NMR analysis of prekainic acid (DsKabA enzymatic product).
Figure 18:
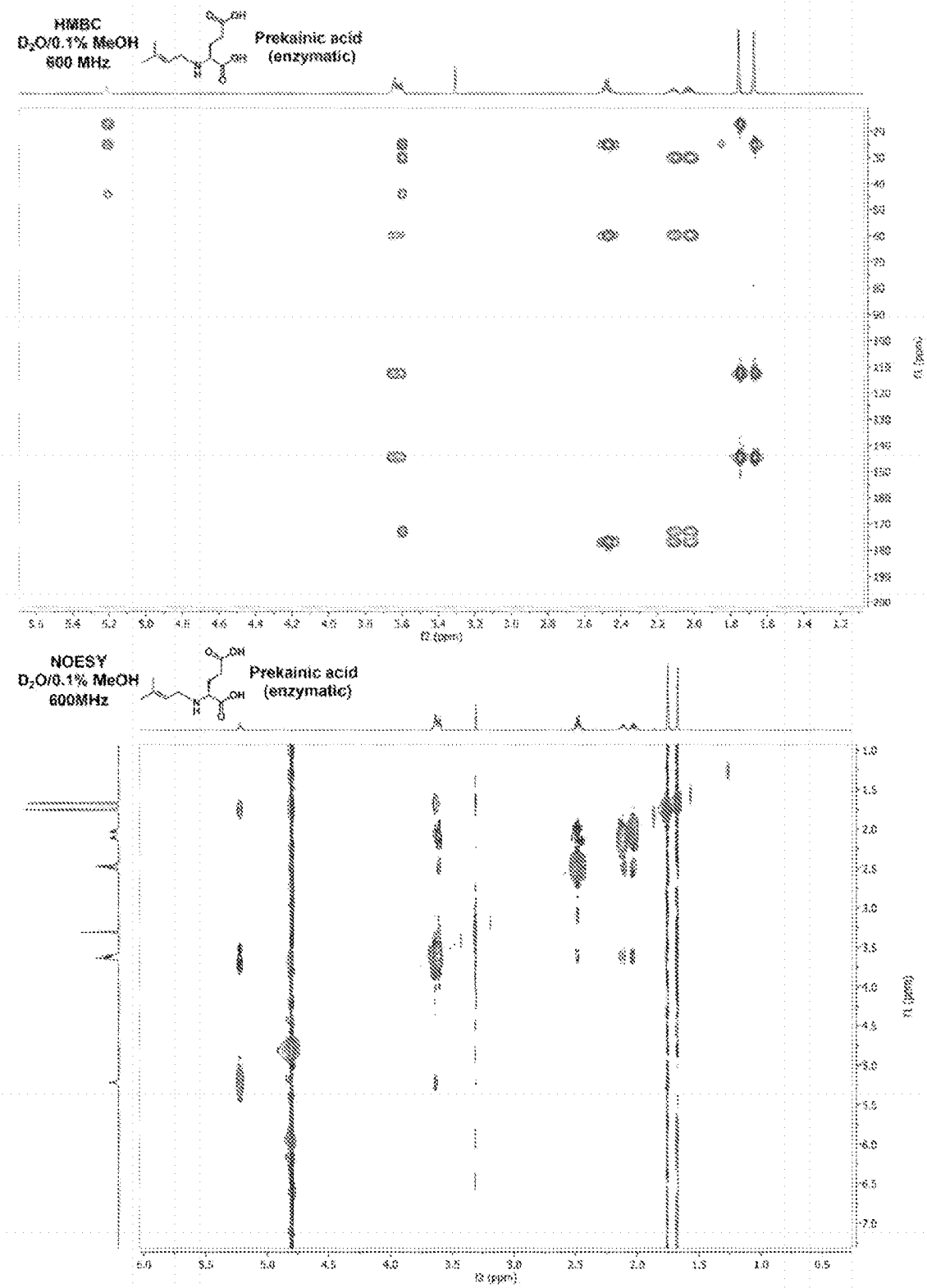
FIG. 18 shows HMBC and NOESY analysis of prekainic acid (enzymatic product).
Figure 19:
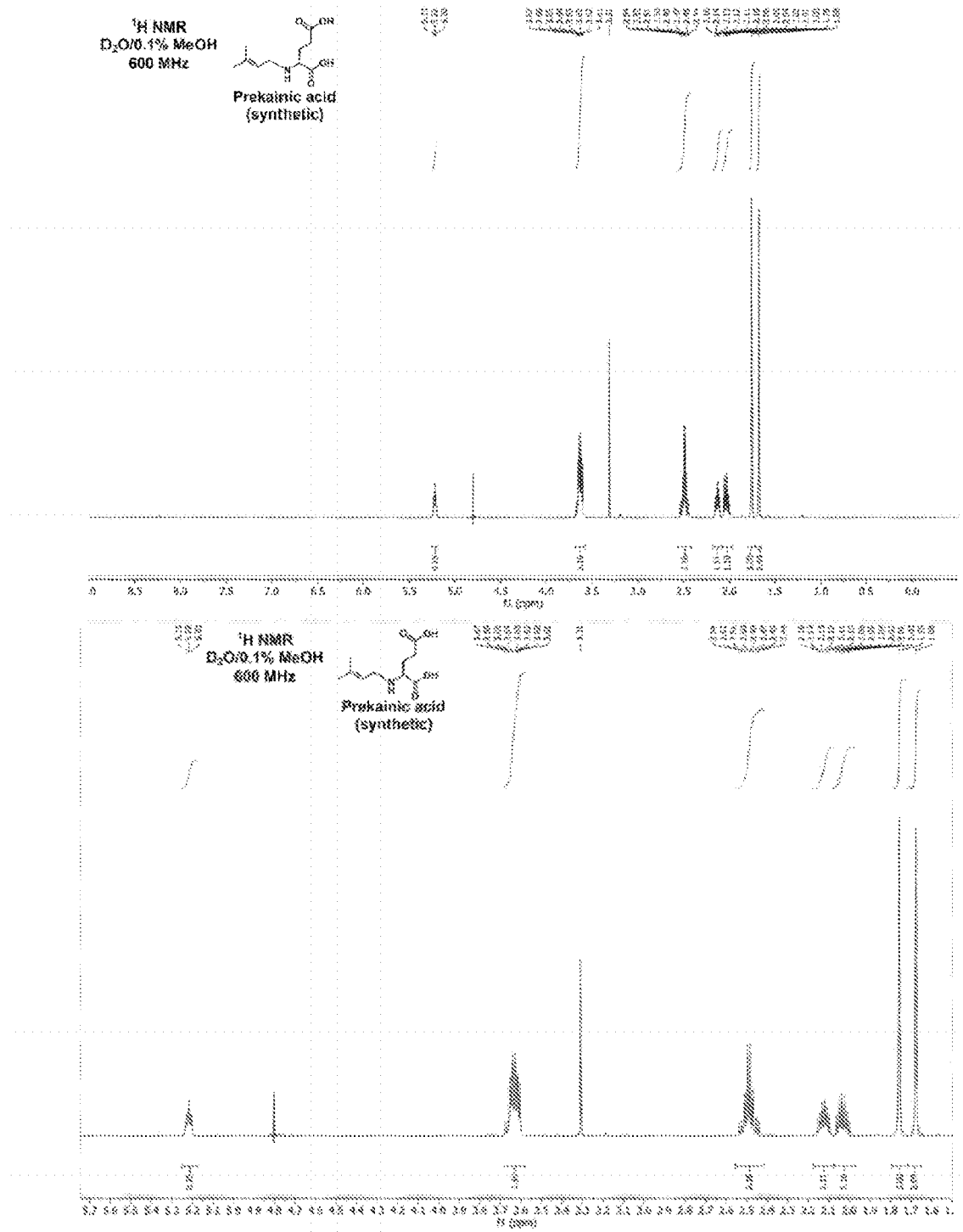
FIG. 19 shows $^1$H NMR analysis of prekainic acid (synthetic product).
Figure 20:
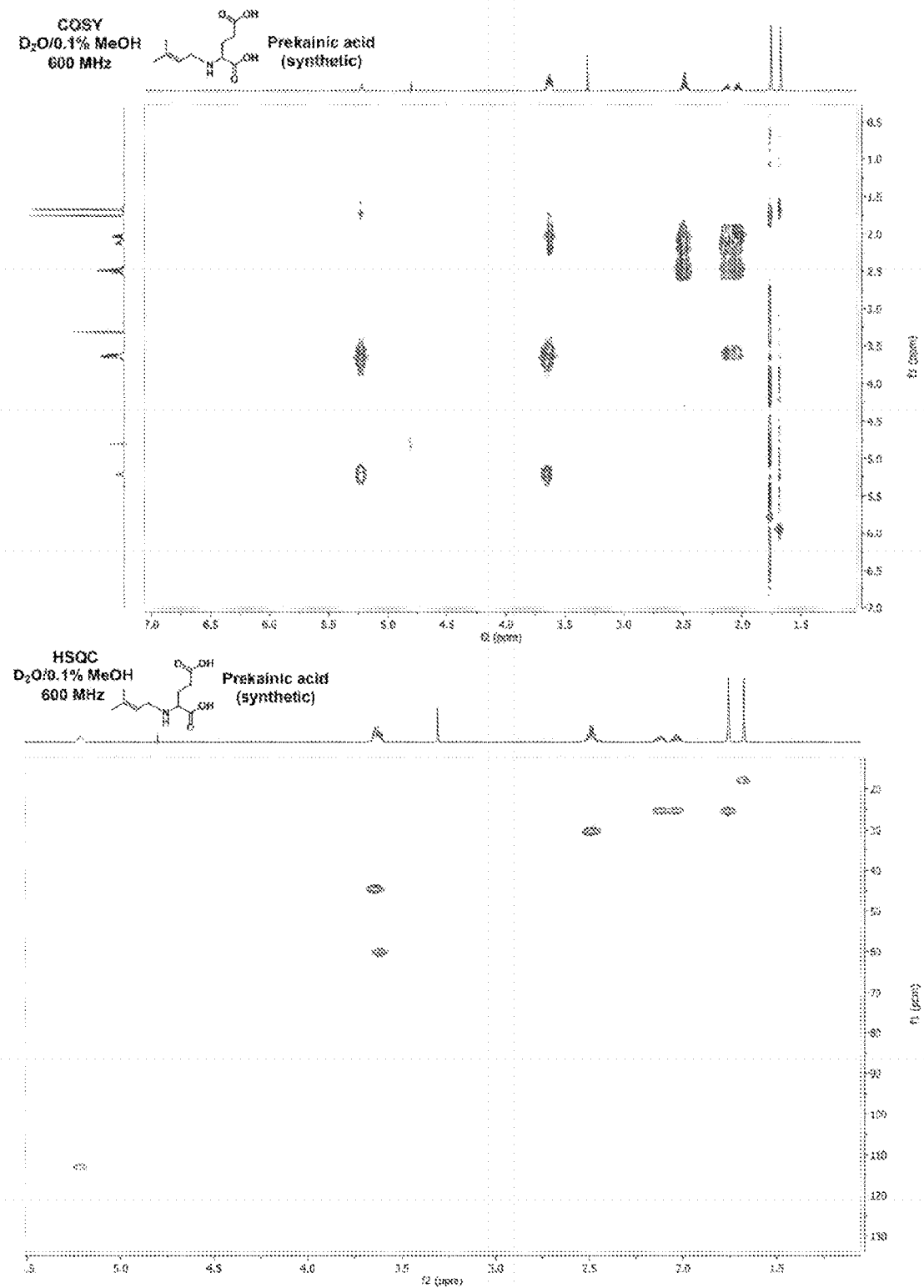
FIG. 20 shows COSY and HSQC analysis of prekainic acid (synthetic product).
Figure 21:
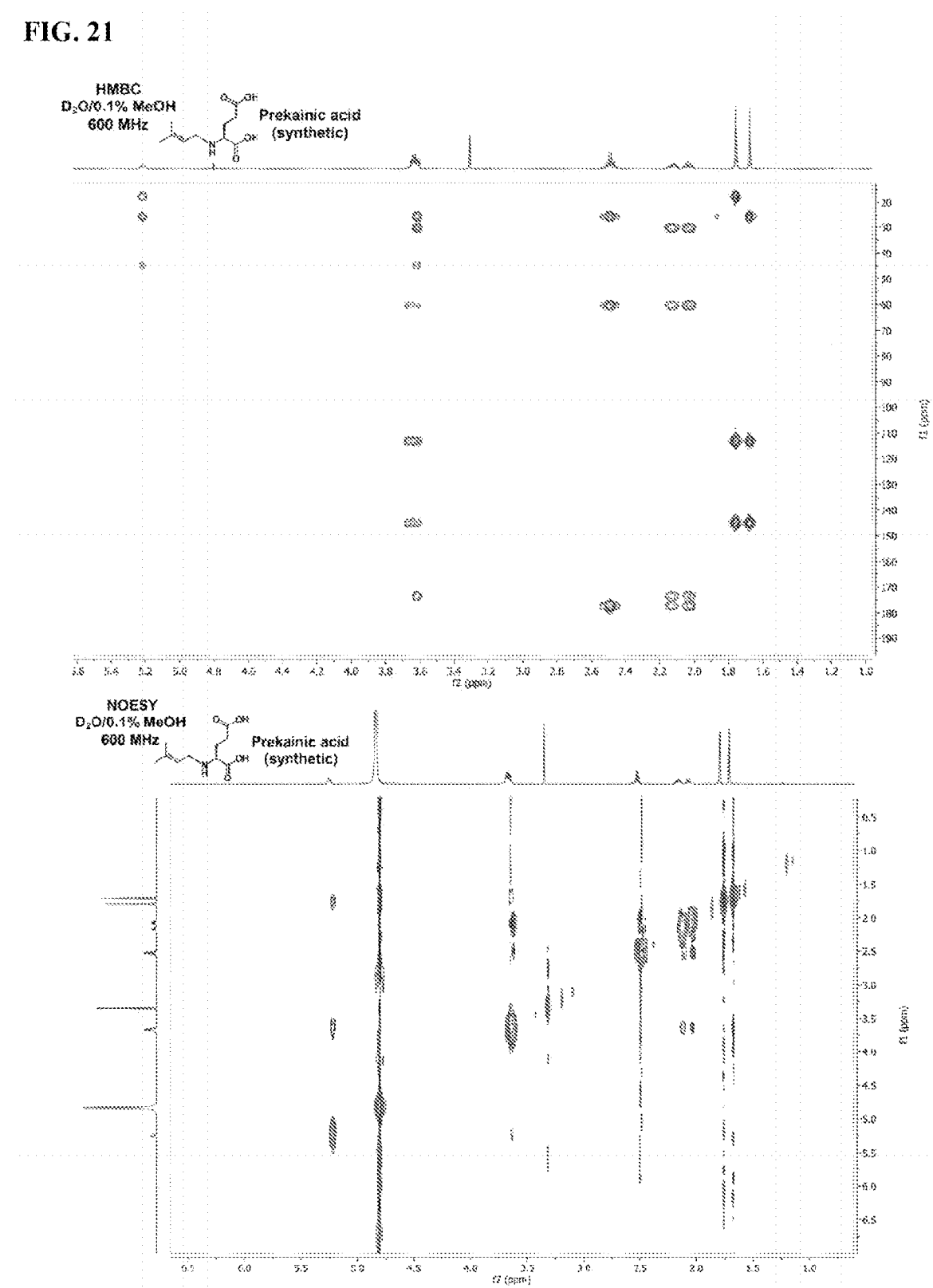
FIG. 21 shows HMBC and NOESY analysis of prekainic acid (synthetic product).
Figure 22:
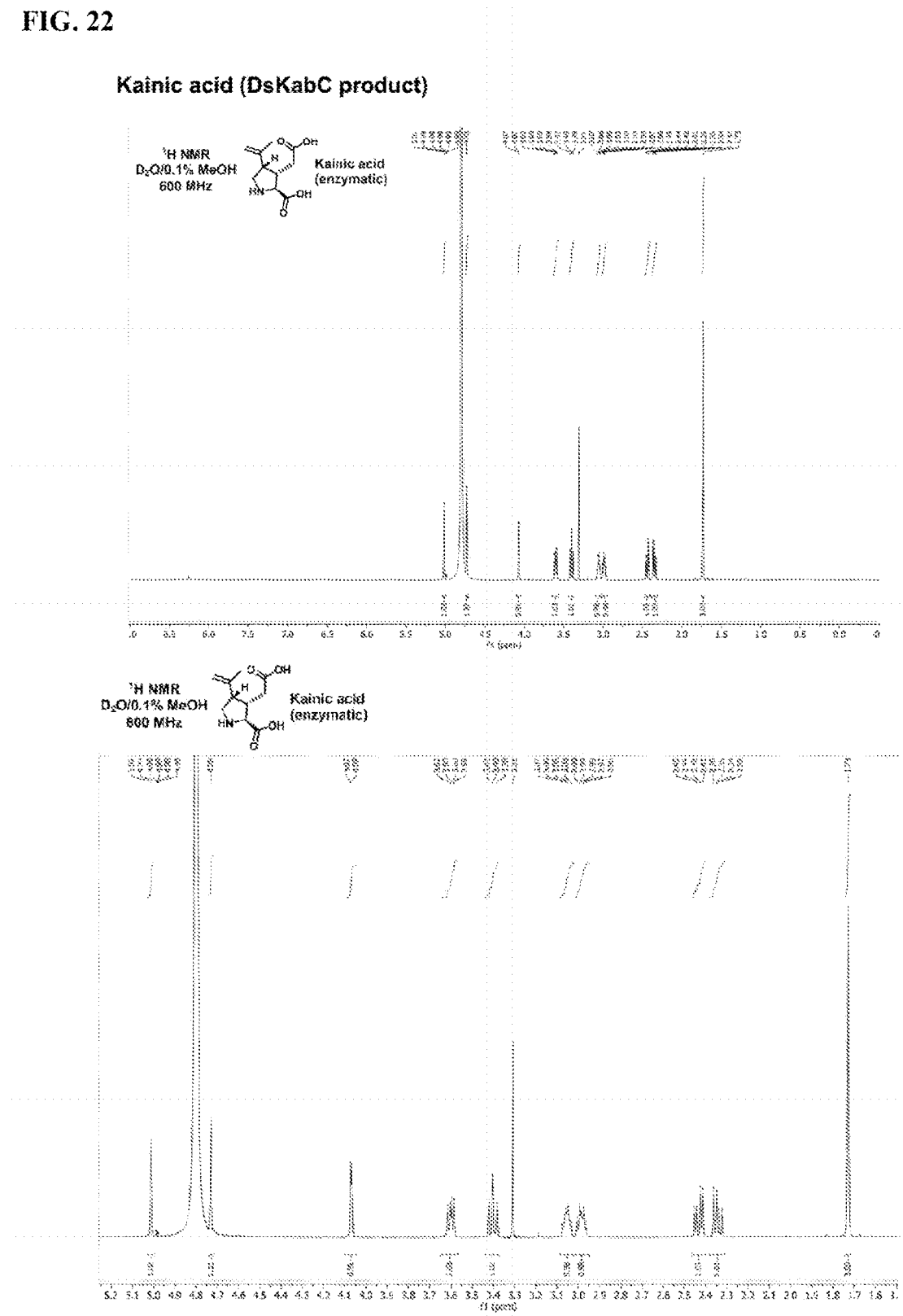
FIG. 22 shows $^1$H NMR analysis of kainic acid (DsKabC or enzymatic product).
Figure 23:
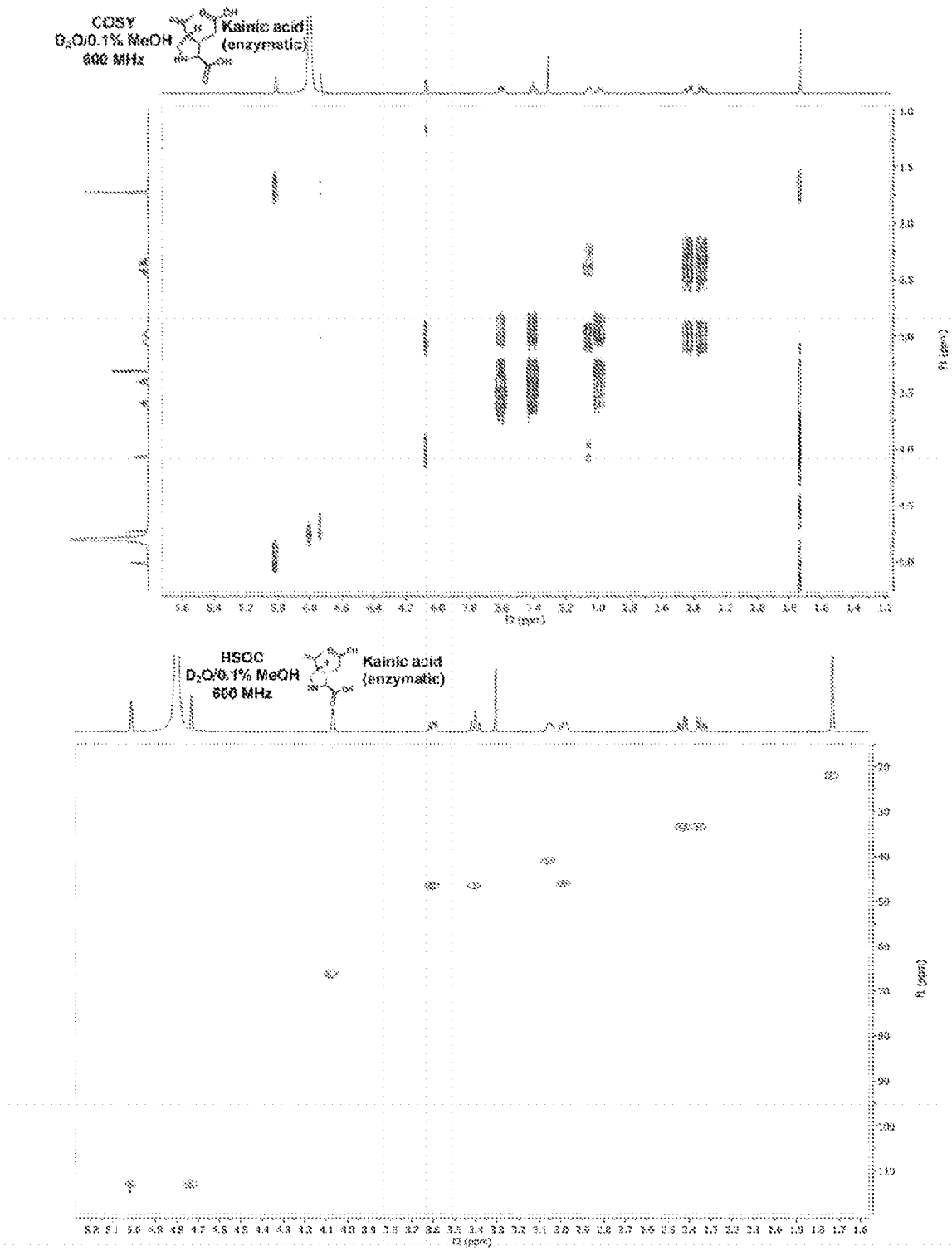
FIG. 23 shows COSY and HSQC analysis of kainic acid (DsKabC enzymatic product).
Figure 24:
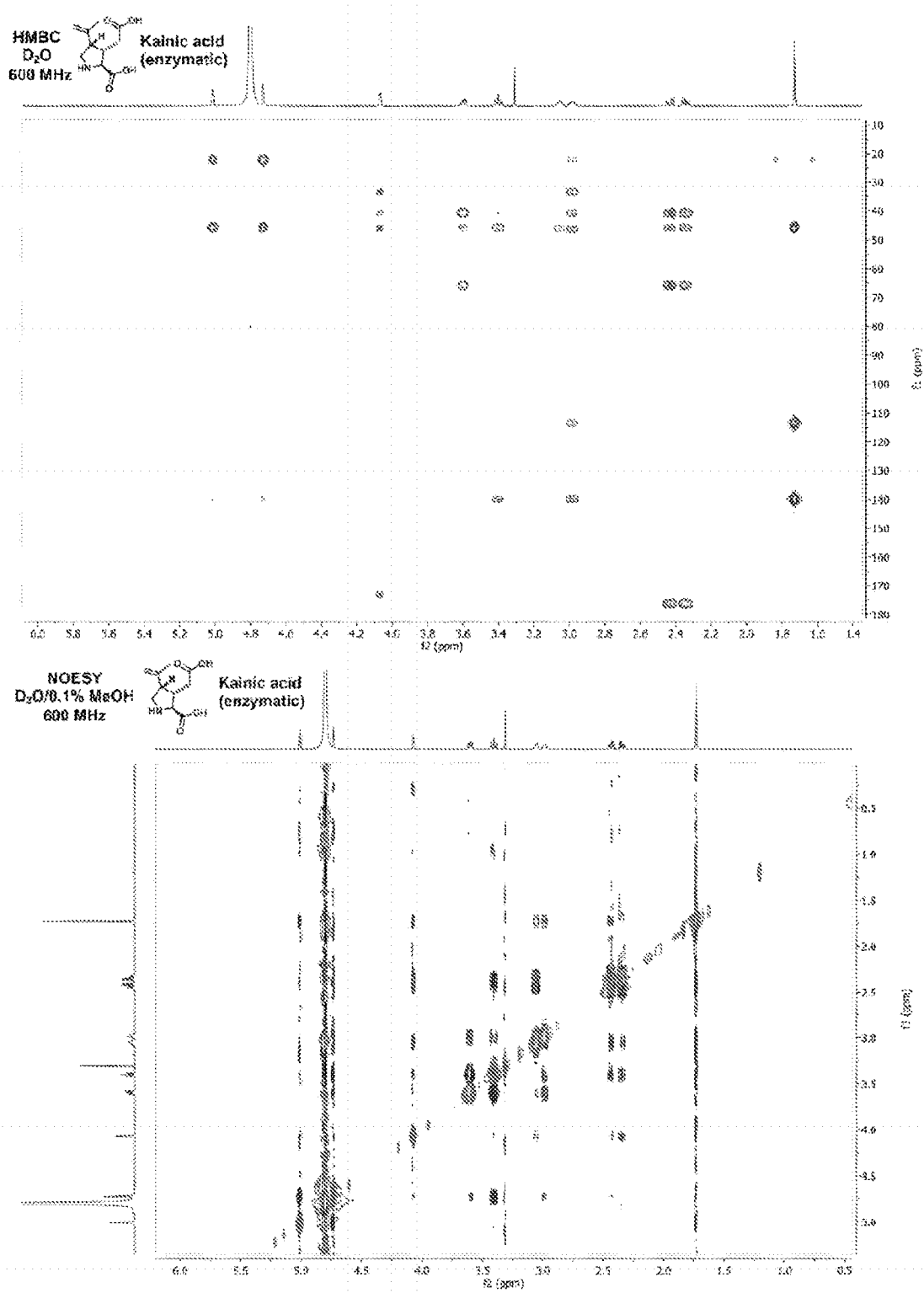
FIG. 24 shows HMBC and NOESY analysis of prekainic acid (DsKabC or enzymatic product).
Figure 25:
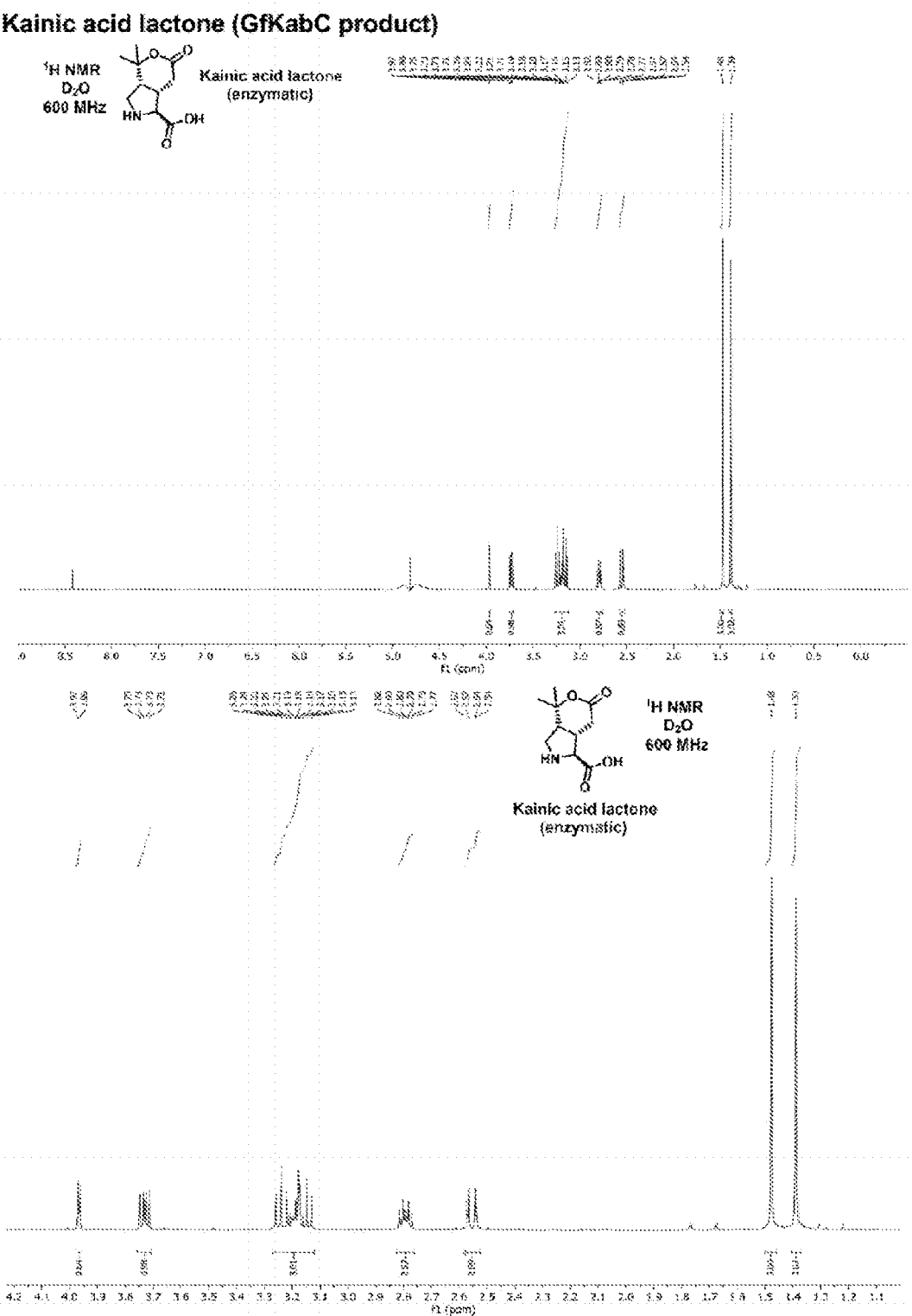
FIG. 25 shows $^1$H NMR analysis of kainic acid lactone (GfKabC enzymatic product).
Figure 26:
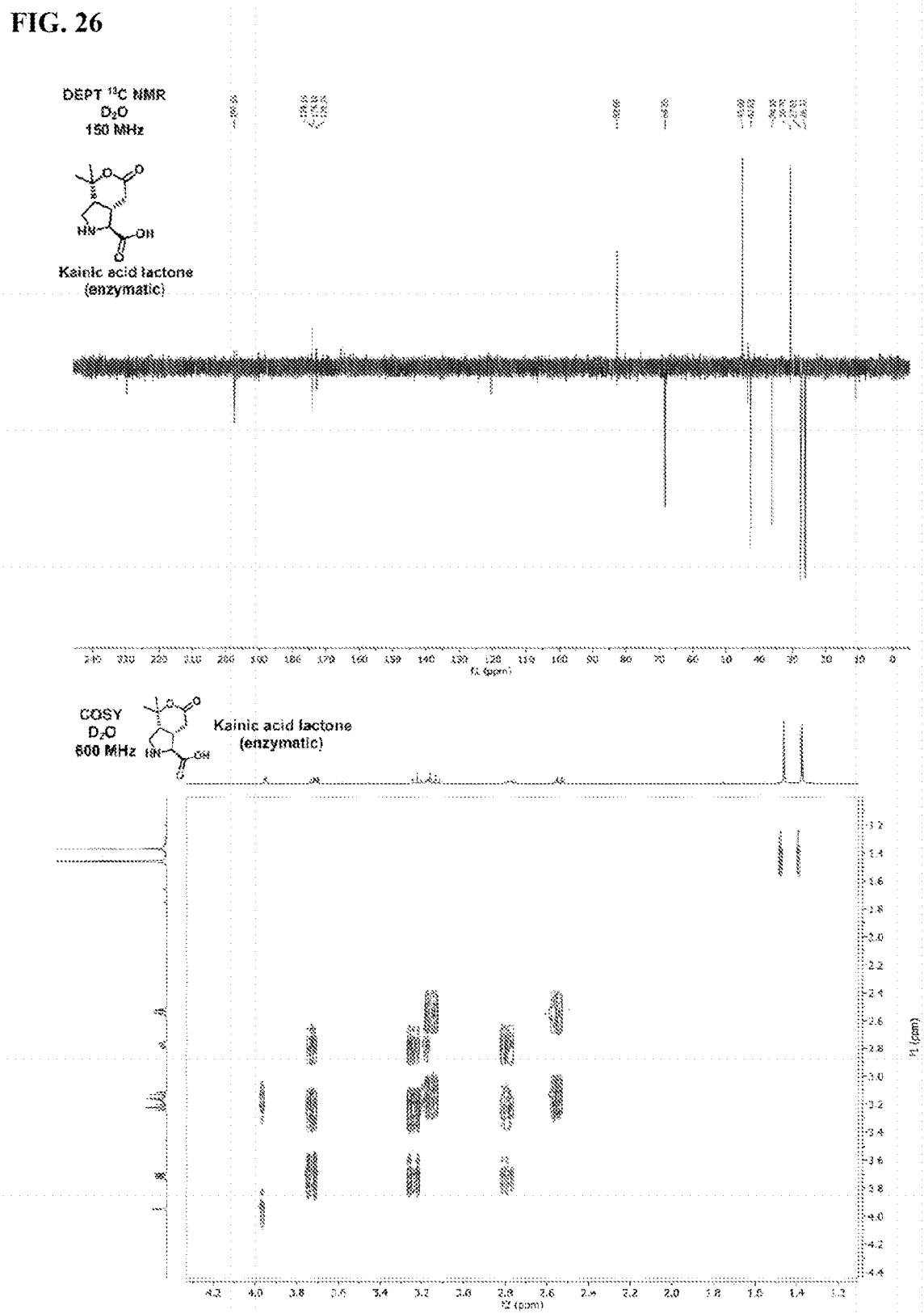
FIG. 26 shows DEPT $^{13}$C NMR and COSY analysis of kainic acid lactone (enzymatic product).
Figure 27:
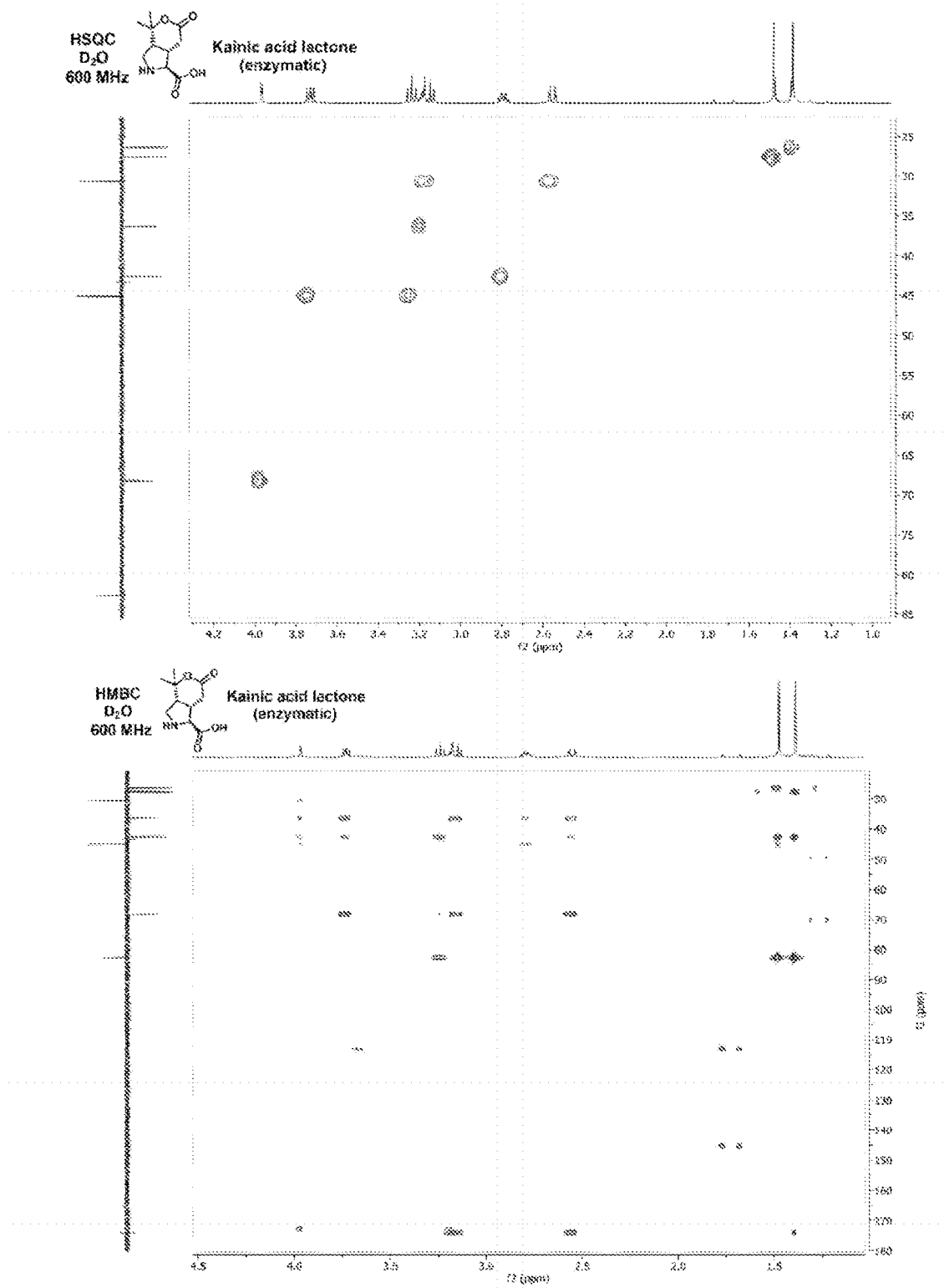
FIG. 27 shows HSQC and HMBC analysis of kainic acid lactone (enzymatic product).
Figure 28:
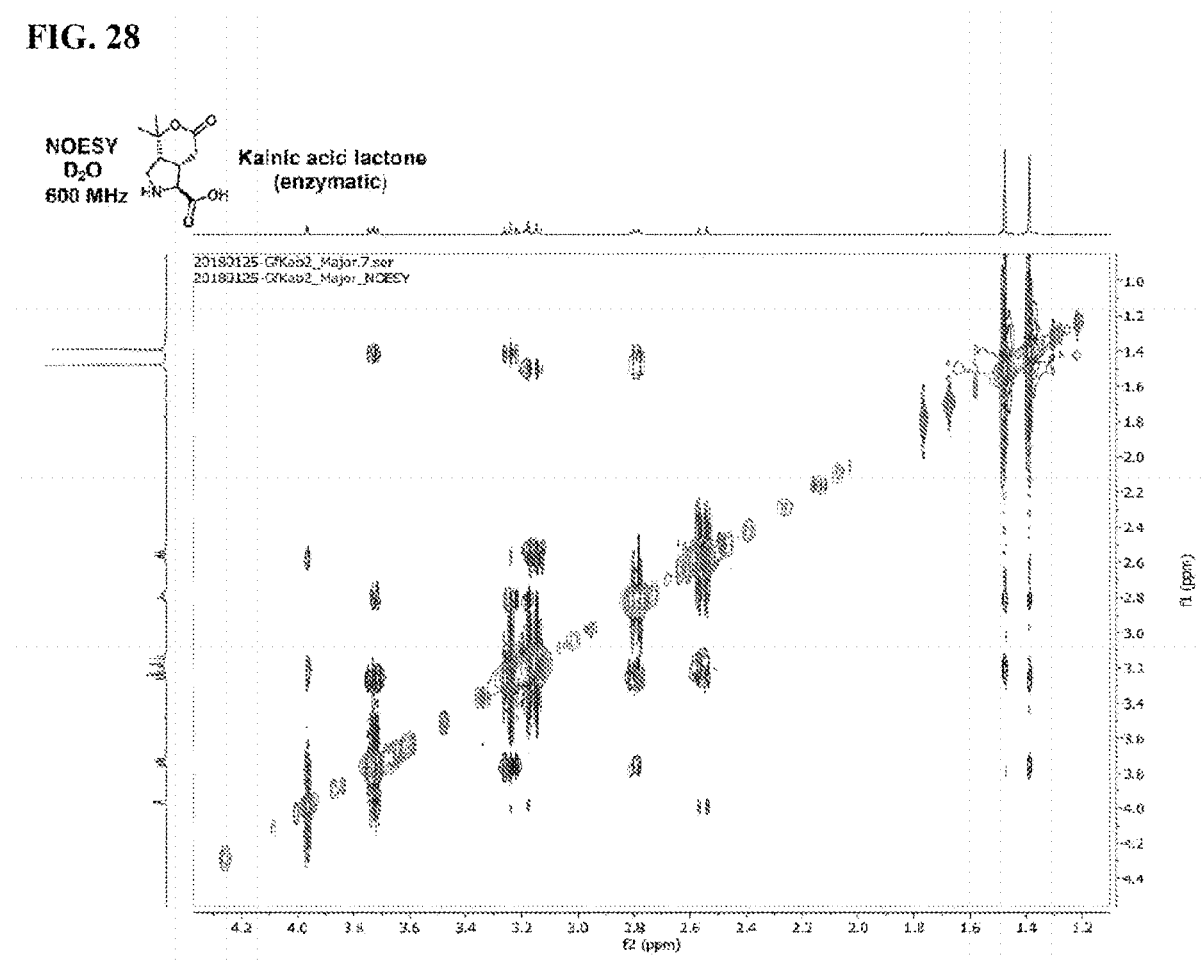
FIG. 28 shows NOESY analysis of kainic acid lactone (enzymatic product).

MBP-GfKabC was buffer exchanged into 300 mM KCl, 50 mM HEPES pH 8.0 to remove glycerol. Six 1 mL reactions of GfKabC were set up as follows: 8 mM αKG, 5 mM prekainic acid, 1 mM L ascorbic acid, 50 μM ferrous sulfate, 50 μM MBP-GfKabC in buffer containing 300 mM KCl, 50 mM HEPES pH 8.0. The reaction was incubated at 22° C. for 30 hours and the protein was removed with 30 kDa Amicon Ultra Centrifugal Filter. The protein was washed with distilled water and the flow throughs were collected and lyophilized. The dried material was resuspended in 500 μL of 0.1% aqueous formic acid and purified by semipreparative HPLC (Agilent 1200 Infinity HPLC) using a Synergi Polar-RP 4μ 250×10.0 mm column with the following method: 0% B (18 min, 2 mL/min), 0 to 95% B (2 min, 3 mL/min), 95% B (3 min, 3 mL/min), 95 to 0% B (4 min, 3 mL/min), 0% B (3 min, 3 mL/min), wherein A=0.1% aqueous formic acid, and B=0.1% formic acid in acetonitrile. The major peak (~9.5 min retention time) was collected and lyophilized to afford kainic acid lactone (3.3 mg, 26% isolated yield) as a white powder. $^1$H NMR (600 MHz, $D_2O$) δ 3.97 (d, J=3.9 Hz, 1H), 3.73 (dd, J=12.2, 8.2 Hz, 1H), 3.24 (dd, J=11.9, 11.9 Hz, 1H), 3.22-3.16 (m, 1H), 3.15 (dd, J=18.0, 9.8 Hz, 1H), 2.79 (ddd, J=11.5, 8.1, 8.1 Hz, 1H), 2.55 (dd, J=17.5, 3.9 Hz, 1H), 1.48 (s, 3H), 1.39 (s, 3H). $^{13}$C NMR (151 MHz, $D_2O$): δ 174.3, 172.9, 82.8, 68.3, 45.3, 42.8, 36.5, 30.9, 27.9, 26.6; HRMS (ESI) calculated for $C_{10}H_{14}NO_4^-$ 212.0928, found 212.0930 (M-H)$^-$ Kainic Acid Biotransformation and Purification E. coli BL-21 transformed with the pET28 DsKabC vector were grown overnight in 20 mL of lysogeny broth. The culture was pelleted to remove the media and added to 1 L of M9 minimal media supplemented with 100 μM $CaCl2$) in a 2.8 L baffled flask. The flasks were placed in a shaking incubator (200 rpm, 37° C.) and the cells were grown to an $OD_{600}$ of ~1.3. The flasks were cooled at 18° C. for 45 minutes followed by the addition of 0.5 mM IPTG. Fifteen minutes after IPTG was added, 4 g of glucose and the crude prekainic acid synthetic reaction product was added with continuous shaking incubation at 18° C. Additional glucose (4 g) was added after 16 h. Time points were taken and analyzed for the presence of kainic acid using the LCMS methodology described in the kainic acid fermentation protocol. After 40 h, the cultures were centrifuged to remove cells and the media was collected. Thirty grams of activated carbon (Darco G-60) per 1 L of media was washed with distilled water and added to the cell free media. The activated carbon was stirred with the media for 30 min before filtering to remove the spent media. The activated carbon was washed with distilled water twice and then rapidly stirred in 300 mL of 80% acetic acid for 15 min to elute the kainic acid. Three additional 300 mL 80% acetic acid elutions were used to maximize kainic acid recovery. The eluent was dried by rotary evaporation to afford a reddish oil which was further purified by preparative RP-HPLC (Agilent PrepStar and ProStar 410 HPLC) using a Phenomenex Luna 5μ C18(2), 100×21.2 mm column at a flow rate of 10 mL/min with the following method: 2% B (5 min), 2 to 20% B (10 min), 20 to 95% B (1 min), 95% B (4 min), 95 to 2% B (2 min), 2% B (3 min), wherein A=0.1% aqueous formic acid, and B=0.1% formic acid in acetonitrile. Absorbance at 210 nm was monitored and the major peak was collected. The kainic acid containing fractions were combined and the volume was reduced in vacuo before lyophilization. Using this method, 6 L of culture were used to afford 1.07 g of kainic acid (32% overall isolated yield) as a white powder. NMR (FIG. 13) indicates >95% purity with the major contaminants consistent with acetic acid (~2%) and formic acid (~2%).

Synthetic Methods

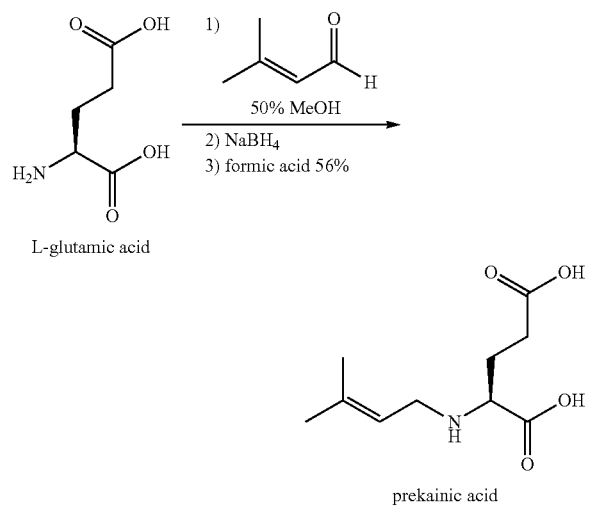

L-glutamic acid prekainic acid

Prekainic Acid Chemical Synthesis

This molecule was synthesized using a modified published procedure [10]. An aqueous solution of L-glutamic acid (0.147 g, 1 mmol) and crushed NaOH (0.083 g, 2.1 mmol) in 2.5 mL of $H_2O$ was stirred at RT. MeOH (2.5 mL) was added. 3-methyl-2-butenal (0.135 mL, 1.4 mmol) was added and the reaction was immediately cooled in an ice bath while stirring. $NaBH_4$ (0.048 g, 1.3 mmol) was added and stirred for 20 minutes. The reaction was brought to room temperature over 20 minutes and was then acidified to ~pH 4.0 with formic acid. The methanol was removed in vacuo and the reaction was purified by injection onto preparative RP-HPLC (Agilent 1260 Infinity HPLC) using a Phenomenex Luna 5μ C18(2), 100×21.2 mm column at a flow rate of 10 mL/min with the following method: 2% B (5 min), 2 to 20% B (10 min), 20 to 95% B (1 min), 95% B (4 min), 95 to 2% B (2 min), 2% B (3 min), wherein A=0.1% aqueous formic acid, and B=0.1% formic acid in acetonitrile. Absorbance at 210 nm was monitored and the major peak was collected. Acetonitrile was removed by rotary evaporation before lyophilization to afford prekainic acid (147 mg, 56% isolated yield) as a white powder. $^1$H NMR (599 MHz, $D_2O$) δ 5.22 (t, J=7.8 Hz, 1H), 3.64 (t, J=7.9, 6.4 Hz, 2H), 3.61 (dd, J=7.7, 5.5 Hz, 1H), 2.56-2.42 (m, 2H), 2.13 (ddt, J=13.8, 7.0, 7.0 Hz, 1H), 2.03 (dtd, J=14.4, 7.3, 6.7 Hz, 1H), 1.76 (s, 3H), 1.68 (s, 3H). $^{13}$C NMR (151 MHz, $D_2O$): δ 177.5, 173.8, 145.3, 113.2, 60.4, 44.5, 30.1, 25.5, 25.4, 17.9; HRMS (ESI) calculated for $C_{10}H_{16}NO_4^-$ 214.1085, found 214.1088 (M-H)$^-$. between ppkabA and ppkabC and with different gene ori Prekainic Acid Chemical Synthesis for Biotransformation An aqueous solution of L-glutamic acid (1.18 g, 8.0 mmol) and crushed NaOH (0.672 g, 16.8 mmol) in 20 mL of $H_2O$ was stirred at room temperature. MeOH (20 mL) was slowly added. 3-methyl-2-butenal (1.08 mL, 11.2 mmol) was added and the reaction was immediately cooled in an ice bath while stirring. $NaBH_4$ (0.393 g, 10.4 mmol) was added and stirred for 20 minutes. The reaction was brought to room temperature over 20 minutes and was then acidified with formic acid to ~pH 4.0. The methanol was removed in vacuo. The crude reaction product was neutralized with NaOH to ~pH 8.0 and ⅓ of the reaction was added to a 1 L biotransformation.

DMAPP Chemical Synthesis

This synthesis was adapted from a literature procedure [11]. To a solution of tris (tetrabutylammonium) hydrogen pyrophosphate trihydrate [11] (3.00 g, 3.32 mmol) in dry acetonitrile (15 mL) at −35° C. was added prenyl bromide (0.19 mL, 0.25 g, 1.66 mmol) over 2 minutes. The reaction mixture was stirred at −35° C. for 10 minutes, then warmed to room temperature and stirred for an additional 2 hours. The solvent was removed in vacuo and the crude residue was resuspended in minimal ion exchange buffer (25 mM aqueous $NH_4HCO_3$, 2% isopropanol) and passed through a column of DOWEX AG50W-X8 ($NH_4^+$form, 40 mL (~70 milliequivalents)). The first two column volumes (80 mL) were collected and lyophilized to generate an off-white solid. This crude mixture was further purified via resuspension in 50 mM aqueous $NH_4HCO_3$ (2 mL), addition of 1:1 acetonitrile:isopropanol (8 mL) with thorough mixing, centrifugation (2000×g, 5 minutes) and pipetting the resultant supernatant into a new flask, repeating this procedure 5 times in total. The pooled supernatants were concentrated in vacuo then further purified by cellulose chromatography prepared in an analogous way to that previously described [11]. Purified DMAPP was eluted using a gradient of (1:2:1) to (2:2:1) water:acetonitrile:isopropanol (50 mM $NH_4HCO_3$). Pooled fractions were concentrated in vacuo and lyophilized, generating trisammonium DMAPP (0.452 g, 91%) as a white powder. $^1$H NMR (500 MHz, D20) δ 5.31 (t, J=7.2 Hz, 1H), 4.31 (dd, J=7.0, 6.8 Hz, 2H), 1.62 (s, 3H), 1.58 (s, 3H); LRMS (ESI) calculated for $C_5H_{11}O_7P_2^-$ 245.00, found 245.02 (M-H)$^-$.

REFERENCES OF EXAMPLE 2

1. T. P. Michael, F. Jupe, F. Bemm, S. T. Motley, J. P. Sandoval, C. Lanz, O. Loudet, D. Weigel, J. R. Ecker, Nat. Commun. 2018, 9, 541.
2. H. Li, Bioinformatics 2018, 34, 3094-100.
3. H. Li, Bioinformatics 2016, 32, 2103-10.
4. R. R. Wick, M. B. Schultz, J. Zobel, K. E. Holt, Bioinformatics 2015, 31, 3350-2.
5. R. Vaser, I. Sovid, N. Nagarajan, M. Sikid, Genome Res. 2017, 27, 737-46.
6. B. J. Walker, T. Abeel, T. Shea, M. Priest, A. Abouelliel, S. Sakthikumar, C. A. Cuomo, Q. Zeng, J. Wortman, S. K. Young, et al., PLoS One 2014, 9, e112963.
7. K. Katoh, J. Rozewicki, K. D. Yamada, Brief Bioinform. 2017, 1-7.
8. W. P. Maddison, D. R. Maddison, "Mesquite: a modular system for evolutionary analysis," 2018.
9. D. Silvestro, I. Michalak, Org. Divers. Evol. 2012, 12, 335-7.

10. J. K. Brunson, S. M. K. McKinnie, J. R. Chekan, J. P. McCrow, Z. D. Miles, E. M. Bertrand, V. A. Bielinski, H. Luhavaya, M. Obornik, G. J. Smith, et al., *Science* 2018, 361, 1356-8.
11. A. B. Woodside, Z. Huang, C. D. Poulter, *Org. Synth.* 1988, 66, 211-6.
12. G. W. Saunders, C. Jackson, E. D. Salomaki, *Mol. Phylogenet. Evol.* 2018, 119, 151-9.
13. N. Matasci, L. Hung, Z. Yan, E. J. Carpenter, N. J. Wickett, S. Mirarab, N. Nguyen, T. Warnow, S. Ayyampalayam, M. Barker, et al., *Gigascience* 2014, 3, 17.
14. J. Janouskovec, A. Horik, M. Obornik, J. Lukes, P. J. Keeling, *Proc. Natl. Acad. Sci. U.S.A.* 2010, 107, 10949-54.
15. C. Bowler, A. E. Allen, J. H. Badger, J. Grimwood, K. Jabbari, A. Kuo, U. maheswari, C. Martens, F. Maumus, R. P. Otillar, et al., *Nature* 2008, 456, 239-44.
16. N. P. Dunham, W.-C. Chang, A. J. Mitchell, R. J. Martinie, B. Zhang, J. A. Bergman, L. J. Rajakovich, B. Wang, A. Silakov, C. Krebs, et al., *J. Am. Chem. Soc.* 2018, 140, 7116-26.
17. R. Calaf, A. Barlatier, D. Gargon, G. Balansard, M. Pellegrini, J. Reynaud, *J Appl. Phycol.* 1989, 1, 257-66.
18. O. Goldberg, A. Luini, V. I. Teichberg, *J. Med. Chem.* 1983, 26, 39-42.

Example 3

Kainic Acid Biotransformation and Purification

First, *E. coli* BL-21 cells previously transformed with the pET28 DsKabC vector were inoculated into 20 mL of lysogeny broth supplemented with 50 mg/L kanamycin and grow overnight into a shaking incubator at 37° C. The *E. coli* culture was then pelleted to remove the media and add to 1 L of M9 minimal media (see M9 minimal media recipe). Following addition of the M9 minimal media, the flask was placed in a shaking incubator (200 rpm, 37° C.) and the cells grown to an $OD_{600}$ of ~1.3. (about 7 hours). Once the OD was reached, the flasks were cooled at 18° C. for 45 minutes and IPTG (isopropyl β-D-1-hiogalactopyranoside) was added to a final concentration of 0.5 mM. After 15 minutes, 4 g of filter sterilized glucose and ⅓ of the crude prekainic acid synthetic reaction product were added (see synthetic method), and incubation continued at 18° C. with shaking. Additional 4 g of filter sterilized glucose were added after 16 h of incubation. After 40 h of incubation, the culture was centrifuged to remove cells and to collect the media. Cells were bleached and properly disposed of. Then, 40 g of activated carbon were washed (Darco G-60) per 1 L of media with distilled water and filter dry using Buchner funnel, filter paper, and a vacuum flask. The washed activated carbon was added to the media and the solution was then stirred for 30 min. Filtering was then realized using the Buchner funnel setup to remove the spent media, and the activated carbon was washed with distilled water twice. The activated carbon was stirred in 300 mL of 80% acetic acid for 15 min to elute the kainic acid and collection was realized by filtration. An additional 300 mL 80% acetic acid elution could be used to maximize kainic acid recovery. The eluent was loaded onto 20 g of Dowex 50wx8 resin ($H^+$ form), and the resin washed with water subsequently. The kainic acid was eluted with 2 M ammonium hydroxide in 50% methanol and 50% water solution. The kainic acid containing fractions was combined and the volume reduced by rotary evaporation. Freezing and lyophilization steps were used to afford a light orange powder. The powder was then dissolved in a minimal volume of hot 1:1 ethanol to water solution (approximately 16 mL per 1 g of crude powder), and the solution acidified with formic acid to a final concentration of 1% v/v. Crystallization was initiated and then allowed to continue by leaving the solution at room temperature, then 4° C. and finally −20° C. The resulting crystals were collected and then washed with cold isopropanol. A recrystallization step could be performed to improve purity.

M9 Minimal Media

To prepare the M9 minimal media, the solution in the table below was prepared the night before inoculation, in a 2.8 L baffled flask.

| Component | Formula | Amount |
|---|---|---|
| Sodium phosphate dibasic heptahydrate | $Na_2HPO_4 \cdot 7H_2O$ | 11.2 grams |
| Potassium phosphate monobasic | $KH_2PO_4$ | 3 grams |
| Ammonium chloride | $NH_4Cl$ | 1 gram |
| Sodium chloride | NaCl | 0.5 grams |
| Milli-Q water | | 1 L |

On the day of inoculation, the stock solutions shown in the table below were added the autoclaved solution contained in the 2.8 L baffled flask.

| Solution | Amount | Notes |
|---|---|---|
| 25% glucose | 16 mL | Filter sterilized and stock kept at 4° C. or −20° C. |
| 1M $MgSO_4$ | 1 mL | Filter sterilized and can stock kept at room temp |
| 77 mg/mL $FeSO_4 \cdot 7H_2O$ | 0.1 mL | Prepared fresh |
| 0.5% thiamine | 0.1 mL | Filter sterilized and stock could be freezed |
| 100 mM $CaCl_2$ | 1 mL | Filter sterilized and can stock kept at room temp |
| 50 mg/mL Kanamycin | 1 mL | Filter sterilized and stock could be freezed |

Prekainic Acid Chemical Synthesis for Biotransformation

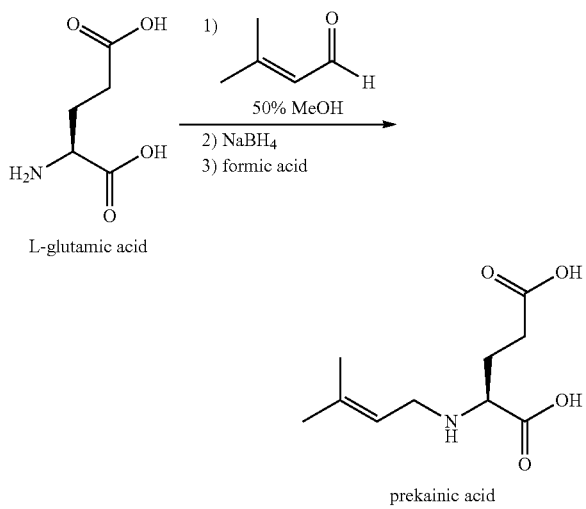

L-glutamic acid (1.18 g, 8.0 mmol) and crushed NaOH (0.672 g, 16.8 mmol) were added to 20 mL of $H_2O$ and stirred at room temperature, to which 20 mL of methanol were slowly added. Then, 3-methyl-2-butenal (1.08 mL, 11.2 mmol) was added and the reaction was immediately cooled in an ice bath while stirring. After the 3-methyl-2-butenal step, argon was added to the headspace of the bottle to prevent oxidation overtime. Sodium borohydride (0.393 g, 10.4 mmol) was added and stirred for 20 minutes. The reaction was then removed from the ice water bath and stirring continued at room temperature for 20 minutes. The reaction was quenched by adding formic acid dropwise until bubbling stopped and the pH reached ~4.0. Methanol was removed by rotary evaporation, and the concentrate neutralized to ~ pH 8.0 with NaOH. Finally, ⅓ of this reaction was added to 1 L of the biotransformation.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

Exemplary Sequences:

```
SEQ ID NOs: 1-5, respectively:
DsKabC (Digenea simplex):
MTVSKYNGVASTFNGVARRFDFAPLEADKLNWYPRSALPPEIPAIDLNKVNTEEELAQF

LVDIRKSGLFYIVDHGIPEEISIGCYNAFREFCNLPEEAREKYNTDESFKSGGYVPFKGTSI

GGGNLFERQKDFVVKFFWRGPSVVNRSPNDRFAEFHDEHHRKTAELAEKIITTILKALK

TRFPEFHPDELKDNINVRNMFFSNRIYPEAPPDDGEKADYRLVPHRDLSFITLANQVPAN

NGFKGLFILTGDGEKIPVPPIRNSYLVFIGQGLSYLTNKYLPAALHGVDFPDNTNFEGSER

ASLISFYEPNDYMMPSKNINPLPEEIFEKSCTFYDDVGVGRAGTTYNYVRYKFHEGYYL

PpKabC (Palmaria palmata):
MPVYNGTSQAFNFAPLHPDSLNWCPKSSLPPEIPVVDLSKLNSEAELAQFLVDIRKSGLF

YVVNHGVPEELSIGCYNRFRQFCNIPEDQRAEYSTDHHFVNGGYMPYKSSSIGKANKGK

SQKDFVVKYFWRGPRVENRSPDADFKSYHDEYHRRTADIANSVITKILQALTTRFPDFD

PAEYKDNINSHHMFFSNRLYPDNEPEKGENVEYRLVPHRDLSFVTLAHQIPADNGYQGL

FVFTGDGKKVCVPPIRNSYLVFMGQAMSYLTNKYLPAGLHGVDFPEKNCFEGSERSSLI

SFYEPHDHMMPSKALTPKDDEIFDRGCSFFDDIGVDKTGTTYMYVKNKFHEGYYL

PhKabC (Palmaria hecatensis):
MPVYNGTPQAYNGTSQAFNFAPLDADSLTWCPESSLPPEIPAIDLSKVNSKSELAEFLVNI

RKSGLFYVVNHGVPEELSMGCYNHFREFCNIPEEERAEYSTDHHFVHGGYMPYKSSSIG

KANKGKDQKDFVVKYFWRGPLVENRSPSTGFKRYHDEYHRRTSDIANSVIAKIMQALT

TRFPDFDPDEYKKNINSHHMFFSNRLYPDNEPEKGENAEYRLVPHRDLSFVTLAHQIPAD

NGYQGLFVLTGDGKKVCVPPIRNSYLVFMGQAMSYLTNKYLPAGLHGVDFPEKNCFEG

SERSSLISFYEPHDHMMPSKALTPKDDEIFDRGCSFFDDIGVDKSGTAYMHVKNKFHEG

YYL

ReKabC (Rhodophysema elegans):
MAVYNGVSQAFDFAPLDADSLNWCPQSSLPPEIPAIDLGKVNTRAELAQFLIDIRRSGLF

YVVNHGVPEELSIGCYNLFRRFCNIPEEERAKYSTDHHFVNGGYMPYKSSSIGKANMGK
```

-continued

DQKDFVVKYFWRGPRVENRTPTAEFKKYHDEYHRRTSGVADTVIEKIMQALATRFPDF

DPDEYKENTNSHHMFFSNRLYPENEPEKGENVEYRLVPHRDLSLVTLAHQIPADNGYQ

GLFVLTGDGKKVPVPPIRNSYLVFLGQALSYLTNKYLPAGLHGVDFPEKNSFEGSERSSL

ISFYEPHDRMMPSKALTPKEDEVFDRSCSFFDDIGVDTSGTTYMYVKNKFHEGYYL

GfKabC (Grateloupia filicina):
MTSFDFVAKTFDFAPVKADELKWYPRSALPPEIPVIDLNNVNTEEELAQFLVDIRKSGLF

YVVNHDIPEEISIQTYNEFREFCKLPEEARQKYNTDRCFFNGGYVPFKATSINGGNKNKQ

QRDFVVKFFWRGPHVVNRSPNERFAKWHHQYHTRTAELGEKVMTTIAKALKTRFPDF

DPAELEDNVNPHNMIFSNRIYPEFPPSEGEDAEYRLTPHRDISYITLVNQTPANNGFKALF

IVTGDGER VYVPPIRNSYLVFIGQSLSYLTNKYLPAALHGVAFPDGNLEGCERASLVSFY

EPYDRMVPSKNIKPTAEEIAPKSCSFYDSIGCDKTGTTFTDVRAKFHSGYYV

SEQ ID NOs: 6-10, respectively:
>KabC (Digenea simplex)
ATGACAGTAAGTAAGTACAACGGTGTTGCGAGTACGTTCAACGGTGTTGCAAGGAG

ATTCGACTTTGCCCCATTGGAGGCAGATAAATTGAATTGGTATCCCAGGTCAGCTCT

TCCTCCAGAAATCCCTGCTATCGACCTGAATAAGGTCAATACTGAAGAAGAACTGGC

TCAATTCCTGGTCGATATTCGCAAATCTGGGCTCTTTTATATTGTTGATCATGGCATT

CCAGAGGAGATCTCTATAGGATGTTACAATGCATTCCGTGAGTTTTGCAACCTTCCC

GAGGAAGCAAGAGAGAAGTACAACACAGATGAGTCCTTTAAAAGCGGTGGCTATGT

TCCTTTCAAAGGCACGTCGATTGGTGGAGGGAACTTGTTTGAACGACAGAAGGATTT

CGTTGTCAAATTCTTTTGGAGAGGACCAAGTGTTGTCAATAGGTCTCCTAATGATCG

CTTTGCCGAATTCCATGATGAACATCATCGAAAGACAGCTGAGTTGGCCGAAAAAA

TCATCACTACCATTTTGAAAGCCCTGAAGACACGCTTTCCAGAATTCCATCCTGACG

AGCTAAAGGATAATATCAATGTTCGAAACATGTTTTTCAGTAATCGAATCTATCCAG

AGGCTCCGCCAGATGATGGAGAAAAAGCTGACTACCGACTTGTTCCTCATCGAGATC

TCAGTTTTATCACTCTTGCAAATCAAGTTCCGGCTAACAATGGATTCAAGGGTCTTTT

TATACTGACAGGTGATGGAGAAAAAATTCCTGTTCCTCCAATCCGGAACAGCTACTT

GGTCTTCATCGGTCAAGGCCTCTCATATCTCACGAATAAGTATCTTCCTGCAGCGCTT

CATGGTGTGGACTTTCCAGACAATACAAATTTTGAAGGAAGTGAAAGAGCCTCTCTG

ATCAGCTTCTACGAGCCAAACGATTACATGATGCCATCCAAGAACATTAACCCTTTA

CCTGAGGAGATATTTGAGAAAAGCTGTACGTTTTACGATGATGTCGGAGTAGGGAG

GGCTGGTACAACATATAATTACGTGAGGTACAAATTTCATGAAGGATACTACCTTTA
A

>KabC (Rhodophysema elegans)
ATGGCGGTGTACAATGGCGTCTCGCAGGCCTTCGACTTCGCGCCGCTCGACGCCGAC

AGCCTCAACTGGTGCCCCCAGTCGTCCCTGCCGCCCGAGATCCCCGCCATCGACCTC

GGCAAAGTGAACACCAGGGCCGAGCTCGCCCAGTTCCTGATCGACATCCGCAGGTC

CGGCCTCTTCTACGTCGTCAACCACGGCGTGCCGGAAGAGCTCTCGATCGGCTGCTA

CAACCTCTTTCGCCGCTTCTGCAACATCCCCGAGGAGGAGCGCGCCAAGTACAGCAC

CGACCATCATTTCGTCAACGGCGGCTACATGCCATACAAGAGCTCCTCCATCGGCAA

GGCGAACATGGGCAAGGACCAGAAGGACTTTGTCGTCAAGTACTTCTGGAGGGGGC

CCCGCGTGGAGAACAGGACGCCCACCGCCGAGTTTAAGAAGTATCACGATGAGTAC

CATCGCAGGACTTCGGGCGTCGCAGACACGGTCATAGAGAAGATTATGCAGGCGCT

```
GGCGACGCGCTTTCCGGACTTCGACCCCGACGAGTACAAGGAGAACACGAACAGCC

ATCACATGTTTTTCAGCAACAGGCTCTACCCCGAAAACGAGCCGGAGAAGGGGGAG

AACGTCGAGTACCGCCTTGTTCCGCATCGCGACCTCAGTTTGGTGACGCTCGCGCAC

CAGATCCCCGCAGACAATGGCTACCAGGGCCTGTTCGTTCTTACCGGCGACGGGAA

GAAGGTGCCTGTGCCGCCTATCCGCAACAGCTATCTCGTCTTCCTGGGGCAGGCGTT

GTCTTATCTCACCAACAAGTATCTGCCTGCTGGATTGCATGGCGTGGACTTTCCGGA

GAAGAACTCCTTTGAGGGGAGCGAGCGGTCGTCACTTATTTCATTCTACGAGCCGCA

CGACCGCATGATGCCGTCGAAGGCGCTCACGCCAAAAGAGGATGAAGTTTTTGATA

GAAGCTGCTCCTTTTTCGATGATATTGGTGTTGATACGAGTGGCACGACGTATATGT

ACGTGAAAAATAAGTTCCACGAGGGCTATTATCTATAG

>KabC (Palmaria hecatensis)
ATGGCGGTGTACAATGGCGTCTCGCAGGCCTTCGACTTCGCGCCGCTCGACGCCGAC

AGCCTCAACTGGTGCCCCCAGTCGTCCCTGCCGCCCGAGATCCCCGCCATCGACCTC

GGCAAAGTGAACACCAGGGCCGAGCTCGCCCAGTTCCTGATCGACATCCGCAGGTC

CGGCCTCTTCTACGTCGTCAACCACGGCGTGCCGGAAGAGCTCTCGATCGGCTGCTA

CAACCTCTTTCGCCGCTTCTGCAACATCCCCGAGGAGGAGCGCGCCAAGTACAGCAC

CGACCATCATTTCGTCAACGGCGGCTACATGCCATACAAGAGCTCCTCCATCGGCAA

GGCGAACATGGGCAAGGACCAGAAGGACTTTGTCGTCAAGTACTTCTGGAGGGGGC

CCCGCGTGGAGAACAGGACGCCCACCGCCGAGTTTAAGAAGTATCACGATGAGTAC

CATCGCAGGACTTCGGGCGTCGCAGACACGGTCATAGAGAAGATTATGCAGGCGCT

GGCGACGCGCTTTCCGGACTTCGACCCCGACGAGTACAAGGAGAACACGAACAGCC

ATCACATGTTTTTCAGCAACAGGCTCTACCCCGAAAACGAGCCGGAGAAGGGGGAG

AACGTCGAGTACCGCCTTGTTCCGCATCGCGACCTCAGTTTGGTGACGCTCGCGCAC

CAGATCCCCGCAGACAATGGCTACCAGGGCCTGTTCGTTCTTACCGGCGACGGGAA

GAAGGTGCCTGTGCCGCCTATCCGCAACAGCTATCTCGTCTTCCTGGGGCAGGCGTT

GTCTTATCTCACCAACAAGTATCTGCCTGCTGGATTGCATGGCGTGGACTTTCCGGA

GAAGAACTCCTTTGAGGGGAGCGAGCGGTCGTCACTTATTTCATTCTACGAGCCGCA

CGACCGCATGATGCCGTCGAAGGCGCTCACGCCAAAAGAGGATGAAGTTTTTGATA

GAAGCTGCTCCTTTTTCGATGATATTGGTGTTGATACGAGTGGCACGACGTATATGT

ACGTGAAAAATAAGTTCCACGAGGGCTATTATCTATAG

>KabC (Palmaria palmata)
ATGCCCGTGTACAACGGCACCTCCCAGGCCTTCAACTTCGCGCCCCTCCACCCCGAC

AGCCTCAACTGGTGCCCCAAGTCGTCCCTGCCCCCCGAGATCCCCGTAGTCGACCTT

AGCAAACTCAACTCTGAGGCCGAGCTCGCCCAGTTTCTGGTCGACATCCGCAAGTCC

GGCCTCTTCTACGTTGTCAACCACGGCGTGCCGGAGGAGCTCTCCATCGGCTGCTAC

AACCGCTTCCGCCAGTTTTGCAACATCCCCGAGGACCAGCGCGCCGAGTACAGCAC

CGACCACCATTTTGTAAACGGCGGCTACATGCCCTACAAAAGCAGTTCCATTGGCAA

GGCGAACAAGGGCAAGAGTCAGAAGGACTTTGTCGTCAAGTACTTCTGGAGGGGGC

CCCGTGTTGAGAACAGGTCGCCCGACGCCGACTTCAAGAGCTATCACGACGAGTAC

CACCGGAGGACCGCCGACATCGCGAACAGCGTCATCACCAAAATCCTGCAGGCGTT

GACAACCCGCTTCCCAGACTTTGACCCCGCTGAGTACAAGGACAACATAAACAGCC
```

-continued

```
ACCACATGTTTTTCAGCAATCGCCTGTATCCCGACAACGAGCCGGAGAAAGGAGAG

AACGTGGAGTACCGCCTGGTTCCGCATCGAGATCTCAGTTTCGTCACCCTCGCCCAC

CAGATCCCCGCAGACAACGGCTACCAGGGCCTGTTCGTTTTCACCGGCGACGGGAA

GAAGGTCTGTGTGCCGCCCATCCGCAACAGCTACCTCGTCTTCATGGGGCAGGCGAT

GTCCTATCTCACCAACAAGTACCTGCCTGCCGGCCTGCATGGTGTCGACTTTCCGGA

GAAGAACTGTTTTGAGGGCAGCGAGCGGTCGTCCCTTATTTCGTTTTACGAGCCGCA

CGACCACATGATGCCTTCGAAGGCGCTGACCCCGAAAGATGATGAAATTTTTGATAG

AGGCTGCTCCTTTTTCGATGATATTGGTGTCGATAAGACTGGCACGACTTATATGTA

CGTCAAAAATAAGTTCCACGAGGGATATTATCTATAG
```

>KabC (*Grateloupia filicina*)
```
ATGACTTCGTTTGATTTCGTTGCGAAGACCTTTGACTTTGCTCCCGTGAAAGCAGATG

AACTGAAATGGTACCCCAGGTCTGCTCTCCCTCCAGAAATCCCTGTCATCGATCTGA

ACAACGTCAACACTGAAGAAGAGCTGGCTCAATTCTTGGTTGATATTCGCAAATCTG

GACTCTTCTATGTGGTCAACCATGACATTCCAGAAGAGATATCCATCCAAACTTACA

ACGAATTTCGTGAGTTTTGCAAGCTCCCTGAGGAGGCCAGACAGAAGTATAACACT

GATAGATGCTTCTTTAATGGCGGTTACGTTCCTTTCAAAGCCACTTCAATTAATGGA

GGCAACAAGAACAAACAGCAGAGAGATTTTGTCGTAAAATTCTTCTGGAGAGGGCC

GCATGTCGTCAACAGGAGTCCGAACGAGCGCTTCGCAAAATGGCACCACCAATATC

ACACAAGAACTGCTGAACTAGGTGAAAAGGTCATGACTACCATCGCGAAAGCTTTG

AAGACACGCTTTCCGGATTTTGACCCTGCTGAGTTGGAAGACAACGTCAACCCGCAC

AACATGATTTTCAGTAATCGAATCTACCCAGAGTTTCCACCCAGCGAAGGAGAGGAT

GCCGAATACCGACTTACTCCTCATAGGGATATCAGTTATATCACCCTCGTGAATCAA

ACTCCGGCAAACAATGGCTTTAAGGCTCTTTTCATAGTAACTGGTGATGGGGAGAGA

GTCTATGTTCCTCCCATCCGCAACAGTTACTTGGTATTCATTGGACAGAGCCTTTCAT

ATCTCACCAACAAGTATCTTCCTGCCGCCCTGCATGGGGTGGCCTTTCCAGACGGAA

ATTTAGAAGGATGTGAGAGGGCATCTTTGGTTTCCTTCTACGAGCCTTACGATCGTA

TGGTGCCTTCAAAAAACATCAAGCCCACAGCAGAGGAGATTGCTCCGAAAAGCTGT

TCATTTTACGATTCTATCGGATGTGATAAGACTGGCACGACATTTACGGACGTGAGG

GCGAAATTTCATTCCGGATACTATGTTTGA
```

SEQ ID NOs: 11-15, respectively:
DsKabA (*Digenea simplex*):
```
MSITTMKGVTSESPAEALSRFQTTGLTLNNPKDLYWMTEFLKEEFYDKGNYYYPIKTVC

DGELIETELFCPFEPKLSPHYIQLYNSRDERSNLYAVPPKKTDMKKYNRINCEKMGSLM

APNSNYDDTEMVSLFYSMMYYLNDQTAHLKLPEEDIQPELVDELNDHVLQYLSVFLSIF

KPREPQDLERIWNFLDFYQPYFKKVDGKIILHEKYQGRTPPQIGLIKKITGYVLERFAPKK

NITQVIYEVIRYIKGIKQEIKIRGDKSFTLSLKEYDEFRDQVTSSPMAHSITDLTYDDFSYK

AYMNPLFIKLEDLTSEIITYFNDVCTCDRERLDDDPFNSVFILRDLHSLNYVKSCDLVVK

HAHDKLSKFLEIKQTLLKESTNENEKKAIAQMIKTREDSLIGYTIHEICCVINGYARDHK

PLMKDYLEKNIFKKLKATN
```

PpKabA (*Palmaria palmata*):
```
MLPPAFLPPAVHSLFRGGLLQRPEHVGPTPTATPSAASIRAHRAPTTLVMVAHGRRRLER

PTAALPTGARRTGLTLTDPADLHSMVAHLKKENFDKGNCNYPIKTVCDGELIDVQFAFP

FEPKLSPHYAALYNSRDERSQLYAVPPSTTDMKKYNRINCEKMGALLAPNSAYGDTEIV
```

SLFYSMMYYLNDQTAHFKLPEEEIQYELVDELNDNVLQYLSIFLGVFKPRDAADLERIW

DFLEFYQPYFHKVDGRIELDAKYSGQTPPQVALVSKIAGYAADRFGASKNITQIIYEVIR

YVKGIKEEIKIRCDKGFSLTLSEYDAFRDNVTSSPMAHSVTDLTHDAFSYEAYTNPVFNE

LENLTSQVITYVNDVCTCDRERLDDDPFNSVFILKNRDGLNFAEACDRVVGEVVKKTAR

FLETKERLLAEAADEDGRAAMAQMIKTREDSIIGYMLHEVCCVTDGYARDHKPLMKDY

LEKTMFGEVASGAM

PhKabA (*Palmaria hecatensis*):
MPPPAFLPPAVRSLFRGAPLQRLQHVGPIQSATPSAASIRARRAARTLVMVDAGPERPTA

APPTGARRTDLTLTDPADLALMVAHLKREHFDKGYCTYPIKTVCDGELIDVQFSFPFEPK

LSPHYAALYNSRDERSQLYAVSPNTTDMKKYNRINCEKMGALLAPNSAYGDTEMVSLF

YSMMYYLNDQTAHFKLPEEEIQYELVDELNDNVLQYLSIFLGVFEPRDAADLERIWDFL

EFYQPYFNKVGGKIVLDAKYSGQTPPQVALVTKIAGYAAGREGATKNITQIIYEVIRYVK

GIKQEIKIRCDKSFTLNLAEYDAFRDQVTSSPMAHSVTDLTHDAFSYKAYTNPVENDLE

NLTSQIITYVNDVCTCDRERLDDDPFNSVFILKNRDGLNFADACDLVVGEVVKKTAKFL

ETKDRLLAEAADEEGRAAIAQKIKTREDSIIGYMMHEVCCVTDGYARDHKPLMKEYLE

KAMFGEASSGAL

ReKabA (*Rhodophysema elegans*):
MSPSAFLPLAGPLAFRRASLQRLNHTRTLPPTVAPSRAPMTPFMVDTSRGHPATAAPPM

GARRSLTLTDPADLALMVSHLKREHFDKGDYLYPIKTVCAGEDIDVRFAIPFEPRLSSHY

AALYNSRNDRAKLYAVPPRTTDMRKYNRINCEKMGALLAPNSAYGDTEAVSLFYSMM

YYLNDQTAICKLPEDEIELRLVDELNDNVLQYLGIFLSVFEPRDAADLERIWDFLDFYQP

YFRKAGRRIVLDDKYLGQTPPQVALVTTIANYVAERFGATKNITQVVYEVIRYVKGIKQ

EVKIRCDKGFTLSLAEYDDFRDQVTSSPMAHSVTDLTHDAFSYEAYKNPVFNSLENLTS

QVITYINDVCTCDRERLDKDPFNSVFILKDRDGLNFADACDLVVAEIEKKMAKFLETKK

QLLSEAADEERRTAMAQMIKTREDSIIGYMMHEVCCVTDGYARDHKPKMKEYLEKAM

FGEVSREAM

GfKabA partial sequence (*Grateloupia filicina*):
MNLILRSNMPIFPSCAFLSSSTTTTFIQPLVKRIHSVCPNPVRHEPVSANRRLVMRLAWNP

TPTQQLTTESPTEALSRLQTTGLTLTDPKDLYWMTDFLEQQFYSKRNPNYPMKTICDGE

LIETEFHCPYQPKLSPHYMRLCNTKHERSLLYSIPPNTTDMNKYNRINCEKFASLVAPNS

NYEDTEAVALMYSMMYYLNDQTAHLKLPEDMIQPQLIDELNDNVLQYLAVFLSIFEPR

DPEDLERIWDFLDFYQKYFNKIDGKIVLDEKYKGPVPPQIALINKITQYISKRFAPTKNITQ

FIYEVIRYIKGIKQEVYIRCDKSFTLSLKEYDEFRDQVTSSPMAHAVTDMTYDNFSYKLY

LNPLFTELENLTSELITYFNDVCTCDRERLDNDPFNSVFILKDLYGGTYAQSCDLVVSET

RKKFSKFLEIKQILLDGAADETEKQAIAQMIK

SEQ ID NOs: 16-20, respectively:
DsKabA (*Digenea simplex*):
ATGAGTATTACCACTATGAAAGGAGTTACATCAGAGAGTCCTGCCGAAGCGCTTTCC

CGCTTCCAAACTACTGGATTGACGTTGAACAACCCCAAGGACCTTTACTGGATGACA

GAATTTTTGAAGGAAGAATTTTACGACAAGGGAAACTATTATTATCCCATCAAAACG

GTATGTGATGGCGAACTCATCGAAACCGAGCTCTTCTGTCCCTTCGAACCAAAGCTC

AGTCCACATTACATTCAATTATACAACTCTCGTGATGAGCGATCCAACTTGTACGCC

GTTCCGCCCAAGAAAACAGACATGAAAAAGTACAATCGTATAAATTGTGAGAAAAT

-continued

```
GGGTTCTTTGATGGCCCCTAATTCCAATTATGACGACACAGAAATGGTTTCTCTCTTC

TACTCCATGATGTACTACCTCAATGATCAGACCGCTCATCTTAAGCTCCCTGAAGAA

GATATTCAACCTGAGCTTGTTGATGAACTCAACGACCATGTCTTACAGTATCTAAGT

GTGTTCCTTAGCATCTTTAAACCGCGTGAACCTCAAGATTTGGAGCGAATCTGGAAT

TTTTTGGACTTTTACCAGCCATATTTCAAGAAAGTTGATGGCAAGATTATCTTGCACG

AGAAATATCAGGGGCGTACTCCACCACAAATCGGTTTGATCAAGAAAATAACAGGT

TATGTATTAGAGAGGTTTGCTCCGAAAAAGAATATCACTCAAGTCATCTACGAGGTC

ATCAGATATATCAAGGGAATCAAGCAAGAAATTAAGATTCGAGGTGATAAGAGCTT

CACTCTGTCTCTCAAAGAGTATGATGAGTTCCGTGACCAAGTTACGTCCAGCCCAAT

GGCTCATTCGATTACAGATCTTACTTATGACGACTTCTCTTACAAGGCATACATGAA

CCCACTCTTCATCAAGCTGGAAGATCTAACCTCTGAGATCATCACGTACTTCAACGA

CGTTTGCACATGTGATCGCGAGAGACTGGACGATGATCCTTTCAACTCTGTTTTCATT

CTGAGAGATCTTCACAGTCTCAACTATGTGAAGTCATGTGATCTTGTCGTTAAGCAT

GCACATGACAAGCTATCAAAATTCTTGGAGATCAAGCAGACTCTTTTGAAAGAATCT

ACAAACGAAATGAGAAAAAGGCCATTGCCCAGATGATTAAGACTCGTGAAGATTC

CTTGATTGGATATACGATTCATGAAATTTGCTGTGTTACAAATGGGTATGCTCGTGA

CCACAAGCCCTTGATGAAAGATTATTTGGAGAAAAATATCTTTAAGAAACTCAAGG

CGACAAATTAA

PpKabA (Palmaria palmata):
ATGCTTCCTCCTGCCTTCCTCCCTCCGGCCGTGCACTCCCTCTTCCGCGGCGGCCTGC

TGCAGCGTCCGGAACACGTTGGTCCAACCCCAACTGCAACGCCTTCCGCCGCTTCGA

TCCGCGCACACCGCGCACCAACGACGCTCGTCATGGTCGCGCACGGTCGGCGCCGT

CTCGAACGCCCCACAGCGGCACTACCAACCGGCGCGCGACGGACCGGCTTGACGCT

CACCGACCCGGCCGACCTGCATTCCATGGTGGCGCACCTGAAAAAGGAGAACTTCG

ACAAGGGCAACTGCAACTACCCAATCAAGACGGTGTGCGATGGAGAACTCATCGAC

GTCCAGTTCGCCTTCCCGTTTGAACCGAAGCTGAGCCCGCACTACGCCGCCCTGTAC

AATTCGCGTGACGAGCGCTCCCAGCTGTACGCTGTCCCGCCTAGTACTACAGATATG

AAAAAATACAACCGCATCAACTGCGAGAAGATGGGCGCCCTGCTCGCGCCGAACTC

TGCGTATGGCGACACGGAGATAGTGTCGCTGTTCTATTCGATGATGTATTATCTCAA

TGACCAGACGGCGCACTTCAAGCTACCAGAGGAAGAGATCCAGTACGAGCTCGTGG

ACGAGCTCAACGACAATGTGCTGCAGTATCTCAGCATATTTCTGGGCGTTTTCAAGC

CGCGCGATGCTGCGGATTTGGAGCGCATTTGGGACTTTCTCGAGTTTTACCAGCCCT

ATTTTCACAAGGTCGACGGGAGGATTGAGTTAGATGCCAAGTATAGCGGGCAGACG

CCGCCGCAGGTCGCGCTTGTCTCGAAGATTGCGGGGTACGCCGCGGATCGGTTCGGC

GCGTCAAAGAACATCACCCAGATCATCTACGAGGTCATTCGATATGTCAAGGGCATC

AAGGAGGAGATCAAGATCAGGTGCGACAAGGGCTTTAGCCTCACCCTCTCCGAGTA

CGACGCGTTCCGGGACAATGTCACATCGAGCCCGATGGCGCACTCCGTAACCGACC

TGACGCACGATGCGTTCTCCTACGAGGCCTACACGAACCCCGTCTTCAACGAGCTGG

AAAACCTGACCTCCCAAGTCATCACCTACGTCAACGACGTGTGTACGTGCGACCGG

GAGCGGCTGGACGACGACCCGTTCAATTCGGTCTTTATTCTGAAAAATCGCGACGGT

CTGAACTTCGCCGAAGCGTGCGATCGCGTTGTCGGCGAGGTGGTGAAGAAGACGGC
```

-continued

```
AAGGTTCCTGGAGACGAAGGAGCGGCTTCTTGCGGAGGCTGCTGATGAAGACGGGA

GGGCGGCCATGGCGCAGATGATCAAGACGCGCGAAGACTCGATCATCGGGTACATG

CTGCACGAGGTCTGCTGCGTGACGGATGGGTATGCGCGCGACCACAAGCCGTTGAT

GAAAGACTATCTGGAGAAGACGATGTTTGGTGAGGTGGCCAGCGGAGCAATGTAG
```

PhKabA (*Palmaria hecatensis*):
```
ATGCCTCCTCCCGCCTTCCTCCCTCCAGCCGTGCGCTCCCTCTTCCGCGGCGCCCCGC

TGCAGCGTCTGCAACACGTCGGTCCAATCCAAAGTGCAACGCCCTCCGCTGCTTCGA

TCCGCGCACGCCGTGCAGCAAGGACGCTCGTCATGGTCGACGCAGGCCCGGAGCGC

CCCACAGCAGCACCACCAACCGGCGCGCGACGGACCGACTTGACGCTAACGGACCC

GGCAGATCTGGCGCTCATGGTCGCCCATCTGAAAAGGGAGCACTTCGACAAGGGGT

ACTGCACCTACCCGATAAAGACGGTGTGCGATGGAGAACTCATCGACGTCCAGTTCT

CCTTCCCGTTCGAGCCGAAGCTGAGCCCGCACTACGCGGCCCTGTACAATTCGCGTG

ACGAGCGCTCGCAGCTGTACGCTGTCTCGCCAAATACTACGGATATGAAGAAGTAC

AACCGCATCAACTGCGAGAAGATGGGCGCGCTGCTTGCCCCGAACTCTGCATATGG

CGACACGGAGATGGTTTCGCTGTTCTACTCGATGATGTATTATCTCAATGACCAGAC

GGCGCACTTCAAGCTGCCCGAGGAGGAGATCCAGTACGAGCTTGTGGACGAGCTCA

ACGACAATGTGCTGCAGTATCTCAGCATTTTTCTGGGCGTGTTCGAGCCGCGCGATG

CTGCGGACTTGGAGCGTATTTGGGACTTTCTCGAGTTTTACCAGCCGTATTTTAACAA

GGTCGGCGGGAAGATCGTGCTGGATGCCAAGTACAGCGGGCAGACGCCGCCGCAGG

TCGCGCTCGTCACGAAGATCGCGGGGTACGCCGCGGGGCGCTTCGGCGCGACGAAG

AACATCACGCAGATCATCTACGAGGTCATTCGATATGTTAAGGGCATCAAGCAGGA

GATCAAGATCAGGTGCGACAAGAGCTTTACCCTCAACCTCGCGGAGTACGACGCGT

TCCGCGACCAGGTCACATCGAGCCCGATGGCGCACTCTGTAACCGACTTGACGCAC

GACGCCTTCTCCTACAAGGCCTACACGAACCCCGTCTTCAACGACCTGGAAAACCTG

ACCTCCCAAATCATCACCTATGTCAACGACGTATGCACTTGTGACCGCGAGCGGCTG

GACGACGATCCGTTCAACTCGGTCTTTATTCTGAAAAATCGCGACGGCCTCAACTTC

GCCGACGCGTGCGACCTCGTTGTCGGCGAGGTCGTAAAGAAGACGGCGAAGTTCCT

GGAGACTAAGGATAGGCTTCTTGCGGAAGCTGCTGATGAAGAGGGGAGGGCGGCTA

TTGCGCAGAAGATCAAGACGCGCGAGGACTCGATCATCGGGTACATGATGCACGAG

GTTTGCTGCGTGACGGACGGGTATGCGCGCGACCACAAGCCGCTGATGAAAGAGTA

TCTGGAGAAGGCGATGTTTGGTGAGGCGAGCAGCGGAGCCCTGTAG
```

ReKabA (*Rhodophysema elegans*):
```
ATGTCTCCTTCGGCCTTTCTCCCCCTAGCCGGGCCCTTAGCCTTCCGGCGGGCCTCGC

TGCAGCGTCTAAATCATACCCGTACCCTCCCACCCACCGTCGCTCCGTCCCGCGCAC

CAATGACGCCCTTCATGGTCGACACCAGCCGCGGGCACCCTGCTACAGCAGCCCCA

CCTATGGGCGCGCGCCGCAGCCTGACGCTGACGGACCCGGCCGATCTGGCGCTCAT

GGTCTCCCACCTGAAGCGCGAGCATTTCGACAAGGGCGACTACCTTTACCCGATCAA

AACCGTATGCGCCGGCGAGGACATCGACGTCCGCTTCGCTATCCCCTTCGAGCCGCG

CCTCAGCTCGCACTATGCGGCCCTGTACAACTCGCGAAACGATCGCGCCAAGCTTTA

CGCCGTCCCGCCGCGGACGACTGACATGCGTAAGTACAACCGCATCAACTGTGAGA

AGATGGGCGCCCTGCTCGCGCCCAACTCTGCCTACGGCGACACAGAGGCCGTCTCTC
```

-continued

```
TCTTCTACTCGATGATGTACTACCTCAACGACCAGACGGCGATCTGCAAGCTGCCCG

AGGACGAAATCGAGCTTCGCCTCGTCGACGAGCTCAACGACAACGTGCTCCAATAT

CTCGGCATCTTCCTCTCCGTCTTCGAGCCGCGCGATGCCGCTGATTTGGAGCGTATCT

GGGACTTTCTAGACTTTTACCAGCCGTACTTCCGCAAGGCCGGCCGGAGGATCGTGC

TGGACGACAAATACCTCGGGCAGACGCCGCCGCAGGTCGCGCTTGTCACAACGATC

GCAAACTACGTCGCCGAACGCTTCGGCGCGACGAAGAACATCACGCAGGTCGTCTA

CGAGGTGATTCGCTATGTTAAGGGCATCAAGCAGGAGGTGAAGATCAGGTGCGACA

AGGGATTCACCCTCTCACTCGCCGAGTACGACGATTTCCGCGACCAGGTCACGTCCA

GCCCGATGGCGCACTCCGTGACCGACCTCACCCACGACGCCTTCTCCTACGAGGCAT

ATAAGAACCCGGTCTTCAACTCCCTGGAGAACCTGACCTCCCAGGTCATTACCTACA

TCAACGACGTGTGCACGTGTGACCGAGAGCGGCTAGACAAGGACCCGTTTAACTCG

GTGTTCATTCTGAAAGACCGCGACGGTCTGAACTTCGCCGACGCGTGCGACCTCGTC

GTCGCCGAGATCGAAAAGAAAATGGCAAAGTTCCTCGAGACGAAGAAGCAGCTTCT

GTCGGAGGCTGCTGATGAAGAGCGCAGAACAGCCATGGCGCAGATGATCAAGACGC

GGGAGGACTCGATCATCGGCTACATGATGCACGAGGTCTGCTGCGTGACGGACGGG

TATGCGCGCGACCACAAGCCGAAGATGAAGGAGTATCTGGAGAAGGCGATGTTTGG

GGAGGTGAGCAGGGAAGCCATGTAG
```

GfKabA partial sequence (*Grateloupia filicina*):
```
ATGAATTTGATCCTCCGCAGTAACATGCCTATTTTCCCATCTTGCGCTTTTCTCTCAT

CCTCAACCACTACCACTTTCATTCAACCTCTTGTCAAACGTATCCACTCCGTTTGCCC

CAATCCAGTACGCCATGAGCCAGTTTCAGCAAACCGTCGCCTAGTCATGCGACTTGC

CTGGAATCCTACACCCACTCAACAACTTACCACAGAGAGTCCTACCGAAGCACTTTC

CCGCCTTCAAACCACTGGACTAACCCTGACTGACCCGAAGGACCTTTACTGGATGAC

CGATTTTTTGGAACAACAATTTTACTCAAAAAGAAACCCCAACTATCCCATGAAAAC

CATCTGCGACGGCGAACTCATCGAGACCGAATTTCACTGTCCATACCAACCCAAACT

CAGCCCTCATTATATGAGGTTGTGCAACACTAAGCATGAAAGATCTCTCTTGTACTC

AATTCCACCAAACACCACAGATATGAACAAGTACAACCGAATTAATTGCGAGAAGT

TCGCCTCTTTGGTAGCCCCGAATTCCAATTATGAAGATACAGAGGCTGTTGCCCTCA

TGTACTCCATGATGTACTATCTCAATGATCAGACTGCCCATCTTAAACTTCCTGAGG

ATATGATTCAGCCTCAACTTATTGATGAACTCAACGATAACGTATTGCAGTATCTCG

CTGTGTTTCTAAGCATCTTCGAACCCCGCGATCCGGAAGATTTGGAGCGCATCTGGG

ACTTCTTAGACTTTTATCAGAAGTACTTCAACAAAATAGACGGAAAGATTGTCTTGG

ATGAAAAGTACAAAGGACCAGTCCCGCCTCAAATTGCTTTGATTAACAAAATCACCC

AATATATCTCGAAGAGATTTGCTCCGACGAAGAACATAACTCAGTTCATCTACGAGG

TCATCAGATACATCAAGGGGATCAAGCAAGAGGTCTACATTCGATGTGATAAGAGT

TTTACTCTTTCTCTCAAGGAGTATGATGAATTTCGTGATCAAGTGACGTCCAGCCCG

ATGGCACATGCTGTGACAGATATGACCTATGACAACTTCTCTTATAAGCTCTACCTG

AACCCGCTTTTCACCGAACTGGAGAATCTGACTTCAGAACTGATCACCTACTTCAAC

GACGTTTGCACATGTGATCGCGAGAGACTGGACAATGATCCTTTCAACTCTGTGTTC

ATTCTGAAAGACCTTTATGGTGGTACCTATGCACAAAGTTGTGATCTTGTCGTGAGC
```

-continued

```
GAAACGCGCAAAAAGTTCTCTAAATTTTTGGAGATCAAACAAATTCTTCTTGATGGG

GCAGCAGACGAAACCGAGAAACAAGCTATTGCCCAGATGATTAAG
```

EXEMPLARY EMBODIMENTS

1. A process for preparing a compound having the formula,

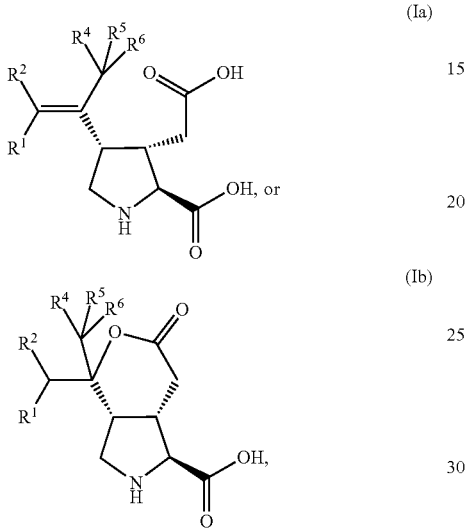

or a salt thereof, wherein the compound or a salt of Formula (Ia) or (Ib) is prepared by cyclizing a compound of formula II:

or a salt thereof; wherein the cyclization comprises contacting compound of Formula II with a recombinant KabC polypeptide; wherein
(a) at least one of $R^1$, $R^2$, $R^3$, $R^4$, $R^5$ or $R^6$ is hydrogen; and
(b) $R^1$ is hydrogen, halogen, —CN, —C(O)OH, —$CONH_2$, —$NO_2$, —$SO_2Cl$, —$SO_2NH_2$, —$NHNH_2$, —$NHSO_2CH_3$, —$N_3$, —$NR^{1A}R^{1B}$, —$OR^{1A}$, —$SR^{1A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^2$ is hydrogen, halogen, —CN, —C(O)OH, —$CONH_2$, —$NO_2$, —$SO_2Cl$, —$SO_2NH_2$, —$NHNH_2$, —$NHSO_2CH_3$, —$N_3$, —$NR^{2A}R^{2B}$, —$OR^{2A}$, —$SR^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^3$ is hydrogen, halogen, —CN, —C(O)OH, —$CONH_2$, —$NO_2$, —$SO_2Cl$, —$SO_2NH_2$, —$NHNH_2$, —$NHSO_2CH_3$, —$N_3$, —$NR^{3A}R^{3B}$, —$OR^{3A}$, —$SR^{3A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^4$ is hydrogen, halogen, —CN, —C(O)OH, —$CONH_2$, —$NO_2$, —$SO_2Cl$, —$SO_2NH_2$, —$NHNH_2$, —$NHSO_2CH_3$, —$N_3$, —$NR^{4A}R^{4B}$, —$OR^{4A}$, —$SR^{4A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^5$ is hydrogen, halogen, —CN, —C(O)OH, —$CONH_2$, —$NO_2$, —$SO_2Cl$, —$SO_2NH_2$, —$NHNH_2$, —$NHSO_2CH_3$, —$N_3$, —$NR^{5A}R^{5B}$, —$OR^{5A}$, —$SR^{5A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^6$ is hydrogen, halogen, —CN, —C(O)OH, —$CONH_2$, —$NO_2$, —$SO_2Cl$, —$SO_2NH_2$, —$NHNH_2$, —$NHSO_2CH_3$, —$N_3$, —$NR^{6A}R^{6B}$, —$OR^{6A}$, —$SR^{6A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; any two of $R^1$, $R^2$ or $R^3$ substituents or any two of $R^4$, $R^5$ or $R^6$ substituents may optionally be joined to form a substituted or unsubstituted aryl or substituted or unsubstituted heteroaryl;
any one of $R^1$, $R^2$ or $R^3$ and any one of $R^4$, $R^5$ or $R^6$ may optionally be joined to form a substituted or unsubstituted cycloalkyl, substituted or unsubstituted aryl or substituted or unsubstituted heteroaryl; and
each $R^{1A}$, $R^{2A}$, $R^{3A}$, $R^{4A}$, $R^{5A}$, $R^{6A}$, R1B, $R^{2B}$, $R^{3B}$, $R^{4B}$, $R^{5B}$, and $R^{6B}$ is independently a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

2. The process of embodiment 1, wherein
(a) at least one of $R^1$, $R^2$, $R^3$, $R^4$, $R^5$ or $R^6$ is hydrogen; and
(b) $R^1$ is hydrogen, substituted or unsubstituted $C_1$-$C_{10}$ alkyl, substituted or unsubstituted $C_5$-$C_{10}$ aryl, or substituted or unsubstituted 5 to 10 membered heteroaryl;
$R^2$ is hydrogen, substituted or unsubstituted $C_1$-$C_{10}$ alkyl, substituted or unsubstituted $C_5$-$C_{10}$ aryl, or substituted or unsubstituted 5 to 10 membered heteroaryl;

R$_3$ is hydrogen, substituted or unsubstituted C$_1$-C$_{10}$ alkyl, substituted or unsubstituted C$_5$-C$_{10}$ aryl, or substituted or unsubstituted 5 to 10 membered heteroaryl;

R$^4$ is hydrogen, substituted or unsubstituted C$_1$-C$_{10}$ alkyl, substituted or unsubstituted C$_5$-C$_{10}$ aryl, or substituted or unsubstituted 5 to 10 membered heteroaryl;

R$^5$ is hydrogen, substituted or unsubstituted C$_1$-C$_{10}$ alkyl, substituted or unsubstituted C$_5$-C$_{10}$ aryl, or substituted or unsubstituted 5 to 10 membered heteroaryl;

R$^6$ is hydrogen, substituted or unsubstituted C$_1$-C$_{10}$ alkyl, substituted or unsubstituted C$_5$-C$_{10}$ aryl, or substituted or unsubstituted 5 to 10 membered heteroaryl;

any two of R$^1$, R$^2$ or R$^3$ substituents or any two of R$^4$, R$^5$ or R$^6$ substituents may optionally be joined to form a substituted or unsubstituted C$_5$-C$_{10}$ aryl or substituted or unsubstituted 5 to 10 membered heteroaryl; and any one of R$^1$, R$^2$ or R$^3$ and any one of R$^4$, R$^5$ or R$^6$ may optionally be joined to form a substituted or unsubstituted C$_3$-C$_8$ cycloalkyl, substituted or unsubstituted C$_5$-C$_{10}$ aryl or substituted or unsubstituted 5 to 10 membered heteroaryl.

3. The process of embodiment 1, wherein
(a) at least one of R$^1$, R$^2$, R$^3$, R$^4$, R$^5$ or R$^6$ is hydrogen; and
(b) R$^1$ is hydrogen or substituted or unsubstituted C$_1$-C$_{10}$ alkyl; R$^2$ is hydrogen or substituted or unsubstituted C$_1$-C$_{10}$ alkyl; R$^3$ is hydrogen or substituted or unsubstituted C$_1$-C$_{10}$ alkyl; R$^4$ is hydrogen or substituted or unsubstituted C$_1$-C$_{10}$ alkyl; R$^5$ is hydrogen or substituted or unsubstituted C$_1$-C$_{10}$ alkyl; R$^6$ is hydrogen or substituted or unsubstituted C$_1$-C$_{10}$ alkyl;

any two of R$^1$, R$^2$ or R$^3$ substituents or any two of R$^4$, R$^5$ or R$^6$ substituents may optionally be joined to form a substituted or unsubstituted C$_5$-C$_{10}$ aryl or substituted or unsubstituted 5 to 10 membered heteroaryl; and any one of R$^1$, R$^2$ or R$^3$ and any one of R$^4$, R$^5$ or R$^6$ may optionally be joined to form a substituted or unsubstituted C$_3$-C$_8$ cycloalkyl, substituted or unsubstituted C$_5$-C$_{10}$ aryl or substituted or unsubstituted 5 to 10 membered heteroaryl.

4. The process of any one of embodiments 1 to 3, wherein R$^1$, R$^2$, R$^3$, R$^4$, R$^5$ and R$^6$ are hydrogen.

5. The process of any one of embodiments 1 to 4, wherein the process comprises contacting the compound of Formula II, or a salt thereof, with a purified KabC polypeptide and a α-keto-glutarate.

6. The process of any one of embodiments 1 to 5, wherein the process for preparing the compound of Formula II, or a salt thereof, comprises:
a. contacting a compound of Formula III:

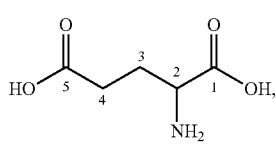

Formula III or a salt thereof, with a compound of Formula IV:

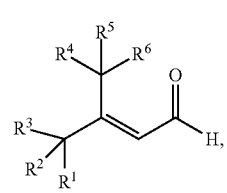

Formula IV or a salt thereof, to form an imine, and
b. reducing the imine to produce the compound of Formula II.

7. The process of any one of embodiments 1 to 6, wherein the contacting comprises contacting the compound of Formula II, or a salt thereof, with a recombinant microorganism expressing the recombinant KabC polypeptide.

8. The process of any one of embodiments 1-7, wherein the recombinant KabC polypeptide comprises an amino acid sequence that is at least 80% identical to any of SEQ ID NOs: 1-5.

9. The process of any one of embodiments 1-7, wherein the recombinant KabC polypeptide is encoded by a polynucleotide comprising a sequence that is at least 80% identical to any of SEQ ID NOs: 6-10.

10. The process of any one of embodiments 7-9, wherein the microorganism further expresses a recombinant KabA polypeptide.

11. The process of embodiment 10, wherein the recombinant KabA polypeptide comprises an amino acid sequence that is at least 80% identical to any of SEQ ID NOs: 11-15.

12. The process of embodiment 10, wherein the recombinant KabA polypeptide is encoded by a polynucleotide comprising a sequence that is at least 80% identical to any of SEQ ID NOs: 16-20.

13. The process of any one of embodiments 7-12, wherein the recombinant microorganism is a bacterium.

14. The process of embodiment 13, wherein the bacterium is *E. coli*.

15. A process for preparing a compound having the formula,

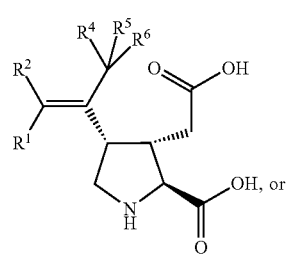

(Ia)

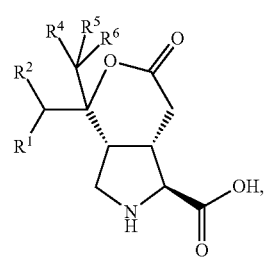

(Ib)

or a salt thereof, wherein the process comprises:
contacting a compound of Formula III:

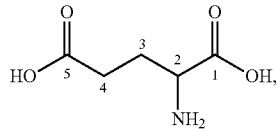

Formula III or a salt thereof, with a compound of Formula V:

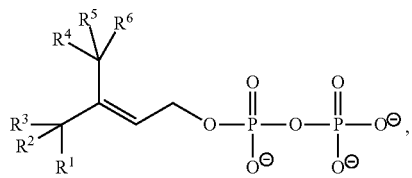

Formula V or a salt thereof, a recombinant KabA polypeptide, a recombinant KabC polypeptide, and a α-keto-glutarate.

16. The process of embodiment 15, wherein the recombinant KabA polypeptide and recombinant KabC polypeptide are each expressed by a recombinant microorganism.
17. The process of embodiment 15 or 16, wherein the recombinant KabC polypeptide comprises an amino acid sequence that is at least 80% identical to SEQ ID NO: 1.
18. The process of any one of embodiments 15-17, wherein the recombinant KabC polypeptide is encoded by a polynucleotide that is at least 80% identical to SEQ ID NO: 2.
19. The process of any one of embodiments 15-18, wherein the recombinant KabA polypeptide comprises an amino acid sequence that is at least 80% identical to SEQ ID NO: 3.
20. The process of any one of embodiments 15-19, wherein the recombinant KabA polypeptide is encoded by a polynucleotide that is at least 80% identical to SEQ ID NO: 4.
21. The process of any one of embodiments 15-20, wherein the recombinant KabA polypeptide and the recombinant KabC polypeptide are expressed by the same recombinant microorganism.
22. The process of any one of embodiments 15-21, wherein the microorganism is a bacterium.
23. The process of embodiment 22, wherein the bacterium is *E. coli*.
24. A compound of Formula II:

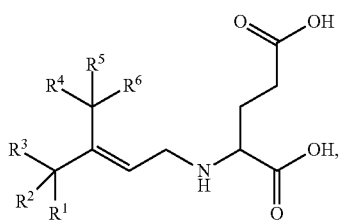

Formula II or a salt thereof.

25. A compound of Formula VI:

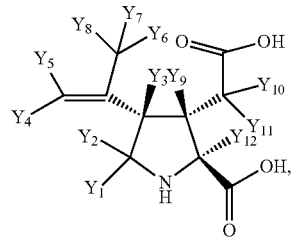

Formula VI or a salt thereof, wherein:
one of $Y_1, Y_2, Y_3, Y_4, Y_5, Y_6, Y_7, Y_8, Y_9, Y_{10}, Y_{11}$, or $Y_{12}$ is a hydrogen that is isotopically enriched with deuterium or tritium, and the rest of $Y_1, Y_2, Y_3, Y_4, Y_5, Y_6, Y_7, Y_8, Y_9, Y_{10}, Y_{11}$, and $Y_{12}$ are non-enriched hydrogen atoms.

26. A compound of Formula VII:

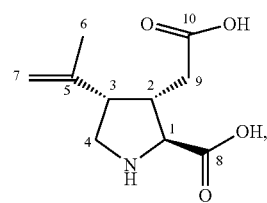

Formula VII or a salt thereof, wherein:
1, 2, 3, 4, 5, 6, 7, 8, 9, and 10 are carbon atoms;
and at least one of 1, 2, 3, 4, 5, 6, 7, 8, 9, or 10 carbon atom is isotopically enriched with carbon-13 or carbon-14.

27. A compound of Formula VIII:

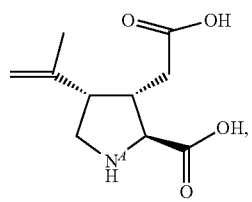

Formula VIII or a salt thereof, wherein $N^4$ is a nitrogen atom, and $N^4$ is isotopically enriched with nitrogen-15.

28. A recombinant polynucleotide encoding a KabA polypeptide, a KabC polypeptide, or both.
29. The recombinant polynucleotide of embodiment 28, wherein the polynucleotide encodes both the KabA polypeptide and the KabC polypeptide.
30. The recombinant polynucleotide of embodiment 28 or 29, wherein the recombinant KabC polypeptide comprises an amino acid sequence that is at least 80% identical to any of SEQ ID NOs: 1-5.
31. The recombinant polynucleotide of any one of embodiments 28-30, wherein the recombinant KabC polypeptide is encoded by a polynucleotide that is at least 80% identical to any of SEQ ID NOs: 6-10.
32. The recombinant polynucleotide of any one of embodiments 28-31, wherein the recombinant KabA polypeptide comprises an amino acid sequence that is at least 80% identical to any of SEQ ID NOs: 11-15.

33. The recombinant polynucleotide of any one of embodiments 28-32, wherein the recombinant KabA polypeptide is encoded by a polynucleotide that is at least 80% identical to any of SEQ ID NOs: 16-20.

34. The recombinant polynucleotide of any one of embodiments 28-33, wherein the KabA polypeptide, the KabC polypeptide, or both is a *Digenea* spp. polypeptide, a *Palmaria* spp. polypeptide, a *Rhodophysema* spp. polypeptide, or a *Grateloupia* spp. polypeptide; optionally wherein the *Digenea* spp. is *Digenea simplex*, the *Palmaria* spp. is *Palmaria palmata* or *Palmaria hecatensis*, the *Rhodophysema* spp. is *Rhodophysema elegans*, and/or the *Grateloupia* spp. is *Grateloupia filicina*.

35. An expression vector comprising the recombinant polynucleotide of any one of embodiments 28-34.

36. A recombinant cell comprising a polynucleotide of any one of embodiments 28-34, or a vector of embodiment 35.

37. The recombinant cell of embodiment 36, wherein the cell is a microorganism.

38. The recombinant cell of embodiment 36, wherein the cell is a bacterium.

39. The recombinant cell of embodiment 36, wherein the cell is *E. coli*.

40. A process for preparing a compound having the formula,

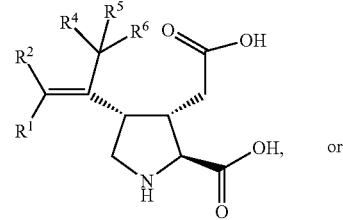
(Ia)

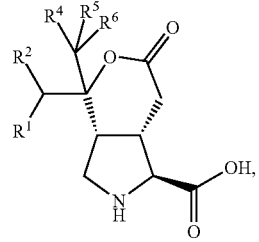
(Ib)

or a salt thereof, wherein the process comprises culturing a recombinant cell of any one of embodiments 36-39 in a culture medium.

41. The process of embodiment 40, wherein the culture medium comprises D-glucose.

42. The process of embodiment 40 or 41, further comprising isolating the compound of Formula Ia or Ib, or the salt thereof.

---

What is claimed is:

1. A process for preparing a compound having the formula

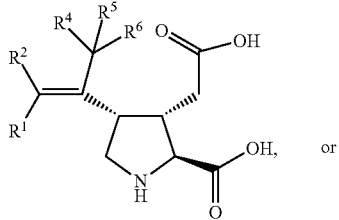

(Ia)

or

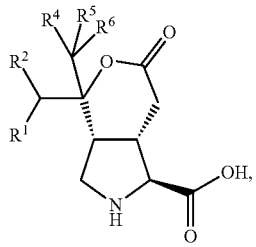

(Ib)

or a salt thereof, wherein the compound or a salt of Formula (Ia) or (Ib) is prepared by cyclizing a compound of Formula II:

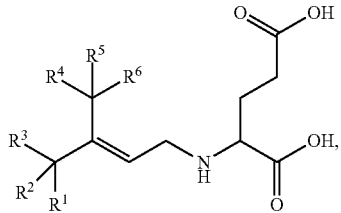

Formula II or a salt thereof; wherein the cyclization comprises contacting the compound of Formula II or a salt thereof with ferrous iron, an α-ketoglutarate (αKG), L-ascorbate and a purified recombinant KabC polypeptide; wherein:

(a) at least one of $R^1$, $R^2$, $R^3$, $R^4$, $R^5$ or $R^6$ is hydrogen; and (b) $R^1$ is hydrogen, halogen, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{1A}$R$^{1B}$, —OR$^{1A}$, —SR$^{1A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{2A}$R$^{2B}$, —OR$^{2A}$, —SR$^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{3A}$R$^{3B}$, —OR$^{3A}$, —SR$^{3A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{4A}$R$^{4B}$, —OR$^{4A}$, —SR$^{4A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{5A}$R$^{5B}$, —OR$^{5A}$, —SR$^{5A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is hydrogen, halogen, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{6A}$R$^{6B}$, —OR$^{6A}$, —SR$^{6A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

any two of $R^1$, $R^2$ or $R^3$ substituents or any two of $R^4$, $R^5$ or $R^6$ substituents may optionally be joined to form a substituted or unsubstituted aryl or substituted or unsubstituted heteroaryl;

any one of $R^1$, $R^2$ or $R^3$ and any one of $R^4$, $R^5$ or $R^6$ may optionally be joined to form a substituted or unsubstituted cycloalkyl, substituted or unsubstituted aryl or substituted or unsubstituted heteroaryl; and each $R^{1A}$, $R^{2A}$, $R^{3A}$, $R^{4A}$, $R^{5A}$ or $R^{6A}$, $R^{1B}$, $R^{2B}$, $R^{3B}$, $R^{4B}$, $R^{5B}$ and $R^{6B}$ is independently a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

2. The process of claim 1, wherein:

(a) at least one of $R^1$, $R^2$, $R^3$, $R^4$, $R^5$ or $R^6$ is hydrogen; and (b) $R^1$ is hydrogen, substituted or unsubstituted $C_1$-$C_{10}$ alkyl, substituted or unsubstituted $C_5$-$C_{10}$ aryl, or substituted or unsubstituted 5 to 10 membered heteroaryl;

$R^2$ is hydrogen, substituted or unsubstituted $C_1$-$C_{10}$ alkyl, substituted or unsubstituted $C_5$-$C_{10}$ aryl, or substituted or unsubstituted 5 to 10 membered heteroaryl;

$R_3$ is hydrogen, substituted or unsubstituted $C_1$-$C_{10}$ alkyl, substituted or unsubstituted $C_5$-$C_{10}$ aryl, or substituted or unsubstituted 5 to 10 membered heteroaryl;

$R^4$ is hydrogen, substituted or unsubstituted $C_1$-$C_{10}$ alkyl, substituted or unsubstituted $C_5$-$C_{10}$ aryl, or substituted or unsubstituted 5 to 10 membered heteroaryl;

$R^5$ is hydrogen, substituted or unsubstituted $C_1$-$C_{10}$ alkyl, substituted or unsubstituted $C_5$-$C_{10}$ aryl, or substituted or unsubstituted 5 to 10 membered heteroaryl;

$R^6$ is hydrogen, substituted or unsubstituted $C_1$-$C_{10}$ alkyl, substituted or unsubstituted $C_5$-$C_{10}$ aryl, or substituted or unsubstituted 5 to 10 membered heteroaryl;

any two of $R^1$, $R^2$ or $R^3$ substituents or any two of $R^4$, $R^5$ or $R^6$ substituents may optionally be joined to form a substituted or unsubstituted $C_5$-$C_{10}$ aryl or substituted or unsubstituted 5 to 10 membered heteroaryl; and any one of $R^1$, $R^2$ or $R^3$ and any one of $R^4$, $R^5$ or $R^6$ may optionally be joined to form a substituted or unsubstituted $C_3$-$C_8$ cycloalkyl, substituted or unsubstituted $C_5$-$C_{10}$ aryl or substituted or unsubstituted 5 to 10 membered heteroaryl.

3. The process of claim 1, wherein the process for preparing the compound of Formula II, or a salt thereof, comprises:

(a) contacting a compound of Formula III:

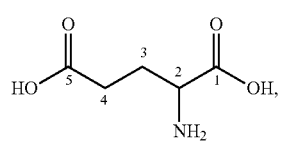

Formula III or a salt thereof with a compound of Formula IV:

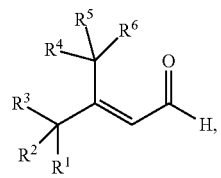

Formula IV or a salt thereof to form an imine, wherein the contacting comprises contacting the compound of Formula III with the compound of Formula IV in the presence of a magnesium co-factor and a purified recombinant KabA polypeptide; and (a) reducing the imine to produce the compound of Formula II or a salt thereof.

4. The process of claim 1, wherein the contacting comprises contacting the compound of Formula II, or a salt thereof, with a recombinant microorganism expressing the recombinant KabC polypeptide.

5. The process of claim 4, wherein the microorganism further expresses a recombinant KabA polypeptide.

6. The process of claim 4, wherein the recombinant microorganism is a bacterium.

7. A process for preparing a compound having the formula:

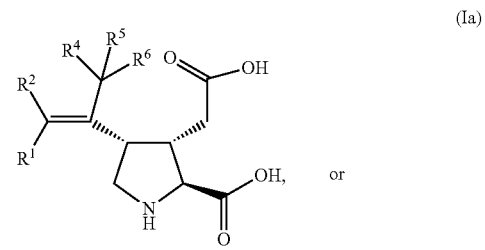

(Ia)

or

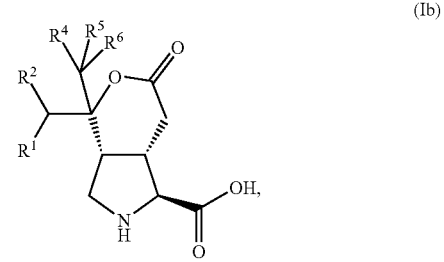

(Ib)

or a salt thereof, wherein the process comprises:

contacting a compound of Formula III:

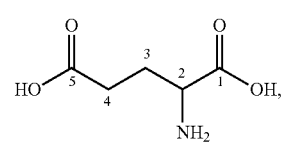

Formula III or a salt thereof, with a compound of Formula V:

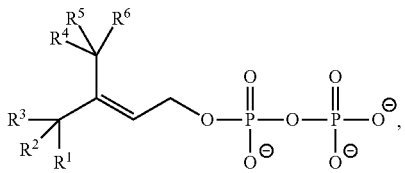

Formula V or a salt thereof, a purified recombinant KabA polypeptide, a purified recombinant KabC polypeptide, a magnesium co-factor, ferrous iron, L-ascorbate, oxygen ($O_2$), and an α-ketoglutarate, (a) wherein at least one of $R^1$, $R^2$, $R^3$, $R^4$, $R^5$ or $R^6$ is hydrogen; and (b) $R^1$ is hydrogen, halogen, —CN, —C(O)OH, —$CONH_2$, —$NO_2$, —$SO_2Cl$, —$SO_2NH_2$, —$NHNH_2$, —$NHSO_2CH_3$, —$N_3$, —$NR^{1A}R^{1B}$, —$OR^{1A}$, —$SR^{1A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —CN, —C(O)OH, —$CONH_2$, —$NO_2$, —$SO_2Cl$, —$SO_2NH_2$, —$NHNH_2$, —$NHSO_2CH_3$, —$N_3$, —$NR^{2A}R^{2B}$, —$OR^{2A}$, —$SR^{2A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —CN, —C(O)OH, —$CONH_2$, —$NO_2$, —$SO_2Cl$, —$SO_2NH_2$, —$NHNH_2$, —$NHSO_2CH_3$, —$N_3$, —$NR^{3A}R^{3B}$, —$OR^{3A}$, —$SR^{3A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, —CN, —C(O)OH, —$CONH_2$, —$NO_2$, —$SO_2Cl$, —$SO_2NH_2$, —$NHNH_2$, —$NHSO_2CH_3$, —$N_3$, —$NR^{4A}R^{4B}$, —$OR^{4A}$, —$SR^{4A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, —CN, —C(O)OH, —$CONH_2$, —$NO_2$, —$SO_2Cl$, —$SO_2NH_2$, —$NHNH_2$, —$NHSO_2CH_3$, —$N_3$, —$NR^{5A}R^{5B}$, —$OR^{5A}$, —$SR^{5A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is hydrogen, halogen, —CN, —C(O)OH, —$CONH_2$, —$NO_2$, —$SO_2Cl$, —$SO_2NH_2$, —$NHNH_2$, —$NHSO_2CH_3$, —$N_3$, —$NR^{6A}R^{6B}$, —$OR^{6A}$, —$SR^{6A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

any two of $R^1$, $R^2$ or $R^3$ substituents or any two of $R^4$, $R^5$ or $R^6$ substituents may optionally be joined to form a substituted or unsubstituted aryl or substituted or unsubstituted heteroaryl;

any one of $R^1$, $R^2$ or $R^3$ and any one of $R^4$, $R^5$ or $R^6$ may optionally be joined to form a substituted or unsubstituted cycloalkyl, substituted or unsubstituted aryl or substituted or unsubstituted heteroaryl; and each $R^{1A}$, $R^{2A}$, $R^{3A}$, $R^{4A}$, $R^{5A}$ or $R^{6A}$, $R^{1B}$, $R^{2B}$, $R^{3B}$, $R^{4B}$, $R^{5B}$ and $R^{6B}$ is independently a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

8. The process of claim 7, wherein the recombinant KabA polypeptide and recombinant KabC polypeptide are each expressed by a recombinant microorganism.

9. The process of claim 7, wherein the recombinant KabA polypeptide and the recombinant KabC polypeptide are expressed by the same recombinant microorganism.

10. The process of claim 7, wherein the microorganism is a bacterium.

* * * * *

SEQUENCE LISTING

<160> NUMBER OF SEQ ID NOS: 36

<210> SEQ ID NO 1
<211> LENGTH: 360
<212> TYPE: PRT
<213> ORGANISM: Digenea simplex

<400> SEQUENCE: 1

```
Met Thr Val Ser Lys Tyr Asn Gly Val Ala Ser Thr Phe Asn Gly Val
1               5                   10                  15

Ala Arg Arg Phe Asp Phe Ala Pro Leu Glu Ala Asp Lys Leu Asn Trp
            20                  25                  30

Tyr Pro Arg Ser Ala Leu Pro Pro Glu Ile Pro Ala Ile Asp Leu Asn
        35                  40                  45

Lys Val Asn Thr Glu Glu Glu Leu Ala Gln Phe Leu Val Asp Ile Arg
    50                  55                  60

Lys Ser Gly Leu Phe Tyr Ile Val Asp His Gly Ile Pro Glu Glu Ile
65                  70                  75                  80

Ser Ile Gly Cys Tyr Asn Ala Phe Arg Glu Phe Cys Asn Leu Pro Glu
                85                  90                  95

Glu Ala Arg Glu Lys Tyr Asn Thr Asp Glu Ser Phe Lys Ser Gly Gly
            100                 105                 110

Tyr Val Pro Phe Lys Gly Thr Ser Ile Gly Gly Asn Leu Phe Glu
        115                 120                 125

Arg Gln Lys Asp Phe Val Val Lys Phe Phe Trp Arg Gly Pro Ser Val
    130                 135                 140

Val Asn Arg Ser Pro Asn Asp Arg Phe Ala Glu Phe His Asp Glu His
145                 150                 155                 160
```

```
His Arg Lys Thr Ala Glu Leu Ala Glu Lys Ile Ile Thr Thr Ile Leu
            165                 170                 175

Lys Ala Leu Lys Thr Arg Phe Pro Glu Phe His Pro Asp Glu Leu Lys
        180                 185                 190

Asp Asn Ile Asn Val Arg Asn Met Phe Phe Ser Asn Arg Ile Tyr Pro
    195                 200                 205

Glu Ala Pro Pro Asp Asp Gly Glu Lys Ala Asp Tyr Arg Leu Val Pro
210                 215                 220

His Arg Asp Leu Ser Phe Ile Thr Leu Ala Asn Gln Val Pro Ala Asn
225                 230                 235                 240

Asn Gly Phe Lys Gly Leu Phe Ile Leu Thr Gly Asp Gly Glu Lys Ile
                245                 250                 255

Pro Val Pro Pro Ile Arg Asn Ser Tyr Leu Val Phe Ile Gly Gln Gly
            260                 265                 270

Leu Ser Tyr Leu Thr Asn Lys Tyr Leu Pro Ala Ala Leu His Gly Val
        275                 280                 285

Asp Phe Pro Asp Asn Thr Asn Phe Glu Gly Ser Glu Arg Ala Ser Leu
    290                 295                 300

Ile Ser Phe Tyr Glu Pro Asn Asp Tyr Met Met Pro Ser Lys Asn Ile
305                 310                 315                 320

Asn Pro Leu Pro Glu Glu Ile Phe Glu Lys Ser Cys Thr Phe Tyr Asp
                325                 330                 335

Asp Val Gly Val Gly Arg Ala Gly Thr Thr Tyr Asn Tyr Val Arg Tyr
            340                 345                 350

Lys Phe His Glu Gly Tyr Tyr Leu
        355                 360

<210> SEQ ID NO 2
<211> LENGTH: 351
<212> TYPE: PRT
<213> ORGANISM: Palmaria palmata

<400> SEQUENCE: 2

Met Pro Val Tyr Asn Gly Thr Ser Gln Ala Phe Asn Phe Ala Pro Leu
1               5                   10                  15

His Pro Asp Ser Leu Asn Trp Cys Pro Lys Ser Ser Leu Pro Pro Glu
            20                  25                  30

Ile Pro Val Val Asp Leu Ser Lys Leu Asn Ser Glu Ala Glu Leu Ala
        35                  40                  45

Gln Phe Leu Val Asp Ile Arg Lys Ser Gly Leu Phe Tyr Val Val Asn
    50                  55                  60

His Gly Val Pro Glu Glu Leu Ser Ile Gly Cys Tyr Asn Arg Phe Arg
65                  70                  75                  80

Gln Phe Cys Asn Ile Pro Glu Asp Gln Arg Ala Glu Tyr Ser Thr Asp
                85                  90                  95

His His Phe Val Asn Gly Gly Tyr Met Pro Tyr Lys Ser Ser Ser Ile
            100                 105                 110

Gly Lys Ala Asn Lys Gly Lys Ser Gln Lys Asp Phe Val Val Lys Tyr
        115                 120                 125

Phe Trp Arg Gly Pro Arg Val Glu Asn Arg Ser Pro Asp Ala Asp Phe
    130                 135                 140

Lys Ser Tyr His Asp Glu Tyr His Arg Arg Thr Ala Asp Ile Ala Asn
145                 150                 155                 160

Ser Val Ile Thr Lys Ile Leu Gln Ala Leu Thr Thr Arg Phe Pro Asp
                165                 170                 175
```

```
Phe Asp Pro Ala Glu Tyr Lys Asp Asn Ile Asn Ser His His Met Phe
                180                 185                 190
Phe Ser Asn Arg Leu Tyr Pro Asp Asn Glu Pro Glu Lys Gly Glu Asn
            195                 200                 205
Val Glu Tyr Arg Leu Val Pro His Arg Asp Leu Ser Phe Val Thr Leu
210                 215                 220
Ala His Gln Ile Pro Ala Asp Asn Gly Tyr Gln Gly Leu Phe Val Phe
225                 230                 235                 240
Thr Gly Asp Gly Lys Lys Val Cys Val Pro Ile Arg Asn Ser Tyr
                245                 250                 255
Leu Val Phe Met Gly Gln Ala Met Ser Tyr Leu Thr Asn Lys Tyr Leu
                260                 265                 270
Pro Ala Gly Leu His Gly Val Asp Phe Pro Glu Lys Asn Cys Phe Glu
                275                 280                 285
Gly Ser Glu Arg Ser Ser Leu Ile Ser Phe Tyr Glu Pro His Asp His
                290                 295                 300
Met Met Pro Ser Lys Ala Leu Thr Pro Lys Asp Glu Ile Phe Asp
305                 310                 315                 320
Arg Gly Cys Ser Phe Phe Asp Asp Ile Gly Val Asp Lys Thr Gly Thr
                325                 330                 335
Thr Tyr Met Tyr Val Lys Asn Lys Phe His Glu Gly Tyr Tyr Leu
                340                 345                 350

<210> SEQ ID NO 3
<211> LENGTH: 358
<212> TYPE: PRT
<213> ORGANISM: Palmaria hecatensis

<400> SEQUENCE: 3

Met Pro Val Tyr Asn Gly Thr Pro Gln Ala Tyr Asn Gly Thr Ser Gln
1               5                   10                  15
Ala Phe Asn Phe Ala Pro Leu Asp Ala Asp Ser Leu Thr Trp Cys Pro
                20                  25                  30
Glu Ser Ser Leu Pro Pro Glu Ile Pro Ala Ile Asp Leu Ser Lys Val
            35                  40                  45
Asn Ser Lys Ser Glu Leu Ala Glu Phe Leu Val Asn Ile Arg Lys Ser
        50                  55                  60
Gly Leu Phe Tyr Val Val Asn His Gly Val Pro Glu Glu Leu Ser Met
65                  70                  75                  80
Gly Cys Tyr Asn His Phe Arg Glu Phe Cys Asn Ile Pro Glu Glu Glu
                85                  90                  95
Arg Ala Glu Tyr Ser Thr Asp His His Phe Val His Gly Gly Tyr Met
                100                 105                 110
Pro Tyr Lys Ser Ser Ser Ile Gly Lys Ala Asn Lys Gly Lys Asp Gln
                115                 120                 125
Lys Asp Phe Val Val Lys Tyr Phe Trp Arg Gly Pro Leu Val Glu Asn
130                 135                 140
Arg Ser Pro Ser Thr Gly Phe Lys Arg Tyr His Asp Glu Tyr His Arg
145                 150                 155                 160
Arg Thr Ser Asp Ile Ala Asn Ser Val Ile Ala Lys Ile Met Gln Ala
                165                 170                 175
Leu Thr Thr Arg Phe Pro Asp Phe Asp Pro Asp Glu Tyr Lys Lys Asn
                180                 185                 190
```

Ile Asn Ser His His Met Phe Phe Ser Asn Arg Leu Tyr Pro Asp Asn
            195                 200                 205

Glu Pro Glu Lys Gly Glu Asn Ala Glu Tyr Arg Leu Val Pro His Arg
    210                 215                 220

Asp Leu Ser Phe Val Thr Leu Ala His Gln Ile Pro Ala Asp Asn Gly
225                 230                 235                 240

Tyr Gln Gly Leu Phe Val Leu Thr Gly Asp Gly Lys Lys Val Cys Val
                245                 250                 255

Pro Pro Ile Arg Asn Ser Tyr Leu Val Phe Met Gly Gln Ala Met Ser
            260                 265                 270

Tyr Leu Thr Asn Lys Tyr Leu Pro Ala Gly Leu His Gly Val Asp Phe
    275                 280                 285

Pro Glu Lys Asn Cys Phe Glu Gly Ser Glu Arg Ser Ser Leu Ile Ser
    290                 295                 300

Phe Tyr Glu Pro His Asp His Met Met Pro Ser Lys Ala Leu Thr Pro
305                 310                 315                 320

Lys Asp Asp Glu Ile Phe Asp Arg Gly Cys Ser Phe Phe Asp Asp Ile
                325                 330                 335

Gly Val Asp Lys Ser Gly Thr Ala Tyr Met His Val Lys Asn Lys Phe
                340                 345                 350

His Glu Gly Tyr Tyr Leu
            355

<210> SEQ ID NO 4
<211> LENGTH: 351
<212> TYPE: PRT
<213> ORGANISM: Rhodophysema elegans

<400> SEQUENCE: 4

Met Ala Val Tyr Asn Gly Val Ser Gln Ala Phe Asp Phe Ala Pro Leu
1               5                   10                  15

Asp Ala Asp Ser Leu Asn Trp Cys Pro Gln Ser Ser Leu Pro Pro Glu
                20                  25                  30

Ile Pro Ala Ile Asp Leu Gly Lys Val Asn Thr Arg Ala Glu Leu Ala
            35                  40                  45

Gln Phe Leu Ile Asp Ile Arg Arg Ser Gly Leu Phe Tyr Val Val Asn
    50                  55                  60

His Gly Val Pro Glu Glu Leu Ser Ile Gly Cys Tyr Asn Leu Phe Arg
65                  70                  75                  80

Arg Phe Cys Asn Ile Pro Glu Glu Arg Ala Lys Tyr Ser Thr Asp
                85                  90                  95

His His Phe Val Asn Gly Gly Tyr Met Pro Tyr Lys Ser Ser Ser Ile
                100                 105                 110

Gly Lys Ala Asn Met Gly Lys Asp Gln Lys Asp Phe Val Val Lys Tyr
            115                 120                 125

Phe Trp Arg Gly Pro Arg Val Glu Asn Arg Thr Pro Thr Ala Glu Phe
    130                 135                 140

Lys Lys Tyr His Asp Glu Tyr His Arg Arg Thr Ser Gly Val Ala Asp
145                 150                 155                 160

Thr Val Ile Glu Lys Ile Met Gln Ala Leu Ala Thr Arg Phe Pro Asp
                165                 170                 175

Phe Asp Pro Asp Glu Tyr Lys Glu Asn Thr Asn Ser His His Met Phe
            180                 185                 190

-continued

```
Phe Ser Asn Arg Leu Tyr Pro Glu Asn Glu Pro Glu Lys Gly Glu Asn
            195                 200                 205

Val Glu Tyr Arg Leu Val Pro His Arg Asp Leu Ser Leu Val Thr Leu
210                 215                 220

Ala His Gln Ile Pro Ala Asp Asn Gly Tyr Gln Gly Leu Phe Val Leu
225                 230                 235                 240

Thr Gly Asp Gly Lys Lys Val Pro Val Pro Pro Ile Arg Asn Ser Tyr
                245                 250                 255

Leu Val Phe Leu Gly Gln Ala Leu Ser Tyr Leu Thr Asn Lys Tyr Leu
                260                 265                 270

Pro Ala Gly Leu His Gly Val Asp Phe Pro Glu Lys Asn Ser Phe Glu
            275                 280                 285

Gly Ser Glu Arg Ser Ser Leu Ile Ser Phe Tyr Glu Pro His Asp Arg
            290                 295                 300

Met Met Pro Ser Lys Ala Leu Thr Pro Lys Glu Asp Glu Val Phe Asp
305                 310                 315                 320

Arg Ser Cys Ser Phe Phe Asp Asp Ile Gly Val Asp Thr Ser Gly Thr
                325                 330                 335

Thr Tyr Met Tyr Val Lys Asn Lys Phe His Glu Gly Tyr Leu
                340                 345                 350

<210> SEQ ID NO 5
<211> LENGTH: 350
<212> TYPE: PRT
<213> ORGANISM: Grateloupia filicina

<400> SEQUENCE: 5

Met Thr Ser Phe Asp Phe Val Ala Lys Thr Phe Asp Phe Ala Pro Val
1               5                   10                  15

Lys Ala Asp Glu Leu Lys Trp Tyr Pro Arg Ser Ala Leu Pro Pro Glu
                20                  25                  30

Ile Pro Val Ile Asp Leu Asn Asn Val Asn Thr Glu Glu Glu Leu Ala
            35                  40                  45

Gln Phe Leu Val Asp Ile Arg Lys Ser Gly Leu Phe Tyr Val Val Asn
        50                  55                  60

His Asp Ile Pro Glu Glu Ile Ser Ile Gln Thr Tyr Asn Glu Phe Arg
65                  70                  75                  80

Glu Phe Cys Lys Leu Pro Glu Glu Ala Arg Gln Lys Tyr Asn Thr Asp
                85                  90                  95

Arg Cys Phe Phe Asn Gly Gly Tyr Val Pro Phe Lys Ala Thr Ser Ile
            100                 105                 110

Asn Gly Gly Asn Lys Asn Lys Gln Gln Arg Asp Phe Val Lys Phe
        115                 120                 125

Phe Trp Arg Gly Pro His Val Val Asn Arg Ser Pro Asn Glu Arg Phe
130                 135                 140

Ala Lys Trp His His Gln Tyr His Thr Arg Thr Ala Glu Leu Gly Glu
145                 150                 155                 160

Lys Val Met Thr Thr Ile Ala Lys Ala Leu Lys Thr Arg Phe Pro Asp
                165                 170                 175

Phe Asp Pro Ala Glu Leu Glu Asp Asn Val Asn Pro His Asn Met Ile
            180                 185                 190

Phe Ser Asn Arg Ile Tyr Pro Glu Phe Pro Pro Ser Glu Gly Glu Asp
        195                 200                 205
```

```
Ala Glu Tyr Arg Leu Thr Pro His Arg Asp Ile Ser Tyr Ile Thr Leu
    210                 215                 220

Val Asn Gln Thr Pro Ala Asn Asn Gly Phe Lys Ala Leu Phe Ile Val
225                 230                 235                 240

Thr Gly Asp Gly Glu Arg Val Tyr Val Pro Pro Ile Arg Asn Ser Tyr
                245                 250                 255

Leu Val Phe Ile Gly Gln Ser Leu Ser Tyr Leu Thr Asn Lys Tyr Leu
            260                 265                 270

Pro Ala Ala Leu His Gly Val Ala Phe Pro Asp Gly Asn Leu Glu Gly
        275                 280                 285

Cys Glu Arg Ala Ser Leu Val Ser Phe Tyr Glu Pro Tyr Asp Arg Met
290                 295                 300

Val Pro Ser Lys Asn Ile Lys Pro Thr Ala Glu Glu Ile Ala Pro Lys
305                 310                 315                 320

Ser Cys Ser Phe Tyr Asp Ser Ile Gly Cys Asp Lys Thr Gly Thr Thr
                325                 330                 335

Phe Thr Asp Val Arg Ala Lys Phe His Ser Gly Tyr Tyr Val
                340                 345                 350
```

<210> SEQ ID NO 6
<211> LENGTH: 1083
<212> TYPE: DNA
<213> ORGANISM: Digenea simplex

<400> SEQUENCE: 6

```
atgacagtaa gtaagtacaa cggtgttgcg agtacgttca acggtgttgc aaggagattc      60
gactttgccc cattggaggc agataaattg aattggtatc ccaggtcagc tcttcctcca     120
gaaatccctg ctatcgacct gaataaggtc aatactgaag aagaactggc tcaattcctg     180
gtcgatattc gcaaatctgg gctctttat attgttgatc atggcattcc agaggagatc     240
tctataggat gttacaatgc attccgtgag ttttgcaacc ttcccgagga agcaagagag     300
aagtacaaca cagatgagtc ctttaaaagc ggtggctatg ttcctttcaa aggcacgtcg     360
attggtggag ggaacttgtt tgaacgacag aaggatttcg ttgtcaaatt cttttggaga     420
ggaccaagtg ttgtcaatag gtctcctaat gatcgctttg ccgaattcca tgatgaacat     480
catcgaaaga cagctgagtt ggccgaaaaa atcatcacta ccattttgaa agccctgaag     540
acacgctttc agaattcca tcctgacgag ctaaaggata tatcaatgt tcgaaacatg     600
tttttcagta atcgaatcta tccagaggct ccgccagatg atggagaaaa agctgactac     660
cgacttgttc ctcatcgaga tctcagtttt atcactcttg caaatcaagt tccggctaac     720
aatggattca agggtctttt tatactgaca ggtgatggag aaaaaattcc tgttcctcca     780
atccggaaca gctacttggt cttcatcggt caaggcctct catatctcac gaataagtat     840
cttcctgcag cgcttcatgg tgtggacttt ccagacaata caaatttga aggaagtgaa     900
agagcctctc tgatcagctt ctacgagcca acgattaca tgatgccatc caagaacatt     960
aaccctttac ctgaggagat atttgagaaa agctgtacgt tttacgatga tgtcggagta    1020
gggagggctg gtacaacata taattacgtg aggtacaaat ttcatgaagg atactacctt    1080
taa                                                                 1083
```

<210> SEQ ID NO 7
<211> LENGTH: 1056
<212> TYPE: DNA
<213> ORGANISM: Rhodophysema elegans

<400> SEQUENCE: 7

```
atggcggtgt acaatggcgt ctcgcaggcc ttcgacttcg cgccgctcga cgccgacagc    60
ctcaactggt gccccagtc gtccctgccg cccgagatcc ccgccatcga cctcggcaaa    120
gtgaacacca gggccgagct cgcccagttc ctgatcgaca tccgcaggtc cggcctcttc    180
tacgtcgtca accacggcgt gccggaagag ctctcgatcg gctgctacaa cctctttcgc    240
cgcttctgca catccccga ggaggagcgc gccaagtaca gcaccgacca tcatttcgtc    300
aacggcggct acatgccata caagagctcc tccatcggca aggcgaacat gggcaaggac    360
cagaaggact ttgtcgtcaa gtacttctgg aggggggccc cgcgtggagaa caggacgccc    420
accgccgagt ttaagaagta tcacgatgag taccatcgca ggacttcggg cgtcgcagac    480
acggtcatag agaagattat gcaggcgctg gcgacgcgct ttccggactt cgaccccgac    540
gagtacaagg agaacacgaa cagccatcac atgttttca gcaacaggct ctaccccgaa    600
aacgagccgg agaagggga gaacgtcgag taccgccttg ttccgcatcg cgacctcagt    660
ttggtgacgc tcgcgcacca gatccccgca gacaatggct accagggcct gttcgttctt    720
accggcgacg ggaagaaggt gcctgtgccg cctatccgca acagctatct cgtcttcctg    780
gggcaggcgt tgtcttatct caccaacaag tatctgcctg ctggattgca tggcgtggac    840
tttccggaga gaactccttt tgaggggagc gagcggtcgt cacttatttc attctacgag    900
ccgcacgacc gcatgatgcc gtcgaaggcg ctcacgccaa aagaggatga agtttttgat    960
agaagctgct ccttttttcga tgatattggt gttgatacga gtggcacgac gtatatgtac    1020
gtgaaaaata agttccacga gggctattat ctatag                             1056
```

<210> SEQ ID NO 8
<211> LENGTH: 1056
<212> TYPE: DNA
<213> ORGANISM: Palmaria hecatensis

<400> SEQUENCE: 8

```
atggcggtgt acaatggcgt ctcgcaggcc ttcgacttcg cgccgctcga cgccgacagc    60
ctcaactggt gccccagtc gtccctgccg cccgagatcc ccgccatcga cctcggcaaa    120
gtgaacacca gggccgagct cgcccagttc ctgatcgaca tccgcaggtc cggcctcttc    180
tacgtcgtca accacggcgt gccggaagag ctctcgatcg gctgctacaa cctctttcgc    240
cgcttctgca catccccga ggaggagcgc gccaagtaca gcaccgacca tcatttcgtc    300
aacggcggct acatgccata caagagctcc tccatcggca aggcgaacat gggcaaggac    360
cagaaggact ttgtcgtcaa gtacttctgg aggggggccc cgcgtggagaa caggacgccc    420
accgccgagt ttaagaagta tcacgatgag taccatcgca ggacttcggg cgtcgcagac    480
acggtcatag agaagattat gcaggcgctg gcgacgcgct ttccggactt cgaccccgac    540
gagtacaagg agaacacgaa cagccatcac atgttttca gcaacaggct ctaccccgaa    600
aacgagccgg agaagggga gaacgtcgag taccgccttg ttccgcatcg cgacctcagt    660
ttggtgacgc tcgcgcacca gatccccgca gacaatggct accagggcct gttcgttctt    720
accggcgacg ggaagaaggt gcctgtgccg cctatccgca acagctatct cgtcttcctg    780
gggcaggcgt tgtcttatct caccaacaag tatctgcctg ctggattgca tggcgtggac    840
tttccggaga gaactccttt tgaggggagc gagcggtcgt cacttatttc attctacgag    900
ccgcacgacc gcatgatgcc gtcgaaggcg ctcacgccaa aagaggatga agtttttgat    960
```

| | |
|---|---:|
| agaagctgct cctttttcga tgatattggt gttgatacga gtggcacgac gtatatgtac | 1020 |
| gtgaaaaata agttccacga gggctattat ctatag | 1056 |

<210> SEQ ID NO 9
<211> LENGTH: 1056
<212> TYPE: DNA
<213> ORGANISM: Palmaria palmata

<400> SEQUENCE: 9

| | |
|---|---:|
| atgcccgtgt acaacggcac ctcccaggcc ttcaacttcg cgcccctcca ccccgacagc | 60 |
| ctcaactggt gccccaagtc gtccctgccc ccgagatcc ccgtagtcga ccttagcaaa | 120 |
| ctcaactctg aggccgagct cgcccagttt ctggtcgaca tccgcaagtc cggcctcttc | 180 |
| tacgttgtca accacggcgt gccggaggag ctctccatcg gctgctacaa ccgcttccgc | 240 |
| cagttttgca acatccccga ggaccagcgc gccgagtaca gcaccgacca ccattttgta | 300 |
| aacggcggct acatgcccta caaaagcagt tccattggca aggcgaacaa gggcaagagt | 360 |
| cagaaggact ttgtcgtcaa gtacttctgg aggggggccc gtgttgagaa caggtcgccc | 420 |
| gacgccgact tcaagagcta tcacgacgag taccaccgga ggaccgccga catcgcgaac | 480 |
| agcgtcatca ccaaaatcct gcaggcgttg acaacccgct cccagactt tgaccccgct | 540 |
| gagtacaagg acaacataaa cagccaccac atgtttttca gcaatcgcct gtatcccgac | 600 |
| aacgagccgg agaaggaga gaacgtggag taccgcctgg ttccgcatcg agatctcagt | 660 |
| ttcgtcaccc tcgcccacca gatccccgca gacaacggct accagggcct gttcgttttc | 720 |
| accggcgacg ggaagaaggt ctgtgtgccg cccatccgca acagctacct cgtcttcatg | 780 |
| gggcaggcga tgtcctatct caccaacaag tacctgcctg ccggcctgca tggtgtcgac | 840 |
| tttccggaga gaactgtttt tgagggcagc gagcggtcgt cccttatttc gttttacgag | 900 |
| ccgcacgacc acatgatgcc ttcgaaggcg ctgaccccga agatgatga aattttttgat | 960 |
| agaggctgct cctttttcga tgatattggt gtcgataaga ctggcacgac ttatatgtac | 1020 |
| gtcaaaaata agttccacga gggatattat ctatag | 1056 |

<210> SEQ ID NO 10
<211> LENGTH: 1053
<212> TYPE: DNA
<213> ORGANISM: Grateloupia filicina

<400> SEQUENCE: 10

| | |
|---|---:|
| atgacttcgt ttgatttcgt tgcgaagacc tttgactttg ctcccgtgaa agcagatgaa | 60 |
| ctgaaatggt accccaggtc tgctctccct ccagaaatcc ctgtcatcga tctgaacaac | 120 |
| gtcaacactg aagaagagct ggctcaattc ttggttgata ttcgcaaatc tggactcttc | 180 |
| tatgtggtca accatgacat tccagaagag atatccatcc aaacttacaa cgaatttcgt | 240 |
| gagttttgca agctccctga ggaggccaga cagaagtata acactgatag atgcttcttt | 300 |
| aatggcggtt acgttccttt caaagccact tcaattaatg gaggcaacaa gaacaaacag | 360 |
| cagagagatt ttgtcgtaaa attcttctgg agagggccgc atgtcgtcaa caggagtccg | 420 |
| aacgagcgct tcgcaaaatg gcaccaccaa tatcacacaa gaactgctga actaggtgaa | 480 |
| aaggtcatga ctaccatcgc gaaagctttg aagacacgct ttccggattt tgaccctgct | 540 |
| gagttggaag acaacgtcaa cccgcacaac atgattttca gtaatcgaat ctacccagag | 600 |
| tttccaccca gcgaaggaga ggatgccgaa taccgactta ctcctcatag ggatatcagt | 660 |
| tatatcaccc tcgtgaatca aactccggca aacaatggct ttaaggctct tttcatagta | 720 |

```
actggtgatg gggagagagt ctatgttcct cccatccgca acagttactt ggtattcatt       780
ggacagagcc tttcatatct caccaacaag tatcttcctg ccgccctgca tggggtggcc       840
tttccagacg gaaatttaga aggatgtgag agggcatctt tggtttcctt ctacgagcct       900
tacgatcgta tggtgccttc aaaaaacatc aagcccacag cagaggagat tgctccgaaa       960
agctgttcat tttacgattc tatcggatgt gataagactg gcacgacatt tacggacgtg      1020
agggcgaaat ttcattccgg atactatgtt tga                                   1053

<210> SEQ ID NO 11
<211> LENGTH: 439
<212> TYPE: PRT
<213> ORGANISM: Digenea simplex

<400> SEQUENCE: 11
```

Met Ser Ile Thr Thr Met Lys Gly Val Thr Ser Glu Ser Pro Ala Glu
1               5                   10                  15

Ala Leu Ser Arg Phe Gln Thr Thr Gly Leu Thr Leu Asn Asn Pro Lys
            20                  25                  30

Asp Leu Tyr Trp Met Thr Glu Phe Leu Lys Glu Glu Phe Tyr Asp Lys
        35                  40                  45

Gly Asn Tyr Tyr Tyr Pro Ile Lys Thr Val Cys Asp Gly Glu Leu Ile
    50                  55                  60

Glu Thr Glu Leu Phe Cys Pro Phe Glu Pro Lys Leu Ser Pro His Tyr
65                  70                  75                  80

Ile Gln Leu Tyr Asn Ser Arg Asp Glu Arg Ser Asn Leu Tyr Ala Val
                85                  90                  95

Pro Pro Lys Lys Thr Asp Met Lys Lys Tyr Asn Arg Ile Asn Cys Glu
            100                 105                 110

Lys Met Gly Ser Leu Met Ala Pro Asn Ser Asn Tyr Asp Asp Thr Glu
        115                 120                 125

Met Val Ser Leu Phe Tyr Ser Met Met Tyr Tyr Leu Asn Asp Gln Thr
    130                 135                 140

Ala His Leu Lys Leu Pro Glu Glu Asp Ile Gln Pro Glu Leu Val Asp
145                 150                 155                 160

Glu Leu Asn Asp His Val Leu Gln Tyr Leu Ser Val Phe Leu Ser Ile
                165                 170                 175

Phe Lys Pro Arg Glu Pro Gln Asp Leu Glu Arg Ile Trp Asn Phe Leu
            180                 185                 190

Asp Phe Tyr Gln Pro Tyr Phe Lys Lys Val Asp Gly Lys Ile Ile Leu
        195                 200                 205

His Glu Lys Tyr Gln Gly Arg Thr Pro Pro Gln Ile Gly Leu Ile Lys
    210                 215                 220

Lys Ile Thr Gly Tyr Val Leu Glu Arg Phe Ala Pro Lys Lys Asn Ile
225                 230                 235                 240

Thr Gln Val Ile Tyr Glu Val Ile Arg Tyr Ile Lys Gly Ile Lys Gln
                245                 250                 255

Glu Ile Lys Ile Arg Gly Asp Lys Ser Phe Thr Leu Ser Leu Lys Glu
            260                 265                 270

Tyr Asp Glu Phe Arg Asp Gln Val Thr Ser Ser Pro Met Ala His Ser
        275                 280                 285

Ile Thr Asp Leu Thr Tyr Asp Asp Phe Ser Tyr Lys Ala Tyr Met Asn
    290                 295                 300

```
Pro Leu Phe Ile Lys Leu Glu Asp Leu Thr Ser Glu Ile Ile Thr Tyr
305                 310                 315                 320

Phe Asn Asp Val Cys Thr Cys Asp Arg Glu Arg Leu Asp Asp Pro
            325                 330                 335

Phe Asn Ser Val Phe Ile Leu Arg Asp Leu His Ser Leu Asn Tyr Val
            340                 345                 350

Lys Ser Cys Asp Leu Val Val Lys His Ala His Asp Lys Leu Ser Lys
            355                 360                 365

Phe Leu Glu Ile Lys Gln Thr Leu Leu Lys Glu Ser Thr Asn Glu Asn
370                 375                 380

Glu Lys Lys Ala Ile Ala Gln Met Ile Lys Thr Arg Glu Asp Ser Leu
385                 390                 395                 400

Ile Gly Tyr Thr Ile His Glu Ile Cys Cys Val Thr Asn Gly Tyr Ala
            405                 410                 415

Arg Asp His Lys Pro Leu Met Lys Asp Tyr Leu Glu Lys Asn Ile Phe
            420                 425                 430

Lys Lys Leu Lys Ala Thr Asn
            435
```

<210> SEQ ID NO 12
<211> LENGTH: 488
<212> TYPE: PRT
<213> ORGANISM: Palmaria palmata
<400> SEQUENCE: 12

```
Met Leu Pro Pro Ala Phe Leu Pro Pro Ala Val His Ser Leu Phe Arg
1               5                   10                  15

Gly Gly Leu Leu Gln Arg Pro Glu His Val Gly Pro Thr Pro Thr Ala
            20                  25                  30

Thr Pro Ser Ala Ala Ser Ile Arg Ala His Arg Ala Pro Thr Thr Leu
            35                  40                  45

Val Met Val Ala His Gly Arg Arg Leu Glu Arg Pro Thr Ala Ala
    50                  55                  60

Leu Pro Thr Gly Ala Arg Arg Thr Gly Leu Thr Leu Thr Asp Pro Ala
65                  70                  75                  80

Asp Leu His Ser Met Val Ala His Leu Lys Lys Glu Asn Phe Asp Lys
                85                  90                  95

Gly Asn Cys Asn Tyr Pro Ile Lys Thr Val Cys Asp Gly Glu Leu Ile
            100                 105                 110

Asp Val Gln Phe Ala Phe Pro Phe Glu Pro Lys Leu Ser Pro His Tyr
            115                 120                 125

Ala Ala Leu Tyr Asn Ser Arg Asp Glu Arg Ser Gln Leu Tyr Ala Val
130                 135                 140

Pro Pro Ser Thr Thr Asp Met Lys Lys Tyr Asn Arg Ile Asn Cys Glu
145                 150                 155                 160

Lys Met Gly Ala Leu Leu Ala Pro Asn Ser Ala Tyr Gly Asp Thr Glu
                165                 170                 175

Ile Val Ser Leu Phe Tyr Ser Met Met Tyr Tyr Leu Asn Asp Gln Thr
            180                 185                 190

Ala His Phe Lys Leu Pro Glu Glu Glu Ile Gln Tyr Glu Leu Val Asp
            195                 200                 205

Glu Leu Asn Asp Asn Val Leu Gln Tyr Leu Ser Ile Phe Leu Gly Val
210                 215                 220
```

Phe Lys Pro Arg Asp Ala Ala Asp Leu Glu Arg Ile Trp Asp Phe Leu
225                 230                 235                 240

Glu Phe Tyr Gln Pro Tyr Phe His Lys Val Asp Gly Arg Ile Glu Leu
            245                 250                 255

Asp Ala Lys Tyr Ser Gly Gln Thr Pro Pro Gln Val Ala Leu Val Ser
            260                 265                 270

Lys Ile Ala Gly Tyr Ala Ala Asp Arg Phe Gly Ala Ser Lys Asn Ile
            275                 280                 285

Thr Gln Ile Ile Tyr Glu Val Ile Arg Tyr Val Lys Gly Ile Lys Glu
        290                 295                 300

Glu Ile Lys Ile Arg Cys Asp Lys Gly Phe Ser Leu Thr Leu Ser Glu
305                 310                 315                 320

Tyr Asp Ala Phe Arg Asp Asn Val Thr Ser Ser Pro Met Ala His Ser
                325                 330                 335

Val Thr Asp Leu Thr His Asp Ala Phe Ser Tyr Glu Ala Tyr Thr Asn
            340                 345                 350

Pro Val Phe Asn Glu Leu Glu Asn Leu Thr Ser Gln Val Ile Thr Tyr
            355                 360                 365

Val Asn Asp Val Cys Thr Cys Asp Arg Glu Arg Leu Asp Asp Pro
370                 375                 380

Phe Asn Ser Val Phe Ile Leu Lys Asn Arg Asp Gly Leu Asn Phe Ala
385                 390                 395                 400

Glu Ala Cys Asp Arg Val Val Gly Glu Val Val Lys Lys Thr Ala Arg
                405                 410                 415

Phe Leu Glu Thr Lys Glu Arg Leu Leu Ala Glu Ala Ala Asp Glu Asp
            420                 425                 430

Gly Arg Ala Ala Met Ala Gln Met Ile Lys Thr Arg Glu Asp Ser Ile
        435                 440                 445

Ile Gly Tyr Met Leu His Glu Val Cys Cys Val Thr Asp Gly Tyr Ala
            450                 455                 460

Arg Asp His Lys Pro Leu Met Lys Asp Tyr Leu Glu Lys Thr Met Phe
465                 470                 475                 480

Gly Glu Val Ala Ser Gly Ala Met
                485

<210> SEQ ID NO 13
<211> LENGTH: 485
<212> TYPE: PRT
<213> ORGANISM: Palmaria hecatensis

<400> SEQUENCE: 13

Met Pro Pro Pro Ala Phe Leu Pro Pro Ala Val Arg Ser Leu Phe Arg
1               5                   10                  15

Gly Ala Pro Leu Gln Arg Leu Gln His Val Gly Pro Ile Gln Ser Ala
            20                  25                  30

Thr Pro Ser Ala Ala Ser Ile Arg Ala Arg Arg Ala Ala Arg Thr Leu
        35                  40                  45

Val Met Val Asp Ala Gly Pro Glu Arg Pro Thr Ala Ala Pro Pro Thr
    50                  55                  60

Gly Ala Arg Arg Thr Asp Leu Thr Leu Thr Asp Pro Ala Asp Leu Ala
65                  70                  75                  80

Leu Met Val Ala His Leu Lys Arg Glu His Phe Asp Lys Gly Tyr Cys
                85                  90                  95

```
Thr Tyr Pro Ile Lys Thr Val Cys Asp Gly Glu Leu Ile Asp Val Gln
            100                 105                 110

Phe Ser Phe Pro Phe Glu Pro Lys Leu Ser Pro His Tyr Ala Ala Leu
            115                 120                 125

Tyr Asn Ser Arg Asp Glu Arg Ser Gln Leu Tyr Ala Val Ser Pro Asn
            130                 135                 140

Thr Thr Asp Met Lys Lys Tyr Asn Arg Ile Asn Cys Glu Lys Met Gly
145                 150                 155                 160

Ala Leu Leu Ala Pro Asn Ser Ala Tyr Gly Asp Thr Glu Met Val Ser
                165                 170                 175

Leu Phe Tyr Ser Met Met Tyr Tyr Leu Asn Asp Gln Thr Ala His Phe
            180                 185                 190

Lys Leu Pro Glu Glu Ile Gln Tyr Glu Leu Val Asp Glu Leu Asn
            195                 200                 205

Asp Asn Val Leu Gln Tyr Leu Ser Ile Phe Leu Gly Val Phe Glu Pro
            210                 215                 220

Arg Asp Ala Ala Asp Leu Glu Arg Ile Trp Asp Phe Leu Glu Phe Tyr
225                 230                 235                 240

Gln Pro Tyr Phe Asn Lys Val Gly Gly Lys Ile Val Leu Asp Ala Lys
                245                 250                 255

Tyr Ser Gly Gln Thr Pro Pro Gln Val Ala Leu Val Thr Lys Ile Ala
            260                 265                 270

Gly Tyr Ala Ala Gly Arg Phe Gly Ala Thr Lys Asn Ile Thr Gln Ile
            275                 280                 285

Ile Tyr Glu Val Ile Arg Tyr Val Lys Gly Ile Lys Gln Glu Ile Lys
            290                 295                 300

Ile Arg Cys Asp Lys Ser Phe Thr Leu Asn Leu Ala Glu Tyr Asp Ala
305                 310                 315                 320

Phe Arg Asp Gln Val Thr Ser Ser Pro Met Ala His Ser Val Thr Asp
                325                 330                 335

Leu Thr His Asp Ala Phe Ser Tyr Lys Ala Tyr Thr Asn Pro Val Phe
            340                 345                 350

Asn Asp Leu Glu Asn Leu Thr Ser Gln Ile Ile Thr Tyr Val Asn Asp
            355                 360                 365

Val Cys Thr Cys Asp Arg Glu Arg Leu Asp Asp Pro Phe Asn Ser
370                 375                 380

Val Phe Ile Leu Lys Asn Arg Asp Gly Leu Asn Phe Ala Asp Ala Cys
385                 390                 395                 400

Asp Leu Val Val Gly Glu Val Val Lys Lys Thr Ala Lys Phe Leu Glu
                405                 410                 415

Thr Lys Asp Arg Leu Leu Ala Glu Ala Asp Glu Glu Gly Arg Ala
            420                 425                 430

Ala Ile Ala Gln Lys Ile Lys Thr Arg Glu Asp Ser Ile Ile Gly Tyr
            435                 440                 445

Met Met His Glu Val Cys Cys Val Thr Asp Gly Tyr Ala Arg Asp His
            450                 455                 460

Lys Pro Leu Met Lys Glu Tyr Leu Glu Lys Ala Met Phe Gly Glu Ala
465                 470                 475                 480

Ser Ser Gly Ala Leu
            485

<210> SEQ ID NO 14
<211> LENGTH: 479
```

```
<212> TYPE: PRT
<213> ORGANISM: Rhodophysema elegans

<400> SEQUENCE: 14
```

| | | | | | | | | | | | | | | |
|---|---|---|---|---|---|---|---|---|---|---|---|---|---|---|

Met Ser Pro Ser Ala Phe Leu Pro Leu Ala Gly Pro Leu Ala Phe Arg
1               5                   10                  15

Arg Ala Ser Leu Gln Arg Leu Asn His Thr Arg Thr Leu Pro Pro Thr
            20                  25                  30

Val Ala Pro Ser Arg Ala Pro Met Thr Pro Phe Met Val Asp Thr Ser
            35                  40                  45

Arg Gly His Pro Ala Thr Ala Ala Pro Pro Met Gly Ala Arg Arg Ser
            50                  55                  60

Leu Thr Leu Thr Asp Pro Ala Asp Leu Ala Leu Met Val Ser His Leu
65                      70                  75                  80

Lys Arg Glu His Phe Asp Lys Gly Asp Tyr Leu Tyr Pro Ile Lys Thr
                85                  90                  95

Val Cys Ala Gly Glu Asp Ile Asp Val Arg Phe Ala Ile Pro Phe Glu
            100                 105                 110

Pro Arg Leu Ser Ser His Tyr Ala Ala Leu Tyr Asn Ser Arg Asn Asp
            115                 120                 125

Arg Ala Lys Leu Tyr Ala Val Pro Pro Arg Thr Thr Asp Met Arg Lys
130                 135                 140

Tyr Asn Arg Ile Asn Cys Glu Lys Met Gly Ala Leu Leu Ala Pro Asn
145                 150                 155                 160

Ser Ala Tyr Gly Asp Thr Glu Ala Val Ser Leu Phe Tyr Ser Met Met
                165                 170                 175

Tyr Tyr Leu Asn Asp Gln Thr Ala Ile Cys Lys Leu Pro Glu Asp Glu
            180                 185                 190

Ile Glu Leu Arg Leu Val Asp Glu Leu Asn Asp Asn Val Leu Gln Tyr
            195                 200                 205

Leu Gly Ile Phe Leu Ser Val Phe Glu Pro Arg Asp Ala Ala Asp Leu
210                 215                 220

Glu Arg Ile Trp Asp Phe Leu Asp Phe Tyr Gln Pro Tyr Phe Arg Lys
225                 230                 235                 240

Ala Gly Arg Arg Ile Val Leu Asp Asp Lys Tyr Leu Gly Gln Thr Pro
                245                 250                 255

Pro Gln Val Ala Leu Val Thr Thr Ile Ala Asn Tyr Val Ala Glu Arg
            260                 265                 270

Phe Gly Ala Thr Lys Asn Ile Thr Gln Val Val Tyr Glu Val Ile Arg
            275                 280                 285

Tyr Val Lys Gly Ile Lys Gln Glu Val Lys Ile Arg Cys Asp Lys Gly
290                 295                 300

Phe Thr Leu Ser Leu Ala Glu Tyr Asp Asp Phe Arg Asp Gln Val Thr
305                 310                 315                 320

Ser Ser Pro Met Ala His Ser Val Thr Asp Leu Thr His Asp Ala Phe
                325                 330                 335

Ser Tyr Glu Ala Tyr Lys Asn Pro Val Phe Asn Ser Leu Glu Asn Leu
            340                 345                 350

Thr Ser Gln Val Ile Thr Tyr Ile Asn Asp Val Cys Thr Cys Asp Arg
            355                 360                 365

Glu Arg Leu Asp Lys Asp Pro Phe Asn Ser Val Phe Ile Leu Lys Asp
            370                 375                 380

Arg Asp Gly Leu Asn Phe Ala Asp Ala Cys Asp Leu Val Val Ala Glu
385                 390                 395                 400

```
Ile Glu Lys Lys Met Ala Lys Phe Leu Glu Thr Lys Lys Gln Leu Leu
            405                 410                 415

Ser Glu Ala Ala Asp Glu Arg Arg Thr Ala Met Ala Gln Met Ile
        420                 425                 430

Lys Thr Arg Glu Asp Ser Ile Ile Gly Tyr Met Met His Glu Val Cys
        435                 440                 445

Cys Val Thr Asp Gly Tyr Ala Arg Asp His Lys Pro Lys Met Lys Glu
        450                 455                 460

Tyr Leu Glu Lys Ala Met Phe Gly Glu Val Ser Arg Glu Ala Met
465                 470                 475
```

<210> SEQ ID NO 15
<211> LENGTH: 452
<212> TYPE: PRT
<213> ORGANISM: Grateloupia filicina

<400> SEQUENCE: 15

```
Met Asn Leu Ile Leu Arg Ser Asn Met Pro Ile Phe Pro Ser Cys Ala
1               5                   10                  15

Phe Leu Ser Ser Ser Thr Thr Thr Phe Ile Gln Pro Leu Val Lys
            20                  25                  30

Arg Ile His Ser Val Cys Pro Asn Pro Val Arg His Glu Pro Val Ser
            35                  40                  45

Ala Asn Arg Arg Leu Val Met Arg Leu Ala Trp Asn Pro Thr Pro Thr
        50                  55                  60

Gln Gln Leu Thr Thr Glu Ser Pro Thr Glu Ala Leu Ser Arg Leu Gln
65                  70                  75                  80

Thr Thr Gly Leu Thr Leu Thr Asp Pro Lys Asp Leu Tyr Trp Met Thr
                85                  90                  95

Asp Phe Leu Glu Gln Gln Phe Tyr Ser Lys Arg Asn Pro Asn Tyr Pro
            100                 105                 110

Met Lys Thr Ile Cys Asp Gly Glu Leu Ile Glu Thr Glu Phe His Cys
        115                 120                 125

Pro Tyr Gln Pro Lys Leu Ser Pro His Tyr Met Arg Leu Cys Asn Thr
    130                 135                 140

Lys His Glu Arg Ser Leu Leu Tyr Ser Ile Pro Pro Asn Thr Thr Asp
145                 150                 155                 160

Met Asn Lys Tyr Asn Arg Ile Asn Cys Glu Lys Phe Ala Ser Leu Val
                165                 170                 175

Ala Pro Asn Ser Asn Tyr Glu Asp Thr Glu Ala Val Ala Leu Met Tyr
            180                 185                 190

Ser Met Met Tyr Tyr Leu Asn Asp Gln Thr Ala His Leu Lys Leu Pro
        195                 200                 205

Glu Asp Met Ile Gln Pro Gln Leu Ile Asp Glu Leu Asn Asp Asn Val
    210                 215                 220

Leu Gln Tyr Leu Ala Val Phe Leu Ser Ile Phe Glu Pro Arg Asp Pro
225                 230                 235                 240

Glu Asp Leu Glu Arg Ile Trp Asp Phe Leu Asp Phe Tyr Gln Lys Tyr
                245                 250                 255

Phe Asn Lys Ile Asp Gly Lys Ile Val Leu Asp Glu Lys Tyr Lys Gly
            260                 265                 270

Pro Val Pro Pro Gln Ile Ala Leu Ile Asn Lys Ile Thr Gln Tyr Ile
        275                 280                 285
```

```
Ser Lys Arg Phe Ala Pro Thr Lys Asn Ile Thr Gln Phe Ile Tyr Glu
    290                 295                 300

Val Ile Arg Tyr Ile Lys Gly Ile Lys Gln Glu Val Tyr Ile Arg Cys
305                 310                 315                 320

Asp Lys Ser Phe Thr Leu Ser Leu Lys Glu Tyr Asp Glu Phe Arg Asp
                325                 330                 335

Gln Val Thr Ser Ser Pro Met Ala His Ala Val Thr Asp Met Thr Tyr
            340                 345                 350

Asp Asn Phe Ser Tyr Lys Leu Tyr Leu Asn Pro Leu Phe Thr Glu Leu
        355                 360                 365

Glu Asn Leu Thr Ser Glu Leu Ile Thr Tyr Phe Asn Asp Val Cys Thr
    370                 375                 380

Cys Asp Arg Glu Arg Leu Asp Asn Asp Pro Phe Asn Ser Val Phe Ile
385                 390                 395                 400

Leu Lys Asp Leu Tyr Gly Gly Thr Tyr Ala Gln Ser Cys Asp Leu Val
                405                 410                 415

Val Ser Glu Thr Arg Lys Lys Phe Ser Lys Phe Leu Glu Ile Lys Gln
            420                 425                 430

Ile Leu Leu Asp Gly Ala Ala Asp Glu Thr Glu Lys Gln Ala Ile Ala
        435                 440                 445

Gln Met Ile Lys
    450

<210> SEQ ID NO 16
<211> LENGTH: 1320
<212> TYPE: DNA
<213> ORGANISM: Digenea simplex

<400> SEQUENCE: 16
atgagtatta ccactatgaa aggagttaca tcagagagtc ctgccgaagc gctttcccgc      60
ttccaaacta ctggattgac gttgaacaac cccaaggacc tttactggat gacagaattt     120
ttgaaggaag aattttacga caagggaaac tattattatc ccatcaaaac ggtatgtgat     180
ggcgaactca tcgaaaccga gctcttctgt cccttcgaac caaagctcag tccacattac     240
attcaattat caactctcg tgatgagcga tccaacttgt acgccgttcc gcccaagaaa      300
acagacatga aaaagtacaa tcgtataaat tgtgagaaaa tgggttcttt gatgcccct      360
aattccaatt atgacgacac agaaatggtt tctctcttct actccatgat gtactacctc     420
aatgatcaga ccgctcatct taagctccct gaagaagata ttcaacctga gcttgttgat     480
gaactcaacg accatgtctt acagtatcta agtgtgttcc ttagcatctt taaaccgcgt     540
gaacctcaag atttggagcg aatctggaat ttttttggact tttaccagcc atatttcaag     600
aaagttgatg gcaagattat cttgcacgag aaatatcagg ggcgtactcc accacaaatc     660
ggtttgatca agaaaataac aggttatgta ttagagaggt ttgctccgaa aagaatatc     720
actcaagtca tctacgaggt catcagatat atcaaggaa tcaagcaaga aattaagatt     780
cgaggtgata agagcttcac tctgtctctc aaagagtatg atgagttccg tgaccaagtt     840
acgtccagcc caatggctca ttcgattaca gatcttactt atgacgactt ctcttacaag     900
gcatacatga acccactctt catcaagctg gaagatctaa cctctgagat catcacgtac     960
ttcaacgacg tttgcacatg tgatcgcgag agactggacg atgatccttt caactctgtt    1020
ttcattctga gagatcttca cagtctcaac tatgtgaagt catgtgatct tgtcgttaag    1080
catgcacatg acaagctatc aaaattcttg gagatcaagc agactctttt gaaagaatct    1140
```

| | |
|---|---|
| acaaacgaaa atgagaaaaa ggccattgcc cagatgatta agactcgtga agattccttg | 1200 |
| attggatata cgattcatga aatttgctgt gttacaaatg ggtatgctcg tgaccacaag | 1260 |
| cccttgatga agattatttt ggagaaaaat atctttaaga aactcaaggc gacaaattaa | 1320 |

<210> SEQ ID NO 17
<211> LENGTH: 1467
<212> TYPE: DNA
<213> ORGANISM: Palmaria palmata

<400> SEQUENCE: 17

| | |
|---|---|
| atgcttcctc ctgccttcct ccctccggcc gtgcactccc tcttccgcgg cggcctgctg | 60 |
| cagcgtccgg aacacgttgg tccaaccccca actgcaacgc cttccgccgc ttcgatccgc | 120 |
| gcacaccgcg caccaacgac gctcgtcatg gtcgcgcacg gtcggcgccg tctcgaacgc | 180 |
| cccacagcgg cactaccaac cggcgcgcga cggaccggct tgacgctcac cgacccggcc | 240 |
| gacctgcatt ccatggtggc gcacctgaaa aaggagaact tcgacaaggg caactgcaac | 300 |
| tacccaatca agacggtgtg cgatggagaa ctcatcgacg tccagttcgc cttcccgttt | 360 |
| gaaccgaagc tgagcccgca ctacgccgcc tgtacaattt cgcgtgacga gcgctcccag | 420 |
| ctgtacgctg tcccgcctag tactacagat atgaaaaaat acaaccgcat caactgcgag | 480 |
| aagatgggcg ccctgctcgc gccgaactct gcgtatggcg acacggagat agtgtcgctg | 540 |
| ttctattcga tgatgtatta tctcaatgac cagacggcgc acttcaagct accagaggaa | 600 |
| gagatccagt acgagctcgt ggacgagctc aacgacaatg tgctgcagta tctcagcata | 660 |
| tttctgggcg ttttcaagcc gcgcgatgct gcggatttgg agcgcatttg ggactttctc | 720 |
| gagttttacc agcccctattt tcacaaggtc gacgggagga ttgagttaga tgccaagtat | 780 |
| agcgggcaga cgccgccgca ggtcgcgctt gtctcgaaga ttgcggggta cgccgcggat | 840 |
| cggttcggcg cgtcaaagaa catcacccag atcatctacg aggtcattcg atatgtcaag | 900 |
| ggcatcaagg aggagatcaa gatcaggtgc gacaagggct ttagcctcac cctctccgag | 960 |
| tacgacgcgt ccgggacaa tgtcacatcg agcccgatgg cgcactccgt aaccgacctg | 1020 |
| acgcacgatg cgttctccta cgaggcctac acgaaccccg tcttcaacga gctggaaaac | 1080 |
| ctgacctccc aagtcatcac ctacgtcaac gacgtgtgta cgtgcgaccg ggagcggctg | 1140 |
| gacgacgacc cgttcaattc ggtctttatt ctgaaaaatc gcgacggtct gaacttcgcc | 1200 |
| gaagcgtgcg atcgcgttgt cggcgaggtg gtgaagaaga cggcaaggtt cctggagacg | 1260 |
| aaggagcggc ttcttgcgga ggctgctgat gaagacggga gggcggccat ggcgcagatg | 1320 |
| atcaagacgc gcgaagactc gatcatcggg tacatgctgc acgaggtctg ctgcgtgacg | 1380 |
| gatgggtatg cgcgcgacca caagccgttg atgaaagact atctggagaa gacgatgttt | 1440 |
| ggtgaggtgg ccagcggagc aatgtag | 1467 |

<210> SEQ ID NO 18
<211> LENGTH: 1458
<212> TYPE: DNA
<213> ORGANISM: Palmaria hecatensis

<400> SEQUENCE: 18

| | |
|---|---|
| atgcctcctc ccgccttcct ccctccagcc gtgcgctccc tcttccgcgg cgccccgctg | 60 |
| cagcgtctgc aacacgtcgg tccaatccaa agtgcaacgc cctccgctgc ttcgatccgc | 120 |
| gcacgccgtg cagcaaggac gctcgtcatg gtcgacgcag gcccggagcg ccccacagca | 180 |

```
gcaccaccaa ccggcgcgcg acggaccgac ttgacgctaa cggacccggc agatctggcg      240
ctcatggtcg cccatctgaa aagggagcac ttcgacaagg ggtactgcac ctacccgata      300
aagacggtgt gcgatggaga actcatcgac gtccagttct ccttcccgtt cgagccgaag      360
ctgagcccgc actacgcggc cctgtacaat tcgcgtgacg agcgctcgca gctgtacgct      420
gtctcgccaa atactacgga tatgaagaag tacaaccgca tcaactgcga gaagatgggc      480
gcgctgcttg ccccgaactc tgcatatggc gacacggaga tggtttcgct gttctactcg      540
atgatgtatt atctcaatga ccagacggcg cacttcaagc tgcccgagga ggagatccag      600
tacgagcttg tggacgagct caacgacaat gtgctgcagt atctcagcat ttttctgggc      660
gtgttcgagc cgcgcgatgc tgcggacttg gagcgtattt gggactttct cgagttttac      720
cagccgtatt ttaacaaggt cggcgggaag atcgtgctgg atgccaagta cagcgggcag      780
acgccgccgc aggtcgcgct cgtcacgaag atcgcggggt acgccgcggg gcgcttcggc      840
gcgacgaaga acatcacgca gatcatctac gaggtcattc gatatgttaa gggcatcaag      900
caggagatca agatcaggtg cgacaagagc tttacccctca acctcgcgga gtacgacgcg      960
ttccgcgacc aggtcacatc gagcccgatg gcgcactctg taaccgactt gacgcacgac     1020
gccttctcct acaaggccta cacgaacccc gtcttcaacg acctggaaaa cctgacctcc     1080
caaatcatca cctatgtcaa cgacgtatgc acttgtgacc gcgagcggct ggacgacgat     1140
ccgttcaact cggtctttat tctgaaaaat cgcgacggcc tcaacttcgc cgacgcgtgc     1200
gacctcgttg tcggcgaggt cgtaaagaag acggcgaagt tcctggagac taaggatagg     1260
cttcttgcgg aagctgctga tgaagagggg agggcggcta ttgcgcagaa gatcaagacg     1320
cgcgaggact cgatcatcgg gtacatgatg cacgaggttt gctgcgtgac ggacgggtat     1380
gcgcgcgacc acaagccgct gatgaaagag tatctggaga aggcgatgtt tggtgaggcg     1440
agcagcggag ccctgtag                                                   1458

<210> SEQ ID NO 19
<211> LENGTH: 1440
<212> TYPE: DNA
<213> ORGANISM: Rhodophysema elegans

<400> SEQUENCE: 19
atgtctcctt cggcctttct cccccctagcc gggcccttag ccttccggcg ggcctcgctg       60
cagcgtctaa atcataccccg taccctccca cccaccgtcg ctccgtcccg cgcaccaatg      120
acgcccttca tggtcgacac cagccgcggg caccctgcta cagcagcccc acctatgggc      180
gcgcgccgca gcctgacgct gacggacccg gccgatctgg cgctcatggt ctcccacctg      240
aagcgcgagc atttcgacaa gggcgactac ctttacccga tcaaaaccgt atgcgccggc      300
gaggacatcg acgtccgctt cgctatcccc ttcgagccgc gcctcagctc gcactatgcg      360
gccctgtaca actcgcgaaa cgatcgcgcc aagctttacg ccgtcccgcc gcggacgact      420
gacatgcgta agtacaaccg catcaactgt gagaagatgg gcgccctgct cgcgcccaac      480
tctgcctacg gcgacacaga ggccgtctct ctcttctact cgatgatgta ctacctcaac      540
gaccagacgg cgatcgcaa gctgcccgag gacgaaatcg agcttcgcct cgtcgacgag      600
ctcaacgaca acgtgctcca atatctcggc atcttcctct ccgtcttcga gccgcgcgat      660
gccgctgatt tggagcgtat ctgggacttt ctagactttt accagccgta cttccgcaag      720
gccgccggga ggatcgtgct ggacgacaaa tacctcgggc agacgccgcc gcaggtcgcg      780
cttgtcacaa cgatcgcaaa ctacgtcgcc gaacgcttcg gcgcgacgaa gaacatcacg      840
```

```
caggtcgtct acgaggtgat tcgctatgtt aagggcatca agcaggaggt gaagatcagg    900
tgcgacaagg gattcaccct ctcactcgcc gagtacgacg atttccgcga ccaggtcacg    960
tccagcccga tggcgcactc cgtgaccgac ctcacccacg acgccttctc ctacgaggca   1020
tataagaacc cggtcttcaa ctccctggag aacctgacct cccaggtcat tacctacatc   1080
aacgacgtgt gcacgtgtga ccgagagcgg ctagacaagg accgtttaa ctcggtgttc    1140
attctgaaag accgcgacgg tctgaacttc gccgacgcgt gcgacctcgt cgtcgccgag   1200
atcgaaaaga aaatggcaaa gttcctcgag acgaagaagc agcttctgtc ggaggctgct   1260
gatgaagagc gcagaacagc catggcgcag atgatcaaga cgcgggagga ctcgatcatc   1320
ggctacatga tgcacgaggt ctgctgcgtg acggacgggt atgcgcgcga ccacaagccg   1380
aagatgaagg agtatctgga gaaggcgatg tttggggagg tgagcaggga agccatgtag   1440
```

<210> SEQ ID NO 20
<211> LENGTH: 1356
<212> TYPE: DNA
<213> ORGANISM: Grateloupia filicina

<400> SEQUENCE: 20

```
atgaatttga tcctccgcag taacatgcct attttcccat cttgcgcttt tctctcatcc     60
tcaaccacta ccactttcat tcaacctctt gtcaaacgta tccactccgt ttgccccaat    120
ccagtacgcc atgagccagt ttcagcaaac cgtcgcctag tcatgcgact tgcctggaat    180
cctacaccca ctcaacaact taccacagag agtcctaccg aagcactttc ccgccttcaa    240
accactggac taaccctgac tgacccgaag gacctttact ggatgaccga ttttttggaa    300
caacaatttt actcaaaaag aaaccccaac tatcccatga aaaccatctg cgacggcgaa    360
ctcatcgaga ccgaatttca ctgtccatac caacccaaac tcagccctca ttatatgagg    420
ttgtgcaaca ctaagcatga agatctctc ttgtactcaa ttccaccaaa caccacagat     480
atgaacaagt acaaccgaat taattgcgag aagttcgcct ctttggtagc cccgaattcc    540
aattatgaag atacagaggc tgttgccctc atgtactcca tgatgtacta tctcaatgat    600
cagactgccc atcttaaact tcctgaggat atgattcagc tcaacttat tgatgaactc     660
aacgataacg tattgcagta tctcgctgtg tttctaagca tcttcgaacc ccgcgatccg    720
gaagatttgg agcgcatctg ggacttctta gactttatc agaagtactt caacaaaata    780
gacggaaaga ttgtcttgga tgaaaagtac aaaggaccag tcccgcctca aattgctttg    840
attaacaaaa tcacccaata tatctcgaag agatttgctc cgacgaagaa cataactcag    900
ttcatctacg aggtcatcag atacatcaag gggatcaagc aagaggtcta cattcgatgt    960
gataagagtt ttactctttc tctcaaggag tatgatgaat ttcgtgatca agtgacgtcc   1020
agcccgatgg cacatgctgt gacagatatg acctatgaca acttctctta taagctctac   1080
ctgaacccgc ttttcaccga actggagaat ctgacttcag aactgatcac ctacttcaac   1140
gacgtttgca catgtgatcg cgagagactg acaatgatc ctttcaactc tgtgttcatt    1200
ctgaaagacc tttatggtgg tacctatgca caagttgtg atcttgtcgt gagcgaaacg    1260
cgcaaaaagt tctctaaatt tttggagatc aaacaaattc ttcttgatgg ggcagcagac   1320
gaaaccgaga acaagctat tgcccagatg attaag                              1356
```

<210> SEQ ID NO 21
<211> LENGTH: 51
<212> TYPE: DNA

<213> ORGANISM: Artificial sequence
<220> FEATURE:
<223> OTHER INFORMATION: Synthetic polynucleotide

<400> SEQUENCE: 21
ggtgccgcgc ggcagccata tgagtattac cactatgaaa ggagttacat c    51

<210> SEQ ID NO 22
<211> LENGTH: 47
<212> TYPE: DNA
<213> ORGANISM: Artificial sequence
<220> FEATURE:
<223> OTHER INFORMATION: Synthetic polynucleotide

<400> SEQUENCE: 22
ggtggtggtg gtgctcgagt taatttgtcg ccttgagttt cttaaag    47

<210> SEQ ID NO 23
<211> LENGTH: 47
<212> TYPE: DNA
<213> ORGANISM: Artificial sequence
<220> FEATURE:
<223> OTHER INFORMATION: Synthetic polynucleotide

<400> SEQUENCE: 23
ggtgccgcgc ggcagccata tgacagtaag taagtacaac ggtgttg    47

<210> SEQ ID NO 24
<211> LENGTH: 47
<212> TYPE: DNA
<213> ORGANISM: Artificial sequence
<220> FEATURE:
<223> OTHER INFORMATION: Synthetic polynucleotide

<400> SEQUENCE: 24
ggtggtggtg gtgctcgagt taaaggtagt atccttcatg aaatttg    47

<210> SEQ ID NO 25
<211> LENGTH: 54
<212> TYPE: DNA
<213> ORGANISM: Artificial sequence
<220> FEATURE:
<223> OTHER INFORMATION: Synthetic polynucleotide

<400> SEQUENCE: 25
ctgtacttcc aatccggatc catgacttct ttcgatttcg tcgctaagac tttc    54

<210> SEQ ID NO 26
<211> LENGTH: 49
<212> TYPE: DNA
<213> ORGANISM: Artificial sequence
<220> FEATURE:
<223> OTHER INFORMATION: Synthetic polynucleotide

<400> SEQUENCE: 26
ggtggtggtg gtgctcgagt tagacgtagt accccgagtg aaactttgc    49

<210> SEQ ID NO 27
<211> LENGTH: 50
<212> TYPE: DNA
<213> ORGANISM: Artificial sequence
<220> FEATURE:
<223> OTHER INFORMATION: Synthetic polynucleotide

```
<400> SEQUENCE: 27
ctgtacttcc aatccggatc catgcctgtg tataatggta cgtcacaagc              50

<210> SEQ ID NO 28
<211> LENGTH: 53
<212> TYPE: DNA
<213> ORGANISM: Artificial sequence
<220> FEATURE:
<223> OTHER INFORMATION: Synthetic polynucleotide

<400> SEQUENCE: 28
ggtggtggtg gtgctcgagt tacaggtagt aaccttcatg gaatttgttc ttg          53

<210> SEQ ID NO 29
<211> LENGTH: 49
<212> TYPE: DNA
<213> ORGANISM: Artificial sequence
<220> FEATURE:
<223> OTHER INFORMATION: Synthetic polynucleotide

<400> SEQUENCE: 29
ctgtacttcc aatccggatc catggcggtg tacaatggcg tctcgcagg               49

<210> SEQ ID NO 30
<211> LENGTH: 56
<212> TYPE: DNA
<213> ORGANISM: Artificial sequence
<220> FEATURE:
<223> OTHER INFORMATION: Synthetic polynucleotide

<400> SEQUENCE: 30
ggtggtggtg gtgctcgagc tatagataat agccctcgtg gaacttattt ttcacg       56

<210> SEQ ID NO 31
<211> LENGTH: 22
<212> TYPE: DNA
<213> ORGANISM: Artificial sequence
<220> FEATURE:
<223> OTHER INFORMATION: Synthetic polynucleotide

<400> SEQUENCE: 31
catatggctg ccgcgcggca cc                                            22

<210> SEQ ID NO 32
<211> LENGTH: 28
<212> TYPE: DNA
<213> ORGANISM: Artificial sequence
<220> FEATURE:
<223> OTHER INFORMATION: Synthetic polynucleotide

<400> SEQUENCE: 32
ctcgagcacc accaccacca ccactgag                                      28

<210> SEQ ID NO 33
<211> LENGTH: 1057
<212> TYPE: DNA
<213> ORGANISM: Artificial sequence
<220> FEATURE:
<223> OTHER INFORMATION: Synthetic polynucleotide

<400> SEQUENCE: 33
atgcctgtgt ataatggtac gtcacaagca ttcaattttg cgccgctgca cccagatagt   60
ttgaattggt gcccaaagtc gagtcttcct ccagaaattc ctgtagtgga tctgtcaaaa  120
```

| | |
|---|---|
| cttaattctg aagccgagct ggcacaattt cttgtggaca ttcgtaagag cgggttgttt | 180 |
| tatgtagtca atcatggtgt cccggaagaa ctttctattg ggtgttacaa tcgcttccgt | 240 |
| caattctgta acattcctga ggaccaacgt gcggaatact cgaccgacca tcattttgta | 300 |
| aacgggggct acatgccgta taagagttcc agcatcggca aggcaaataa aggtaaatct | 360 |
| caaaaggact ttgtggttaa atacttctgg cgtggaccgc gcgttgagaa ccgtagtccg | 420 |
| gatgctgatt tcaagagcta tcacgacgaa taccaccgtc gcacagctga tatcgctaac | 480 |
| agcgtgatta ctaaaattct tcaggccctg acgacgcgtt ttcctgactt tgaccctgct | 540 |
| gaatataaag ataacattaa ttcccatcat atgttcttct cgaaccgcct ttacccagac | 600 |
| aacgaacctg agaaaggcga gaatgtagaa taccgtttag taccgcaccg tgacctgagc | 660 |
| ttcgtgaccc ttgctcacca aatcccggcg gacaacggtt accaaggcct tttcgttttt | 720 |
| accggcgatg ggaagaaggt ttgcgtgcct ccgattcgta acagctatct tgtcttcatg | 780 |
| ggacaggcaa tgtcgtatct gacgaataag tacttacctg cagggttgca tggcgtggat | 840 |
| tttcctgaaa agaactgttt cgaggggtct gaacgctcct ctcttatctc attttacgaa | 900 |
| cctcacgatc atatgatgcc cagcaaagca cttacaccta aggatgatga gatcttcgat | 960 |
| cgtggttgtt cgttctttga tgacatcggc gtggacaaaa cagggacgac ctatatgtat | 1020 |
| gtcaagaaca aattccatga aggttactac ctgtaag | 1057 |

<210> SEQ ID NO 34
<211> LENGTH: 1053
<212> TYPE: DNA
<213> ORGANISM: Artificial sequence
<220> FEATURE:
<223> OTHER INFORMATION: Synthetic polynucleotide

<400> SEQUENCE: 34

| | |
|---|---|
| atgacttctt tcgatttcgt cgctaagact ttcgattttg ctcccgtcaa agctgacgag | 60 |
| ttgaagtggt atccacgttc cgcgttacca ccagaaattc ctgtaattga tttgaacaac | 120 |
| gtcaatacgg aggaggagct tgcacagttc ctggtggaca tccgcaagtc tggacttttc | 180 |
| tacgttgtca accacgatat cccggaggaa atctcaatcc agacgtacaa cgaatttcgt | 240 |
| gagttttgta aattgccaga gaggcccgc caaaaataca atactgatcg ctgcttcttc | 300 |
| aatgggggat atgttccatt caaagccacg agcattaatg ggggtaataa gaacaaacag | 360 |
| caacgcgact ttgtcgtgaa gtttttctgg cgcggcccac acgtggtcaa tcgttccccc | 420 |
| aatgaacgct tgccaaatg gcaccatcag tatcatacac gcactgctga attaggtgaa | 480 |
| aaggtcatga ccacaatcgc aaaagctttg aagacgcgct ttcctgactt cgacccggcc | 540 |
| gaactggagg acaatgtgaa ccctcacaac atgattttt ctaaccgcat ttatccggaa | 600 |
| ttcccacca gtgaagggga ggatgctgag tatcgcctga ccccccaccg tgatatttcc | 660 |
| tacattaccc ttgtgaatca gactcctgcc aataacggat tcaaagcatt atttatcgta | 720 |
| accggggacg gcgaacgcgt ttacgtccct cctatccgca actcttactt ggtattcatc | 780 |
| gggcagagct tgagctacct taccaataaa taccttccag cggcacttca cggggtcgct | 840 |
| tttccggacg gcaatcttga gggttgcgag cgtgcctcac tggtgtcttt ctatgaaccg | 900 |
| tatgatcgca tggtcccatc gaaaaatatc aaaccaacgg cagaagagat cgctccaaaa | 960 |
| tcctgctcct tctatgattc gattgggtgt gacaagacag gaactacctt tactgatgtt | 1020 |
| cgtgcaaagt ttcactcggg gtactacgtc taa | 1053 |

<210> SEQ ID NO 35
<211> LENGTH: 482
<212> TYPE: PRT
<213> ORGANISM: Pseudo Nitzschia multiseries

<400> SEQUENCE: 35

```
Met Lys Phe Ala Thr Ser Ile Val Ala Ala Ile Ala Thr Thr Gly Ala
1               5                   10                  15

Ala Phe Thr Val Ile Pro Gln Lys Leu Ser His Pro Ser Gln Leu Asn
                20                  25                  30

Ala Leu Asn Thr Met Gly Ser Ile Ser Ser Ile Thr Ala Glu Ser Pro
            35                  40                  45

Lys Glu Val Leu Ser Arg Val Gln Asp Ala Gly Leu Thr Leu Thr Asn
        50                  55                  60

Pro Asn Asp Leu Tyr Trp Met Val Asp Phe Leu Lys Glu Lys Tyr Tyr
65                  70                  75                  80

Asp Asn Gly Asp Tyr Tyr Tyr Pro Ile Lys Thr Val Cys Asp Gly Glu
                85                  90                  95

Ser Ile Asp Val Lys Phe Tyr Cys Pro Phe Glu Pro Ser Leu Ser Pro
                100                 105                 110

His Tyr Leu Glu Leu Tyr Gly Ser Arg Asp Glu Arg Ala Ser Ile Tyr
            115                 120                 125

Glu Thr Thr Met Lys Lys Tyr Asn Arg Ile Asn Ser Glu Lys Thr Ser
        130                 135                 140

Ala Ile Cys Thr Pro Tyr Ser Ser Tyr Gly Asp Thr Gln Ile Val Ala
145                 150                 155                 160

Tyr Phe Tyr Ser Met Met Tyr Tyr Ile Asn Asp Gln Thr Ala His Leu
                165                 170                 175

Lys Leu Pro Glu Ser Glu Ile Glu Ser Glu Leu Ile Asp Ile Leu Asn
            180                 185                 190

Asp Asp Ile Leu Ile Tyr Leu Asn Glu Phe Met Ser Ile Phe Glu Pro
        195                 200                 205

Glu Asp Ala Gln Asp Leu Glu Arg Ile Trp Asp Phe Leu Asp Phe Tyr
210                 215                 220

Gln Pro Tyr Phe Ser Lys Val Asp Gly Lys Ile Val Leu Asp Glu Lys
225                 230                 235                 240

Tyr Leu Val Arg Thr Pro Ser Gln Met Pro Leu Ile Lys Thr Ile Cys
                245                 250                 255

Glu Tyr Val Ser Glu Gln Phe Ala Pro Ser Lys Asn Ile Thr Gln Val
            260                 265                 270

Ile Trp Glu Val Val Arg Tyr Ile Lys Gly Val Lys Asp Glu Ile His
        275                 280                 285

Ile Arg Gly Asp Lys Ser Phe Thr Leu Ser Leu Gln Glu Tyr Asp Asp
290                 295                 300

Phe Arg Asp Lys Val Thr Ala Ser Pro Met Ala His Ala Val Ser Asp
305                 310                 315                 320

Leu Thr His Glu Arg Phe Ser Tyr Glu Ala Tyr Thr Asn Pro Ala Phe
                325                 330                 335

Met Glu Leu Glu Asn Arg Cys Ser Glu Ile Ile Thr Tyr Phe Asn Asp
            340                 345                 350

Val Cys Thr Ser Asp Arg Glu Arg Leu Asp Glu Asp Pro Phe Asn Ser
        355                 360                 365

Val Phe Ile Leu Met Asp Leu Asp Pro Ser Leu Asn Phe Ala Lys Ser
        370                 375                 380
```

```
Cys Asp Val Val Glu His Ala Tyr Asn Lys Met Gln Ala Phe Leu
385                 390                 395                 400

Lys Leu Lys Glu Glu Ile Leu Glu Ser Ala Ser Asp Glu Glu Arg
            405                 410                 415

Leu Ala Leu Ala Arg Met Ile Lys Thr Arg Glu Asp Ser Leu Ile Gly
            420                 425                 430

Tyr Val Leu His Glu Val Cys Cys Val Glu Asp Gly Tyr Ala Arg Asp
            435                 440                 445

His Lys Pro Leu Met Lys Ala Phe Leu Glu Glu Ile Thr Lys Ser
            450                 455                 460

Leu Ala Glu Lys Val Lys Phe Asn Pro Val Glu Ser Glu Ser Val Arg
465                 470                 475                 480

Leu Asn

<210> SEQ ID NO 36
<211> LENGTH: 373
<212> TYPE: PRT
<213> ORGANISM: Pseudo Nitzschia multiseries

<400> SEQUENCE: 36

Met Thr Val Ala Ile Asn Asn Glu Thr Val Val Leu Thr Pro Asn Glu
1               5                   10                  15

Asp Asp Val Gln Val Asn Lys Gly Lys Thr Leu Glu Thr Ser Phe Pro
                20                  25                  30

Pro Leu Lys Gly Asp Asp Leu Lys Trp Phe Pro Arg Ser Ser Leu Pro
            35                  40                  45

Ala Glu Ile Pro Ala Ile Asp Ile Gly Lys Val Ser Thr Lys Glu Glu
50                  55                  60

Leu Glu Gln Phe Leu Val Asp Ile Arg Lys Ser Gly Leu Phe Tyr Ile
65                  70                  75                  80

Val Asn His Gly Val Pro Glu Glu Val Ser Ile Asn Val Tyr Asn Ala
                85                  90                  95

Phe Arg Glu Phe Ile Ser Thr Thr Thr Glu Glu Arg Met Lys Tyr
            100                 105                 110

Tyr Thr Asp Thr His Phe Gln Asn Gly Gly Tyr Val Pro Phe Gln Gly
            115                 120                 125

Ser Ser Ile Arg Gly Gly Asn Leu Gly Lys Pro Gln Lys Asp His Val
130                 135                 140

Val Lys Tyr Phe Trp Arg Gly Pro Glu Val Ile Asn Arg Thr Pro Asn
145                 150                 155                 160

Glu Lys Phe Thr Glu Ala His Asn Met His Thr Glu Thr Phe Lys
            165                 170                 175

Val Ala Glu Lys Val Ile Arg Thr Ile Phe Lys Ala Leu Lys Leu Arg
            180                 185                 190

Phe Pro Asp Phe Asp Pro Met Glu Phe Glu Asn Thr Ile Asn Ser Lys
            195                 200                 205

Lys Met Phe Phe Thr Asn Arg Ile Tyr Pro Gln Ala Glu Pro Ser Asp
            210                 215                 220

Glu Glu Glu Ile Thr His Arg Leu Val Pro His Leu Asp Thr Ser Phe
225                 230                 235                 240

Ile Thr Leu Ala Asn Gln Val Pro Ala Asp Asn Gly Phe Gln Gly Leu
                245                 250                 255

Phe Val Glu Thr Gly Asp Gly Lys Lys Val Lys Val Pro Gly Ile Arg
            260                 265                 270
```

```
Asn Ser Tyr Leu Val Phe Ile Gly Gln Ser Leu Ser Tyr Leu Thr Lys
        275                 280                 285

Asn Tyr Leu Pro Ser Ala Leu His Gly Val Asp Lys Pro Pro Ser Asp
    290                 295                 300

Leu Phe Glu Gly Ser Glu Arg Ser Ser Leu Ile Thr Phe Tyr Glu Pro
305                 310                 315                 320

Ala Glu Ile Ile Ile Pro Ser Lys Asn Ile Asn Pro Asn Pro Glu Glu
                325                 330                 335

Thr Ser Glu Ser Cys Pro Phe Phe Tyr Asp Ile Gly Leu Thr Val Asn
            340                 345                 350

Asp Pro Glu Gly Thr Thr Trp Asp Phe Val Lys Asn Lys Phe Ile Thr
            355                 360                 365

Gly Tyr Tyr Ala Asp
        370
```